United States Patent [19]

Waldman

[11] Patent Number: 5,879,656
[45] Date of Patent: Mar. 9, 1999

[54] METHODS OF TREATING METASTATIC COLORECTAL CANCER WITH ST RECEPTOR BINDING COMPOUNDS

[75] Inventor: Scott A. Waldman, Ardmore, Pa.

[73] Assignee: Thomas Jefferson University, Philadelphia, Pa.

[21] Appl. No.: 583,447

[22] Filed: Jan. 5, 1996

Related U.S. Application Data

[63] Continuation-in-part of Ser. No. 141,892, Oct. 26, 1993, Pat. No. 5,518,888.

[51] Int. Cl.$^6$ .................. A61K 51/00; A61K 39/395; A61K 34/40; A61M 36/14
[52] U.S. Cl. .................. 424/149; 424/1.69; 424/183.1; 435/7.21; 435/7.23; 435/7.1; 514/2; 514/12; 514/13; 514/14; 514/773; 530/388.2; 530/388.8; 530/388.85; 530/389.7; 530/324; 530/325; 530/326; 530/327
[58] Field of Search .................. 424/1.49, 1.69, 424/183.1; 435/7.21, 7.23; 514/2, 12, 13, 14, 773; 530/388.2, 388.8, 388.85, 389.7, 324, 325, 326, 327

[56] References Cited

U.S. PATENT DOCUMENTS

| | | | |
|---|---|---|---|
| 4,584,268 | 4/1986 | Ceriani et al. | 435/7 |
| 4,867,973 | 9/1989 | Goers et al. | 424/85.91 |
| 4,963,263 | 10/1990 | Kauvar | 210/635 |
| 5,000,935 | 3/1991 | Faulk | 424/1.69 |
| 5,087,616 | 2/1992 | Myers et al. | 514/21 |
| 5,133,886 | 7/1992 | Kauvar | 210/635 |
| 5,143,854 | 9/1992 | Pirrung et al. | 436/518 |
| 5,160,723 | 11/1992 | Welt et al. | 424/1.69 |
| 5,217,869 | 6/1993 | Kauvar | 435/7.9 |
| 5,221,736 | 6/1993 | Coolidge et al. | 536/25.31 |
| 5,223,409 | 6/1993 | Ladner et al. | 435/69.7 |
| 5,237,051 | 8/1993 | Garbers et al. | 530/350 |
| 5,252,743 | 10/1993 | Barrett et al. | 548/303.7 |
| 5,270,170 | 12/1993 | Schatz et al. | 435/7.37 |
| 5,288,514 | 2/1994 | Ellman | 427/2 |
| 5,324,483 | 6/1994 | Cody et al. | 422/131 |
| 5,338,665 | 8/1994 | Schatz et al. | 435/6 |
| 5,340,474 | 8/1994 | Kauvar | 210/198.2 |
| 5,366,382 | 11/1994 | Venton et al. | 435/7.1 |
| 5,384,261 | 1/1995 | Winkler et al. | 436/518 |
| 5,395,750 | 3/1995 | Dillon et al. | 435/5 |
| 5,405,783 | 4/1995 | Pirrung et al. | 436/518 |
| 5,412,087 | 5/1995 | McGall et al. | 536/24.3 |
| 5,420,328 | 5/1995 | Campbell | 558/110 |
| 5,424,186 | 6/1995 | Fodor et al. | 435/6 |
| 5,518,888 | 5/1996 | Waldman | 435/7.23 |
| 5,601,990 | 2/1997 | Waldman | 435/7.23 |

FOREIGN PATENT DOCUMENTS 839512  12/1983  South Africa .

OTHER PUBLICATIONS

PCT International Search Report dated Aug. 7, 1997, 1 page.

Aitken, R. et al., "Recombinant enterotoxins as vaccines against *Escherichia coli*–mediated diarrhoea", *Vaccine*, 1993, 11(2), 227–233.

Chelly, J. et al., "Illegitimate transcription: Transcription of any gene in any cell type", *Proc. Natl. Acad. Sci. USA*, 1989, 86, 2617–2621.

Chelly, J. et al., "Illegitimate Transcription: Application to the Analysis of Truncated Transcripts of the Dystrophin Gene in Nonmuscle Cultured Cells from Duchenne and Becker Patients", *J. Clin. Invest.*, 1991, 88(4), 1161–1166.

Cooper, D.N. et al., "Ectopic (Illegitimate) Transcription: New Possibilities for the Analysis and Diagnosis of Human Genetic Disease", *Ann. Med.*, 1994, 26(1), 9–14.

Field, M., "Role of Cyclic Nucleotides in Enterotoxic Diarrhea", *Mol. Cyclic Nucl. Res.*, 1980, 12, 267–277.

Giannella, R.A., "Pathogenesis of Acute Bacterial Diarrheal Disorders", *Ann. Rev. Med.*, 1981, 32, 341–357.

Kaplan, J.C. et al., "Illegitimate transcription: its use in the study of inherited disease", *Human Mutation*, 1992, 1(5), 357–360 (Abstract only).

Negrier, C. et al., "Illegitimate transcription: its use for studying genetic abnormalities in lymphoblastoid cells from patients with Glanzmann thrombasthenia", *British J. Haematology*, 1998, 100(1), 33–39.

Rao, M.C. et al., "Enterotoxins and Anti–toxins: Enterotoxins and ion transport", *Biochem.*, 1984, 12, 177–180.

(List continued on next page.)

*Primary Examiner*—Lora M. Green
*Assistant Examiner*—Joseph W. Ricigliano
*Attorney, Agent, or Firm*—Woodcock Washburn Kurtz Mackiewicz & Norris, LLP

[57] ABSTRACT

Conjugated compounds which comprises an ST receptor binding moiety and a radiostable active moiety are disclosed. Pharmaceutical compositions comprising a pharmaceutically acceptable carrier or diluent, and a conjugated compound which comprises an ST receptor binding moiety and a radiostable active moiety or an ST receptor binding moiety and a radioactive active moiety are disclosed. Methods of treating an individual suspected of suffering from metastasized colorectal cancer comprising the steps of administering to said individual a pharmaceutical composition comprising a pharmaceutically acceptable carrier or diluent, and a therapeutically effective amount of a conjugated compound which comprises an ST receptor binding moiety and a radiostable active moiety or an ST receptor binding moiety and a radiostable active moiety are disclosed. Methods of radioimaging metastasized colorectal cancer cells comprising the steps of first administering to an individual suspected of having metastasized colorectal cancer cells, a pharmaceutical composition that comprises a pharmaceutically acceptable carrier or diluent, and conjugated compound that comprises an ST receptor binding moiety and a radioactive active moiety wherein the conjugated compound is present in an amount effective for diagnostic use in humans suffering from colorectal cancer and then detecting the localization and accumulation of radioactivity in the individual's body are disclosed.

58 Claims, No Drawings

OTHER PUBLICATIONS

Zippelius, A. et al., "Limitations of Reverse-Transcriptase Polymerase Chain Reaction Analyses for Detection of Micrometastatic Epithelial Cancer Cells in Bone Marrow", *J. Clin. Oncology*, 1997, 15(7), 2701–2708.

Beck–Sickinger et al., "Neuropeptide Y: Identification of the Binding Site", *Int. J. Peptide Protein Res.* 1990, 36, 522–530.

Blond–Elguindi, S. et al., "Affinity Panning of a Library of Peptides Displayed on Bacteriophages Reveals the Binding Specificity of BiP", *Cell* 1993, 75, 717–728.

Bremer, K.H. and Schwarz in "Safety and Efficacy of Radiopharmaceuticals", Kristensen, K. and Norbygaard, eds., Martinus Nijhoff Publishers, Dordrecht, The Netherlands, 1987, pp. 43–50.

Cull, M. et al., "Screening for Receptor Ligands Using Large Libraries of Peptides Linked to the C Terminus of the lac Repressor", *PNAS USA* 1992, 89, 1865–1869.

DeVita, V., "Principles of Cancer Therapy" in Harrison's Principles of Internal Medicine, McGraw–Hill, New York, 1983, pp. 765–787.

Fodor, S., "Light–Directed, Spatially Addressable Parallel Chemical Synthesis", *Science* 1991, 251, 767–773.

Forte, L. and Currie, "Guanylin: a Peptide Regulator of Epithelial Transport", *The FASEB Journal* 1995, 9, 643–650.

Gallop, M. et al., "Applications of Combinatorial Technologies to Drug Discovery. 1. Background and Peptide Combinatorial Libraries", *J. of Medicinal Chem.* 1994, 37(9), 1233–1251.

Gordon, E. et al,. "Applications of Combinatorial Technologies to Drug Discovery. 2. Combinatorial Organic Synthesis, Library Screening Strategies, and Future Directions", *J. of Medicinal Chem.* 1994, 37(10), 1385–1401.

Hammer, J. et al., "Promiscuous and Allele–Specific Anchors in HLA–DR–Binding Peptides", *Cell* 1993, 74, 197–203.

Hamra, F. et al., "Uroguanylin: Structure and Activity of a Second Endogenous Peptide that Stimulates Intestinal Guanylate Cyclase", *PNAS USA* 1993, 90, 10464–10468.

Kita, T. et al., "Characterization of Human Uroguanylin: a Member of the Guanylin Peptide Family", *Amer. J. Physiol.* 1994, 266, F342–F348.

Ohlmeyer, M. et al., "Complex Synthetic Chemical Libraries Indexed with Molecular Tags", *PNAS USA* 1993, 90, 10922–10926.

Ostresh, J. et al., "'Libraries from Libraries': Chemical Transformation of Combinatorial Libraries to Extend the Range and Repertoire of Chemical Diversity", *PNAS USA* 1994, 91, 11138–11142.

Paxton, R. et al., "High–Specific–Activity [111]Labeled Anticarcinoembryonic Antigen Monoclonal Antibody: Improved Method for the Synthesis of Diethylenetriaminepentaacetic Acid Conjugates", *Cancer Research* 1985, 45, 5694–5699.

Ruggeri, Z. et al., "Inhibition of Platelet Function with Synthetic Peptides Designed to be High–affinity Antagonists of Fibrinogen Binding to Platelets", *PNAS USA* 1986, 83, 5708–5712.

Sepetov, N. et al., "Library of Libraries: Approach to Synthetic Combinatorial Library Design and Screening of Pharmacophore Motifs", *PNAS USA* 1995, 92, 5426–5430.

Smith, G. et al., "A Ribonuclease S–peptide Antagonist Discovered with a Bacteriophage Display Library", *Gene* 1993, 128, 37–42.

Tucker, K. and Krejcarek, "Covalent Attachment of Chelating Groups to Macromolecules", *Biochem. and Biophys. Res. Communications* 1977, 77 (2), 581–585.

Vandraager, A. et al., "Guanylyl Cyclase C is an N–Linked Glycoprotein Receptor That Accounts for Multiple Heat-stable Enterotoxin–binding Proteins in the Intestine", *The J. of Biol. Chem.* 1993, 268(3), 2174–2179.

Wang et al., "Application of the Multipin Peptide Synthesis Technique for Peptide Receptor Binding Studies: Substance P as a Model System", *Bioorg. & Med. Chem. Lett.* 1993, 3, 447–450.

Zuckermann, R. et al., "Discovery of Nanomolar Ligands for 7–Transmembrane G–Protein–Coupled Receptors from a Diverse N–(Substituted)glycine Peptoid Library", *J. Med. Chem.* 1994, 37, 2678–2685.

de Sauvage, F. et al., "Primary Structure and Functional Expression of the Human Receptor for *Escherichia coli* Heat–stable Enterotoxin", *The J. of Biol. Chem.* 1991, 266, 17912–17918.

Cohen, M., et al., "Receptors for *Escherichia coli* Heat Stable Enterotoxin in Human Intestine and in a Human Intestinal Cell Line (Caco–2)", *J. of Cellular Physiol.* 1993, 156, 138–144.

Guarino, A. et al., "$T^{84}$ Cell Receptor Binding and Guanyl Cyclas Activation by *Escherichia coli* Heat–Stable Toxin", *Am. J. Physiol.* 253 (Gastrointest. Liver Physiol. 16): G775–780, 1987.

Vaandrager, A. et al, "Atriopeptins and *Escherichia coli* Enterotoxin $ST^a$ Have Different Sites of Aciton in Mammalian Intestine", *Gastroenterology* 1992, 102(4).

Franz et al., "The Production of $^{99m}$Tc–Labeled Conjugated Antibodies Using A Cyclam–Based Bifunctional Chelating Agent", *J. Nucl. Med. Biol.* 1987, 14, 569–572.

Almenoff et al., "Ligand–based Histochemical Localization and Capture of Cells Expressing Heat–Stable Enterotoxin Receptors", *Molecular Microbiol.* 1993, 8, 865–873.

Bjorn et al., "Antibody–Pseudomonas Exotoxin A Conjugates Cytotoxic to Human Breast Cancer Cells In Vitro", *Cancer Research* 1986 46, 3262–3267.

Bjorn et al., "Evaluation of Monoclonal Antibodies for the Development of Breast Cancer Immunotoxins", *Cancer Res.* 1985, 45, 1214–1221.

Bodansky et al., "Peptide Synthesis", John Wiley & Sons, 2d ed., 1976.

Burgess et al., "Biological Evaluation of a MethanolSoluble, Heat–stable *Escherichia coli* Enterotoxin in Infant Mice, Pigs, Rabbits, and Calves", *Infection and Immunity* 1978, 21, 526–531.

Cawley and Herschman, "Epidermal Growth Factor–Toxin A Chain Conjugates: EGF–Ricin A is a Potent Toxin While EGF–Diphtheria Fragment A is Nontoxic", *Cell* 1980, 22, 563–570.

Chan and Giannella, "Amino Acid Sequence of Heat–stable Enterotoxin Produced by *Escherichia coli* Pathogenic for Man", *J. Biol. Chem.* 1981, 256, 7744–7746.

Chung and Collier, "Enzymatically Active Peptide from the Adenosine Diphosphate–Ribosylating Toxin of *pseudomonas Aeruginosa*", *Infection and Immunity* 1977, 16, 832–841.

Cumber et al., "Preparation of Antibody–Toxin Conjugates", *Methods in Enzymology* 1985, 112, 207–225.

Currie et al., "Guanylin: An Endogenous Activator of Intestinal Guanylate Cyclase", *PNAS USA* 1992, 89, 947–951.

Dreyfus et al., "Chemical Properties of Heat–Stable Enterotoxins Produced by Enterotoxigenic *Escherichia Coli* of Different Host Origins", *Infection and Immunity* 1983, 42, 539–548.

Eckelman et al., "Comparison of 99m$^{Tc}$ and $^{111}$ in Labeling of Conjugated Antibodies", *Nucl. Med. Biol.* 1986, 13, 335–343.

Evans et al., "Differences in the Response of Rabbit Small Intestine to Heat–Labile and Heat–Stable Enterotoxins of *Escherichia Coli*", *Infection and Immunity* 1973, 7, 873–880.

Fitzgerald et al., "Adenovirus–Induced Release of Epidermal Growth Factor and Pseudomonas Toxin into the Cytosol of KB Cells During Receptor–Mediated endocytosis", *Cell* 1983, 32, 607–617.

Fitzgerald, "Construction of Immunotoxins Using Pseudomonas Exotoxin A", *Methods in Enzymology* 1987, 151, 139–145.

Giannella et al., "Development of a Radioimmunoassay for *Escherichia coli* Heat–Stable Enterotoxin: Comparison with the Suckling Mouse Bioassay", *Infection and Immunity* 1981, 33, 186–192.

Gros, O., "Biochemical Aspects of Immunotoxin Preparation", *J. Immunol. Meth.* 1985, 81, 283–297.

Gyles, C.L., "Discussion: Heat–Labile and Heat–Stable Forms of the Enterotoxin from *E. Coli* Strains Enteropathogenic for Pigs", *Ann. N.Y. Acad. Sci.* 1979, 16, 314–321.

Hakki et al., "Solubilization and Characterization of Functionally Coupled *Escherichia Coli* Heat–Stable Toxin Receptors and Particulate Guanylate Cyclase Associated with the Cytoskeleton compartment of Intestinal Membranes", *Int. J. Biochem.* 1993, 25, 557–566.

Hugues et al., "Identification and Characterization of a New Family of High–Affinity Receptors for *Escherichia Coli* Heat–Stable Enterotoxin in Rat Intestinal Membranes", *Biochemistry* 1991, 30, 10738–10745.

Humm et al., "Dosimetric Aspects of Radiolabeled Antibodies for Tumor Therapy", *J. of Nuclear Medicine* 1986, 27, 1490–1497.

Klipstein et al., "Development of a Vaccine of Cross–Linked Heat–Stable and Heat–Labile Enterotoxins that Protects Against *Escherichia Coli* Producing Either Enterotoxin", *Infection and Immunity* 1982, 37, 550–557.

Kwok, "Calculation of Radiation Doses for Nonuniformly Distributed $\beta$ and $\gamma$ Radionuclides in Soft Tissue", *Med. Phys.* 1985, 12, 405–412.

Leonard et al., "Kinetics of Protein Synthesis Inactivation in Human T–Lymphocytes by Selective Monoclonal Antibody–Ricin Conjugates", *Cancer Res.* 1985, 45, 5263–5269.

Magerstadt, M., "Antibody Conjugates and Malignant Disease", CRC Press, Boca Raton, FL, 1991, 110–152.

Masuho et al., "Importance of the Antigen–Binding Valency and the Nature of the Cross–Linking Bond in Ricin A–Chain Conjugates with Antibody", *J. Biochem.* 1982, 91, 1583–1591.

Merrifield, "Solid Phase Peptide Synthesis. I. The Synthesis of a Tetrapeptide", *J. Am. Chem. Soc.* 1963, 15, 2149–2514.

Michel and Dirkx, "Fluorescence Studies of Nucleotides Binding to Diphtheria Toxin and Its Fragment A", *Biochimica et Biophysica Acta* 1974, 364, 15–27.

Moseley et al., "Isolation and Nucleotide Sequence Determination of a Gene Encoding a Heat–Stable Enterotoxin of *Escherichia Coli*", *Infection and Immunity* 1983, 39, 1167–1174.

Okamoto et al., "Substitutions of Cysteine Residues of *Escherichia Coli* Heat–Stable Enterotoxin by Oligonucleotide–Directed Mutagenesis", *Infection and Immunity* 1987, 55, 2121–2125.

Richardson et al., "Astatine ($^{211}$At) as a Therapeutic Radionuclide. The Plasma: Blood Cell Distribution in Vitro", *Nucl. Med. Biol.* 1986, 13, 583–584.

Sack, "Human Diarrheal Disease Caused by Enterotoxigenic *Escherichia Coli*", *Ann. Rev. Microbiol.* 1975, 29, 333–353.

Shimonishi et al., "Mode of Disulfide Bond Formation of a Heat–Stable Enterotoxin ($ST_h$) Produced by a Human Strain of Enterotoxigenic *Escherichia Coli*", *FEBS Letters* 1987, 215, 165–170.

So and McCarthy, "Nucleotide Sequence of the Bacterial Transposon Tn1681 Encoding a Heat–Stable (ST) Toxin and its Identification in Enterotoxigenic *Escherichia Coli* Strains", *PNAS USA* 1980, 77, 4011–4015.

Spitler et al., "Therapy of Patients with Malignant Melanoma Using a Monoclonal Antimelanoma Antibody–Ricin A Chain Immunotoxin", *Cancer Res.* 1987, 47, 1717–1723.

Steinsträsser et al., "Selection of Nuclides for Immunoscintigraphy/Immunotherapy", *J. Nucl. Med.* 1988, 5, 875.

Thompson et al., "Biological and Immunological Characteristics of $^{125}$I–4Tyr and –18Tyr *Escherichia coli* Heat––Stable Enterotoxin Species Purified by High–Performance Liquid Chromatography", *Analytical Biochem.* 1985, 148, 26–36.

Thorpe et al., "New Coupling Agents for the Synthesis of Immunotoxins Containing a Hindered Disulfide Bond with Improved Stability In Vivo", *Cancer Res.* 1987, 47, 5924–5931.

Waldman and O'Hanley, "Influence of a Glycine or Proline Substitution on the Functional Properties of a 14–Amino–Acid Analog of *Escherichia Coli* Heat–Stable Enterotoxin", *Infection and Immunity* 1989, 57, 2420–2424.

Wessels and Rogus, "Radionuclide Selection and Model Absorbed Dose Calculations for Radiolabeled Tumor Associated Antibodies", *Med. Phys.* 1984, 11, 638–645.

Worrell et al., "Effect of Linkage Variation on Pharmacokinetics of Ricin A Chain–Antibody Conjugates in Normal Rats", *Anti–Cancer Drug Design* 1986, 1, 179–188.

Yoshimura et al., "Essential Structure for Full Enterotoxigenic Activity of Heat–Stable Enterotoxin Produced by Enterotoxigenic *Escherichia Coli*", *FEBS* 1985, 181, 138–142.

Corstens et al., "Chemotactic Peptides: New Locomotion for Imaging Infection?", *J. Nucl. Med.* 1991, 32(3), 491–494.

Fischman et al., "A Ticket to Ride: Peptide Radiopharmaceuticals", *J. Nucl. Med.* 1993, 34, 2253–2263.

Thompson, "*Escherichia coli* Heat–Stable Enterotoxins and Their Receptors", *Pathol. Immunopathol.* 1987, 6, 103–116.

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: both ( i i ) MOLECULE TYPE: cDNA ( i x ) FEATURE:
        ( A ) NAME/KEY: CDS
        ( B ) LOCATION: 1..57

( x i ) SEQUENCE DESCRIPTION: SEQ ID NO:1:

```
AAC  AAC  ACA  TTT  TAC  TGC  TGT  GAA  CTT  TGT  TGT  AAT  CCT  GCC  TGT  GCT    48
Asn  Asn  Thr  Phe  Tyr  Cys  Cys  Glu  Leu  Cys  Cys  Asn  Pro  Ala  Cys  Ala
 1              5                        10                       15

GGA  TGT  TAT                                                                      57
Gly  Cys  Tyr
```

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Asn  Asn  Thr  Phe  Tyr  Cys  Cys  Glu  Leu  Cys  Cys  Asn  Pro  Ala  Cys  Ala
 1              5                        10                       15

Gly  Cys  Tyr
```

( 2 ) INFORMATION FOR SEQ ID NO:3:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Asn  Thr  Phe  Tyr  Cys  Cys  Glu  Leu  Cys  Cys  Tyr  Pro  Ala  Cys  Ala  Gly
 1              5                        10                       15

Cys  Asn
```

( 2 ) INFORMATION FOR SEQ ID NO:4:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: both ( i i ) MOLECULE TYPE: cDNA ( i x ) FEATURE:
        ( A ) NAME/KEY: CDS
        ( B ) LOCATION: 1..57

( x i ) SEQUENCE DESCRIPTION: SEQ ID NO:4:

```
AAT  AGT  AGC  AAT  TAC  TGC  TGT  GAA  TTG  TGT  TGT  AAT  CCT  GCT  TGT  AAC    48
Asn  Ser  Ser  Asn  Tyr  Cys  Cys  Glu  Leu  Cys  Cys  Asn  Pro  Ala  Cys  Asn
 1              5                        10                       15

GGG  TGC  TAT                                                                      57
```

Gly Cys Tyr (2) INFORMATION FOR SEQ ID NO:5:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:5:

Asn Ser Ser Asn Tyr Cys Cys Glu Leu Cys Cys Asn Pro Ala Cys Asn
1               5                   10                  15

Gly Cys Tyr (2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:6:

Pro Asn Thr Cys Glu Ile Cys Ala Tyr Ala Ala Cys Thr Gly Cys
1               5                   10                  15

(2) INFORMATION FOR SEQ ID NO:7:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:7:

Asn Asn Thr Phe Tyr Cys Cys Glu Leu Cys Cys Asn Pro Ala Cys Ala
1               5                   10                  15

Gly Cys (2) INFORMATION FOR SEQ ID NO:8:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:8:

Asn Thr Phe Tyr Cys Cys Glu Leu Cys Cys Asn Pro Ala Cys Ala Gly
1               5                   10                  15

Cys (2) INFORMATION FOR SEQ ID NO:9:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:9:

Thr Phe Tyr Cys Cys Glu Leu Cys Cys Asn Pro Ala Cys Ala Gly Cys
1               5                   10                  15

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Phe Tyr Cys Cys Glu Leu Cys Cys Asn Pro Ala Cys Ala Gly Cys
1           5                   10                  15

( 2 ) INFORMATION FOR SEQ ID NO:11:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

Tyr Cys Cys Glu Leu Cys Cys Asn Pro Ala Cys Ala Gly Cys
1           5                   10

( 2 ) INFORMATION FOR SEQ ID NO:12:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

Cys Cys Glu Leu Cys Cys Asn Pro Ala Cys Ala Gly Cys
1           5                   10

( 2 ) INFORMATION FOR SEQ ID NO:13:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Asn Thr Phe Tyr Cys Cys Glu Leu Cys Cys Asn Pro Ala Cys Ala Gly
1               5                   10                  15

Cys Tyr ( 2 ) INFORMATION FOR SEQ ID NO:14:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

Thr Phe Tyr Cys Cys Glu Leu Cys Cys Asn Pro Ala Cys Ala Gly Cys
1               5                   10                  15

Tyr ( 2 ) INFORMATION FOR SEQ ID NO:15:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Phe  Tyr  Cys  Cys  Glu  Leu  Cys  Cys  Asn  Pro  Ala  Cys  Ala  Gly  Cys  Tyr
 1                    5                        10                       15
```

( 2 ) INFORMATION FOR SEQ ID NO:16:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Tyr  Cys  Cys  Glu  Leu  Cys  Cys  Asn  Pro  Ala  Cys  Ala  Gly  Cys  Tyr
 1               5                        10                       15
```

( 2 ) INFORMATION FOR SEQ ID NO:17:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Cys  Cys  Glu  Leu  Cys  Cys  Asn  Pro  Ala  Cys  Ala  Gly  Cys  Tyr
 1          5                         10
```

( 2 ) INFORMATION FOR SEQ ID NO:18:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Asn  Thr  Phe  Tyr  Cys  Cys  Glu  Leu  Cys  Cys  Tyr  Pro  Ala  Cys  Ala  Gly
 1                    5                        10                       15
Cys
```

( 2 ) INFORMATION FOR SEQ ID NO:19:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Thr  Phe  Tyr  Cys  Cys  Glu  Leu  Cys  Cys  Tyr  Pro  Ala  Cys  Ala  Gly  Cys
 1                    5                        10                       15
```

( 2 ) INFORMATION FOR SEQ ID NO:20:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
Phe  Tyr  Cys  Cys  Glu  Leu  Cys  Cys  Tyr  Pro  Ala  Cys  Ala  Gly  Cys
 1                  5                       10                           15
```

( 2 ) INFORMATION FOR SEQ ID NO:21:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Tyr  Cys  Cys  Glu  Leu  Cys  Cys  Tyr  Pro  Ala  Cys  Ala  Gly  Cys
 1             5                       10
```

( 2 ) INFORMATION FOR SEQ ID NO:22:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
Cys  Cys  Glu  Leu  Cys  Cys  Tyr  Pro  Ala  Cys  Ala  Gly  Cys
 1                  5                       10
```

( 2 ) INFORMATION FOR SEQ ID NO:23:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

```
Thr  Phe  Tyr  Cys  Cys  Glu  Leu  Cys  Cys  Tyr  Pro  Ala  Cys  Ala  Gly  Cys
 1                  5                            10                           15
Asn
```

( 2 ) INFORMATION FOR SEQ ID NO:24:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

```
Phe  Tyr  Cys  Cys  Glu  Leu  Cys  Cys  Tyr  Pro  Ala  Cys  Ala  Gly  Cys  Asn
 1                  5                       10                           15
```

( 2 ) INFORMATION FOR SEQ ID NO:25:

( i ) SEQUENCE CHARACTERISTICS:

(A) LENGTH: 15 amino acids
            (B) TYPE: amino acid
            (D) TOPOLOGY: linear (ii) MOLECULE TYPE: peptide (xi) SEQUENCE DESCRIPTION: SEQ ID NO:25:

Tyr Cys Cys Glu Leu Cys Cys Tyr Pro Ala Cys Ala Gly Cys Asn
 1               5                  10                  15

(2) INFORMATION FOR SEQ ID NO:26:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (xi) SEQUENCE DESCRIPTION: SEQ ID NO:26:

Cys Cys Glu Leu Cys Cys Tyr Pro Ala Cys Ala Gly Cys Asn
 1               5                  10

(2) INFORMATION FOR SEQ ID NO:27:

(i) SEQUENCE CHARACTERISTICS:
            (A) LENGTH: 18 amino acids
            (B) TYPE: amino acid
            (D) TOPOLOGY: linear (ii) MOLECULE TYPE: peptide (xi) SEQUENCE DESCRIPTION: SEQ ID NO:27:

Asn Ser Ser Asn Tyr Cys Cys Glu Leu Cys Cys Asn Pro Ala Cys Thr
 1               5                  10                  15
Gly Cys (2) INFORMATION FOR SEQ ID NO:28:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (xi) SEQUENCE DESCRIPTION: SEQ ID NO:28:

Ser Ser Asn Tyr Cys Cys Glu Leu Cys Cys Asn Pro Ala Cys Thr Gly
 1               5                  10                  15
Cys (2) INFORMATION FOR SEQ ID NO:29:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:29:

Ser Asn Tyr Cys Cys Glu Leu Cys Cys Asn Pro Ala Cys Thr Gly Cys
 1               5                  10                  15

(2) INFORMATION FOR SEQ ID NO:30:

(i) SEQUENCE CHARACTERISTICS:
            (A) LENGTH: 15 amino acids (B) TYPE: amino acid
(D) TOPOLOGY: linear (i i) MOLECULE TYPE: peptide (x i) SEQUENCE DESCRIPTION: SEQ ID NO:30:

Asn Tyr Cys Cys Glu Leu Cys Cys Asn Pro Ala Cys Thr Gly Cys
1               5                   1 0                  1 5

(2) INFORMATION FOR SEQ ID NO:31:

(i) SEQUENCE CHARACTERISTICS:
(A) LENGTH: 14 amino acids
(B) TYPE: amino acid
(D) TOPOLOGY: linear (i i) MOLECULE TYPE: peptide (x i) SEQUENCE DESCRIPTION: SEQ ID NO:31:

Tyr Cys Cys Glu Leu Cys Cys Asn Pro Ala Cys Thr Gly Cys
1               5                   1 0

(2) INFORMATION FOR SEQ ID NO:32:

(i) SEQUENCE CHARACTERISTICS:
(A) LENGTH: 13 amino acids
(B) TYPE: amino acid
(D) TOPOLOGY: linear (i i) MOLECULE TYPE: peptide (x i) SEQUENCE DESCRIPTION: SEQ ID NO:32:

Cys Cys Glu Leu Cys Cys Asn Pro Ala Cys Thr Gly Cys
1               5                   1 0

(2) INFORMATION FOR SEQ ID NO:33:

(i) SEQUENCE CHARACTERISTICS:
(A) LENGTH: 18 amino acids
(B) TYPE: amino acid
(D) TOPOLOGY: linear (i i) MOLECULE TYPE: peptide (x i) SEQUENCE DESCRIPTION: SEQ ID NO:33:

Ser Ser Asn Tyr Cys Cys Glu Leu Cys Cys Asn Pro Ala Cys Thr Gly
1               5                   1 0                  1 5

Cys Tyr (2) INFORMATION FOR SEQ ID NO:34:

(i) SEQUENCE CHARACTERISTICS:
(A) LENGTH: 17 amino acids
(B) TYPE: amino acid
(D) TOPOLOGY: linear (i i) MOLECULE TYPE: peptide (x i) SEQUENCE DESCRIPTION: SEQ ID NO:34:

Ser Asn Tyr Cys Cys Glu Leu Cys Cys Asn Pro Ala Cys Thr Gly Cys
1               5                   1 0                  1 5

Tyr (2) INFORMATION FOR SEQ ID NO:35:

(i) SEQUENCE CHARACTERISTICS:
(A) LENGTH: 16 amino acids
(B) TYPE: amino acid (D) TOPOLOGY: linear (ii) MOLECULE TYPE: peptide (xi) SEQUENCE DESCRIPTION: SEQ ID NO:35:

Asn Tyr Cys Cys Glu Leu Cys Cys Asn Pro Ala Cys Thr Gly Cys Tyr
1               5                   10                  15

(2) INFORMATION FOR SEQ ID NO:36:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:36:

Tyr Cys Cys Glu Leu Cys Cys Asn Pro Ala Cys Thr Gly Cys Tyr
1               5                   10                  15

(2) INFORMATION FOR SEQ ID NO:37:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:37:

Cys Cys Glu Leu Cys Cys Asn Pro Ala Cys Thr Gly Cys Tyr
1               5                   10

(2) INFORMATION FOR SEQ ID NO:38:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:38:

Asn Thr Phe Tyr Cys Cys Glu Leu Cys Cys Asn Pro Ala Cys Ala Gly
1               5                   10                  15

Cys Tyr (2) INFORMATION FOR SEQ ID NO:39:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:39:

Asn Thr Phe Tyr Cys Cys Glu Leu Cys Cys Ala Pro Ala Cys Ala Gly
1               5                   10                  15

Cys Tyr (2) INFORMATION FOR SEQ ID NO:40:

(i) SEQUENCE CHARACTERISTICS:
        (A) LENGTH: 18 amino acids
        (B) TYPE: amino acid
        (D) TOPOLOGY: linear ( i i ) MOLECULE TYPE: peptide ( x i ) SEQUENCE DESCRIPTION: SEQ ID NO:40:

Asn Thr Phe Tyr Cys Cys Glu Leu Cys Cys Asn Ala Ala Cys Ala Gly
1               5                   1 0                  1 5

Cys Tyr ( 2 ) INFORMATION FOR SEQ ID NO:41:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:41:

Asn Thr Phe Tyr Cys Cys Glu Leu Cys Cys Asn Pro Ala Cys Ala Gly
1               5                   1 0                  1 5

Cys ( 2 ) INFORMATION FOR SEQ ID NO:42:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:

Tyr Cys Cys Glu Leu Cys Cys Asn Pro Ala Cys Ala Gly Cys Tyr
1               5                   1 0                  1 5

( 2 ) INFORMATION FOR SEQ ID NO:43:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:43:

Tyr Cys Cys Glu Leu Cys Cys Asn Pro Ala Cys Ala Gly Cys
1               5                   1 0

( 2 ) INFORMATION FOR SEQ ID NO:44:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:44:

Cys Cys Glu Leu Cys Cys Asn Pro Ala Cys Ala Gly Cys Tyr
1               5                   1 0

( 2 ) INFORMATION FOR SEQ ID NO:45:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:45:

Cys Cys Glu Leu Cys Cys Asn Pro Ala Cys Ala Gly Cys
1               5                   10

( 2 ) INFORMATION FOR SEQ ID NO:46:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:46:

Gln Ala Cys Asp Pro Pro Ser Pro Pro Ala Glu Val Cys Cys Asp Val
1               5                   10                  15
Cys Cys Asn Pro Ala Cys Ala Gly Cys
            20                  25

( 2 ) INFORMATION FOR SEQ ID NO:47:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:47:

Ile Asp Cys Cys Ile Cys Cys Asn Pro Ala Cys Phe Gly Cys Leu Asn
1               5                   10                  15

( 2 ) INFORMATION FOR SEQ ID NO:48:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:48:

Ser Ser Asp Trp Asp Cys Cys Asp Val Cys Cys Asn Pro Ala Cys Ala
1               5                   10                  15
Gly Cys ( 2 ) INFORMATION FOR SEQ ID NO:49:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:49:

Asn Ser Ser Asn Tyr Cys Cys Glu Leu Cys Cys Tyr Pro Ala Cys Thr
1               5                   10                  15
Gly Cys Tyr ( 2 ) INFORMATION FOR SEQ ID NO:50:

( i ) SEQUENCE CHARACTERISTICS:
        ( A ) LENGTH: 13 amino acids
        ( B ) TYPE: amino acid (D) TOPOLOGY: linear (ii) MOLECULE TYPE: peptide (xi) SEQUENCE DESCRIPTION: SEQ ID NO:50:

```
Cys Cys Asp Val Cys Cys Asn Pro Ala Cys Thr Gly Cys
1               5                   10
```

(2) INFORMATION FOR SEQ ID NO:51:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:51:

```
Cys Cys Asp Val Cys Cys Tyr Pro Ala Cys Thr Gly Cys Tyr
1               5                   10
```

(2) INFORMATION FOR SEQ ID NO:52:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:52:

```
Cys Cys Asp Leu Cys Cys Asn Pro Ala Cys Ala Gly Cys Tyr
1               5                   10
```

(2) INFORMATION FOR SEQ ID NO:53:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:53:

```
Cys Cys Gln Leu Cys Cys Asn Pro Ala Cys Thr Gly Cys Tyr
1               5                   10
```

(2) INFORMATION FOR SEQ ID NO:54:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:54:

```
Pro Gly Thr Cys Glu Ile Cys Ala Tyr Ala Ala Cys Thr Gly Cys
1               5                   10                  15
```

(2) INFORMATION FOR SEQ ID NO:55:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:55:

```
Gln  Glu  Asp  Cys  Glu  Leu  Cys  Ile  Asn  Val  Ala  Cys  Thr  Gly  Cys
1              5                        10                       15
```

( 2 ) INFORMATION FOR SEQ ID NO:56:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:56:

```
Asn  Asp  Asp  Cys  Glu  Leu  Cys  Val  Asn  Val  Ala  Cys  Thr  Gly  Cys  Leu
1              5                        10                       15
```

METHODS OF TREATING METASTATIC COLORECTAL CANCER WITH ST RECEPTOR BINDING COMPOUNDS

CROSS REFERENCE TO RELATED APPLICATIONS

This application is a continuation in part of U.S. Ser. No. 08/141,892, filed Oct. 26, 1993, which is incorporated herein by reference and which issued May 21, 1996 as U.S. Pat. No. 5,518,888. Related applications U.S. Ser. No. 08/305,056, filed Sep. 13, 1994, now U.S. Pat. No. 5,601,990, U.S. Ser. No. 08/468,449 filed Jun. 6, 1995, U.S. Ser. No. 08/467,920 filed Jun. 6, 1995, and PCT application PCT/US94/12232 filed Oct. 26, 1994 are each incorporated herein by reference.

ACKNOWLEDGMENT OF GOVERNMENT RIGHTS

This invention was made with Government support under grant number DK43805-01A2 awarded by the National Institutes of Health. The Government has certain rights in this invention.

FIELD OF THE INVENTION

The present invention relates to compounds which comprise a receptor ligand moiety conjugated to an active agent. More particularly, the present invention relates to compounds which comprise a moiety that binds to the ST receptor conjugated to a therapeutic or imaging moiety.

BACKGROUND OF THE INVENTION

Colorectal cancer is the third most common neoplasm worldwide and the second most common in the United States, representing about 15% of the newly diagnosed cases of cancer in the United States. The large intestine or large bowel is the third leading site for the development of new cancer and is diagnosed in about 150,000 patients each year. Colorectal cancer is the second leading cause of cancer-related deaths and is responsible for about 12% of cancer deaths in the United States. The mortality rate of newly diagnosed large bowel cancer approaches 50% and there has been little improvement over the past 40 years. Most of this mortality reflects local, regional and distant metastases. About thirty percent of patients with colorectal cancer have unresectable disease at presentation and about 40% develop metastases during the course of their disease. Distant metastatic disease is seen in liver (about 12%), lung (about 3%), bone (about 0.9%), brain (about 0.7%), nodes (about 4%), and peritoneum (about 2%) at the time of initial diagnosis. In 1987, the large bowel cancers found regionally or at distant sites at the time of diagnosis were about 26% and about 18%, respectively.

Surgery is the mainstay of treatment for colorectal cancer but recurrence is frequent. Colorectal cancer has proven resistant to chemotherapy, although limited success has been achieved using a combination of 5-fluorouracil and levamisole. Surgery has had the largest impact on survival and, in some patients with limited disease, achieves a cure. However, surgery removes bulk tumor, leaving behind microscopic residual disease which ultimately results in recrudescence. Overall recurrence rates for colonic tumors are about 33% and for rectal cancer about 42%. Of these recurrences, about 9%, are local, about 13% are systemic metastatic disease, and the remaining 88% are a combination of local and systemic disease. Fifty percent of patients with recurrent colorectal cancer have hepatic metastases.

Early detection of primary, metastatic, and recurrent disease can significantly impact the prognosis of individuals suffering from colorectal cancer. Large bowel cancer diagnosed at an early stage has a significantly better outcome than that diagnosed at more advanced stages. The 5 year relative survival rates for patients with regional or distant metastases are 48% and 5%, compared with 90% and 77% for disease which is in situ or local, respectively, at the time of diagnosis. Similarly, diagnosis of metastatic or recurrent disease earlier potentially carries with it a better prognosis.

Although current radiotherapeutic agents, chemotherapeutic agents and biological toxins are potent cytotoxins, they do not discriminate between normal and malignant cells, producing adverse effects and dose-limiting toxicities. Over the past decade, a novel approach has been employed to more specifically target agents to tumor cells, involving the conjugation of an active agent to molecules which binds preferentially to antigens that exist predominantly on tumor cells. These conjugates can be administered systemically and specifically bind to the targeted tumor cells. Theoretically, targeting permits uptake by cells of cytotoxic agents at concentrations which do not produce serious toxicities in normal tissues. Also, selective binding to targeted tumor cells facilitates detection of occult tumor and is therefore useful in designing imaging agents. Molecular targeting predominantly has employed monoclonal antibodies generated to antigens selectively expressed on tumor cells.

Immunoscintigraphy using monoclonal antibodies directed at tumor-specific markers has been employed to diagnose colorectal cancer. Monoclonal antibodies against carcinoembryonic antigen (CEA) labeled with $^{99}$Technetium identified 94% of patients with recurrent tumors. Similarly, $^{111}$Indium-labeled anti-CEA monoclonal antibodies successfully diagnosed 85% of patients with recurrent colorectal carcinoma who were not diagnosed by conventional techniques. $^{125}$Iodine-labeled antibodies have been effective in localizing more than 80% of the pathologically-confirmed recurrences by intraoperative gamma probe scanning.

Monoclonal antibodies have also been employed to target specific therapeutic agents in colorectal cancer. Preclinical studies demonstrated that anti-CEA antibodies labeled with $^{90}$Yttrium inhibited human colon carcinoma xenografts in nude mice. Antibodies generated to colorectal. cancer cells and coupled to mitomycin C or neocarzinostatin demonstrated an anti-tumor effect on human colon cancer xenografts in nude mice and 3 patients with colon cancer. Similar results in animals were obtained with monoclonal antibodies conjugated to ricin toxin A chain.

Due to the sensitivity, specificity, and adverse-effect profile of monoclonal antibodies, the results obtained using monoclonal antibody-based therapeutics have shown them to be less than ideal targeting tools. Although monoclonal antibodies have been generated to antigens selectively expressed on tumors, no truly cancer-specific antibody has been identified. Most antigens expressed on neoplastic cells appear to be quantitatively increased in these compared to normal cells but the antigens are nonetheless often present in normal cells. Thus, antibodies to such determinants can react with non-neoplastic tissues, resulting in significant toxicities. Also, antibodies are relatively large molecules and consequently, often evoke an immune response in patients. These immune responses can result in significant toxicities in patients upon re-exposure to the targeting agents and can prevent targeting by the monoclonal due to immune complex formation with degradation and excretion. Finally, binding of antibodies to tumor cells may be low and targeted agents may be delivered to cells in quantities insufficient to achieve detection or cytotoxicity.

There remains a need for compositions which can specifically target metastasized colorectal cancer cells. There is a need for imaging agents which can specifically bind to metastasized colorectal cancer cells. There is a need for improved methods of imaging metastasized colorectal cancer cells. There is a need for therapeutic agents which can specifically bind to metastasized colorectal cancer cells. There is a need for improved methods of treating individuals who are suspected of suffering from colorectal cancer cells, especially individuals who are suspected of suffering from metastasis of colorectal cancer cells.

SUMMARY OF THE INVENTION

The present invention relates to conjugated compounds which comprises an ST receptor binding moiety and a radiostable active moiety.

The present invention relates to a pharmaceutical composition comprising a pharmaceutically acceptable carrier or diluent, and a conjugated compound which comprises an ST receptor binding moiety and a radiostable active moiety.

The present invention relates to a method of treating an individual suspected of suffering from metastasized colorectal cancer comprising the steps of administering to said individual a pharmaceutical composition comprising a pharmaceutically acceptable carrier or diluent, and a therapeutically effective amount of a conjugated compound which comprises an ST receptor binding moiety and a radiostable active moiety.

The present invention relates to a pharmaceutical composition comprising a pharmaceutically acceptable carrier or diluent, and conjugated compound that comprises an ST receptor binding moiety and a radioactive active moiety wherein the conjugated compound is present in an amount effective for therapeutic or diagnostic use in humans suffering from colorectal cancer.

The present invention relates to a method of radioimaging metastasized colorectal cancer cells comprising the steps of first administering to an individual suspected of having metastasized colorectal cancer cells, a pharmaceutical composition that comprises a pharmaceutically acceptable carrier or diluent, and conjugated compound that comprises an ST receptor binding moiety and a radioactive active moiety wherein the conjugated compound is present in an amount effective for diagnostic use in humans suffering from colorectal cancer and then detecting the localization and accumulation of radioactivity in the individual's body.

The present invention relates to a method of treating an individual suspected of suffering from metastasized colorectal cancer comprising the steps of administering to said individual a pharmaceutical composition comprising a pharmaceutically acceptable carrier or diluent, and a therapeutically effective amount of a conjugated compound which comprises an ST receptor binding moiety and a radioactive active moiety.

DESCRIPTION OF PREFERRED EMBODIMENTS OF THE INVENTION

As used herein, the terms "ST" and "native ST" are used interchangeably and are meant to refer to heat-stable toxin (ST) which is a peptide produced by *E. coli*, as well as other organisms. STs are naturally occurring peptides which 1) are naturally produced by organisms, 2) which bind to the ST receptor and 3) which activate the signal cascade that mediates ST-induced diarrhea.

As used herein, the term "ST receptor" is meant to refer to the receptors found on colorectal cells, including local and metastasized colorectal cancer cells, which bind to ST. In normal individuals, ST receptors are found exclusively in cells of intestine, in particular in cells in the duodenum, small intestine (jejunum and ileum), the large intestine, colon (cecum, ascending colon, transverse colon, descending colon and sigmoid colon) and rectum.

As used herein, the term "ST receptor ligand" is meant to refer to compounds which specifically bind to the ST receptor. ST is an ST receptor ligand. An ST receptor ligand may be a peptide or a non-peptide.

As used herein, the term "ST receptor binding peptide" is meant to refer to ST receptor ligands that are peptides.

As used herein, the term "ST peptides" is meant to refer to ST receptor binding peptides selected from the group consisting of SEQ ID NO:2, SEQ ID NO:3, SEQ ID NOS:5–56 and fragments and derivatives thereof.

As used herein, the term "fragment" is meant to refer to peptide a) which has an amino acid sequence identical to a portion of an ST receptor binding peptide and b) which is capable of binding to the ST receptor.

As used herein, the term "derivative" is meant to refer to a peptide a) which has an amino acid sequence substantially identical to at least a portion of an ST receptor binding peptide and b) which is capable of binding to the ST receptor.

As used herein, the term "substantially identical" is meant to refer to an amino acid sequence that is the same as the amino acid sequence of an ST peptide except some of the residues are deleted or substituted with conservative amino acids or additional amino acids are inserted.

As used herein, the term "active agent" is meant to refer to compounds that are therapeutic agents or imaging agents.

As used herein, the term "radiostable" is meant to refer to compounds which do not undergo radioactive decay; i.e. compounds which are not radioactive.

As used herein, the term "therapeutic agent" is meant to refer to chemotherapeutics, toxins, radiotherapeutics, targeting agents or radiosensitizing agents.

As used herein, the term "chemotherapeutic" is meant. to refer to compounds that, when contacted with and/or incorporated into a cell, produce an effect on the cell. including causing the death of the cell, inhibiting cell division or inducing differentiation.

As used herein, the term "toxin" is meant to refer to compounds that, when contacted with and/or incorporated into a cell, produce the death of the cell.

As used herein, the term "radiotherapeutic" is meant to refer to radionuclides which when contacted with and/or incorporated into a cell, produce the death of the cell.

As used herein, the term "targeting agent" is meant to refer compounds which can be bound by and or react with other compounds. Targeting agents may be used to deliver chemotherapeutics, toxins, enzymes, radiotherapeutics, antibodies or imaging agents to cells that have targeting agents associated with them and/or to convert or otherwise transform or enhance coadministered active agents. A targeting agent may include a moiety that constitutes a first agent that is localized to the cell which when contacted with a second agent either is converted to a third agent which has a desired activity or causes the conversion of the second agent into an agent with a desired activity. The result is the localized agent facilitates exposure of an agent with a desired activity to the metastasized cell.

As used herein, the term "radiosensitizing agent" is meant to refer to agents which increase the susceptibility of cells to the damaging effects of ionizing radiation. A radiosensitizing agent permits lower doses of radiation to be administered and still provide a therapeutically effective dose.

As used herein, the term "imaging agent" is meant to refer to compounds which can be detected.

As used herein, the term "ST receptor binding moiety" is meant to refer to the portion of a conjugated compound that constitutes an ST receptor ligand.

As used herein, the term "active moiety" is meant to refer to the portion of a conjugated compound that constitutes an active agent.

As used herein, the terms "conjugated compound" and "conjugated composition" are used interchangeably and meant to refer to a compound which comprises an ST receptor binding moiety and an active moiety and which is capable of binding to the ST receptor. Conjugated compounds according to the present invention comprise a portion which constitutes an ST receptor ligand and a portion which constitutes an active agent. Thus, conjugated compounds according to the present invention are capable of specifically binding to the ST receptor and include a portion which is a therapeutic agent or imaging agent. Conjugated compositions may comprise crosslinkers and/or molecules that serve as spacers between the moieties.

As used herein, the terms "crosslinker", "crosslinking agent", "conjugating agent", "coupling agent", "condensation reagent" and "bifunctional crosslinker" are used interchangeably and are meant to refer to molecular groups which are used to attach the ST receptor ligand and the active agent to thus form the conjugated compound.

As used herein, the term "colorectal cancer" is meant to include the well-accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). Additionally, as used herein, the term "colorectal cancer" is meant to further include medical conditions which are characterized by cancer of cells of the duodenum and small intestine (jejunum and ileum). The definition of colorectal cancer used herein is more expansive than the common medical definition but is provided as such since the cells of the duodenum and small intestine also contain ST receptors and are therefore amenable to the methods of the present invention using the compounds of the present invention.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. The present invention relates to methods of delivering active agents to metastasized colorectal cancer cells.

As used herein, the term "metastasized colorectal cancer cells" is meant to refer to colorectal cancer cells which have metastasized; colorectal cancer cells localized in a part of the body other than the duodenum, small intestine (jejunum and ileum), large intestine (colon), including the cecum, ascending colon, transverse colon, descending colon, and sigmoid colon, and rectum.

ST, which is produced by E. coli, as well as other organisms, is responsible for endemic diarrhea in developing countries and travelers diarrhea. ST induces intestinal secretion by binding to specific receptors, ST receptors, in the apical brush border membranes of the mucosal cells lining the intestinal tract. Binding of ST to ST receptors is non-covalent and occurs in a concentration-dependent and saturable fashion. Once bound, ST—ST receptor complexes appear to be internalized by intestinal cells, i.e. transported from the surface into the interior of the cell. Binding of ST to ST receptors triggers a cascade of biochemical reactions in the apical membrane of these cells resulting in the production of a signal which induces intestinal cells to secrete fluids and electrolytes, resulting in diarrhea.

ST receptors are unique in that they are only localized in the apical brush border membranes of the cells lining the intestinal tract. Indeed, they are not found in any other cell type in placental mammals. In addition, ST receptors are almost exclusively localized to the apical membranes, with little being found in the basolateral membranes on the sides of intestinal cells.

Mucosal cells lining the intestine are joined together by tight junctions which form a barrier against the passage of intestinal contents into the blood stream and components of the blood stream into the intestinal lumen. Therefore, the apical location of ST receptors isolates these receptors from the circulatory system so that they may be considered to exist separate from the rest of the body; essentially the "outside" of the body. Therefore, the rest of the body is considered "outside" the intestinal tract. Compositions administered "outside" the intestinal tract are maintained apart and segregated from the only cells which normally express ST receptors.

In individuals suffering from colorectal cancer, the cancer cells are often derived from cells that produce and display the ST receptor and these cancer cells continue to produce and display the ST receptor on their cell surfaces. Indeed, T84 cells, which are human colonic adenocarcinoma cells isolated from lung metastases, express ST receptors on their cell surface. Similarly, HT29glu-cells, which are human colonic adenocarcinoma cells, express receptors for ST. Thus, in individuals suffering from colorectal cancer, some metastasized intestinal cancer cells express ST receptors.

An effort was undertaken to determine the proportion of colorectal tumors which have the ST receptor. Sixteen colorectal cancer tumors, including ten local colorectal tumors and six metastasized tumors (3 liver, 1 lung, 1 lymphnode, 1 peritoneum), were tested and each possessed ST receptors. In each case, the affinity and density of receptors was amenable for targeting. That is, the cells possessed at least $10^4$–$10^6$ receptors per cell and demonstrated an affinity of $10^{-7}$ or better (that is preferably between $10^{-8}$ to $10^{-9}$ or less; the lower number indicating a tighter bond, thus a higher affinity). Normal liver, lymphnode, peritoneum and lung cells were found not to possess ST receptors.

When such cancer cells metastasize, the metastasized cancer cells continue to produce and display the ST receptor. The expression of ST receptors on the surfaces of metastatic tumors provides a target for selective binding of conjugated compositions. ST receptors permit the absolutely specific targeting of therapeutic and diagnostic agents that are conjugated to ST receptor ligands to metastatic colorectal cancer cells.

The conjugated compositions of the present invention are useful for targeting cells that line the inner intestine wall including those cancer cells derived from such cells, particularly metastasized cancer cells derived from such cells.

The conjugated compositions of the present invention which are administered outside the intestinal tract such as those administered in the circulatory system will remain segregated from the cells that line the intestinal tract and will bind only to cells outside the intestinal tract which are derived from the intestinal tract such as metastasized colorectal cells. The conjugated compositions will not bind to non-colorectal derived cells. Thus, the active moieties of conjugated compositions administered outside the intestinal tract are delivered to cells which are derived from the intestinal tract such as metastasized colorectal cells but will not be delivered to any other cells.

Therapeutic and diagnostic pharmaceutical compositions of the present invention include conjugated compounds specifically targeted to metastatic disease. These conjugated compounds include ST receptor binding moieties which do not bind to cells of normal tissue in the body except cells of the intestinal tract since the cells of other tissues do not possess ST receptors. Unlike normal colorectal cells and localized colorectal cancer cells, metastasized colorectal cancer cells are accessible to substances administered outside the intestinal tract, for example administered in the circulatory system. The only ST receptors in normal tissue exist in the apical membranes of intestinal mucosa cells and these receptors are effectively isolated from the targeted cancer chemotherapeutics and imaging agents administered outside the intestinal tract by the intestinal mucosa barrier. Thus, metastasized colorectal cells may be targeted by conjugated compounds of the present invention by introducing such compounds outside the intestinal tract such as for example by administering pharmaceutical compositions that comprise conjugated compounds into the circulatory system.

One having ordinary skill in the art can readily identify individuals suspected of suffering from colorectal cancer and metastasized colorectal cells. In those individuals diagnosed with colorectal cancer, it is standard therapy to suspect metastasis and aggressively attempt to eradicate metastasized cells. The present invention provides pharmaceutical compositions and methods for imaging and thereby will more definitively diagnose metastasis. Further, the present invention provides pharmaceutical compositions, comprising therapeutic agents and methods for specifically targeting and eliminating metastasized colorectal cancer cells. Further, the present invention provides pharmaceutical compositions that comprise therapeutics and methods for specifically eliminating colorectal cancer cells.

The pharmaceutical compositions which comprise conjugated compositions of the present invention may be used to diagnose or treat individuals suffering from localized colorectal tumors, that is primary or non-metastatic colorectal tumors if these have penetrated the basement membrane underlying the mucosa into the submucosa where there is abundant blood supply to which they have access. Penetration into the submucosa circumvents the mucosal barrier resulting in the ability of conjugated compositions introduced into the circulatory system to interact with these tumors.

The present invention relies upon the use of an ST receptor binding moiety in a conjugated composition. The ST receptor binding moiety is essentially a portion of the conjugated composition which acts as a ligand to the ST receptor and thus specifically binds to these receptors. The conjugated composition also includes an active moiety which is associated with the ST receptor binding moiety; the active moiety being an active agent which is either useful to image, target, neutralize or kill the cell.

According to the present invention, the ST receptor binding moiety is the ST receptor ligand portion of a conjugated composition. In some embodiments, the ST receptor ligand may be native ST.

Native ST has been isolated from a variety of organisms including E. coli, Yersinia, Enterobacter, and others. In nature, the toxins are generally encoded on a plasmid which can "jump" between different species. Several different toxins have been reported to occur in different species. These toxins all possess significant sequence homology, they all bind to ST receptors and they all activate guanylate cyclase, producing diarrhea.

ST has been both cloned and synthesized by chemical techniques. The cloned or synthetic molecules exhibit binding characteristics which are similar to native ST. Native ST isolated from *E. coli* is 18 or 19 amino acids in length. The smallest "fragment" of ST which retains activity is the 13 amino acid core peptide extending toward the carboxy terminal from cysteine 6 to cysteine 18 (of the 19 amino acid form). Analogues of ST have been generated by cloning and by chemical techniques. Small peptide fragments of the native ST structure which include the structural determinant that confers binding activity may be constructed. Once a structure is identified which binds to ST receptors, non-peptide analogues mimicking that structure in space are designed.

SEQ ID NO:1 discloses a nucleotide sequence which encodes 19 amino acid ST, designated ST Ia, reported by So and McCarthy (1980) *Proc. Natl. Acad. Sci. USA* 77:4011, which is incorporated herein by reference.

The amino acid sequence of ST Ia is disclosed in SEQ ID NO:2.

SEQ ID NO:3 discloses the amino acid sequence of an 18 amino acid peptide which exhibits ST activity, designated ST I*, reported by Chan and Giannella (1981) *J. Biol. Chem.* 256:7744, which is incorporated herein by reference.

SEQ ID NO:4 discloses a nucleotide sequence which encodes 19 amino acid ST, designated ST Ib, reported by Mosely et al. (1983) *Infect. Immun.* 39:1167, which is incorporated herein by reference.

The amino acid sequence of ST Ib is disclosed in SEQ ID NO:5.

A 15 amino acid peptide called guanylin which has about 50% sequence homology to ST has been identified in mammalian intestine (Currie, M. G. et al. (1992) *Proc. Natl. Acad Sci. USA* 89:947–951, which is incorporated herein by reference). Guanylin binds to ST receptors and activates guanylate cyclase at a level of about 10- to 100-fold less than native ST. Guanylin may not exist as a 15 amino acid peptide in the intestine but rather as part of a larger protein in that. organ. The amino acid sequence of guanylin from rodent is disclosed as SEQ ID NO:6.

SEQ ID NO:7 is an 18 amino acid fragment of SEQ ID NO:2. SEQ ID NO:8 is a 17 amino acid fragment of SEQ ID NO:2. SEQ ID NO:9 is a 16 amino acid fragment of SEQ ID NO:2. SEQ ID NO:10 is a 15 amino acid fragment of SEQ ID NO:2. SEQ ID NO:11 is a 14 amino acid fragment of SEQ ID NO:2. SEQ ID NO:12 is a 13 amino acid fragment of SEQ ID NO:2. SEQ ID NO:13 is an 18 amino acid fragment of SEQ ID NO:2. SEQ ID NO:14 is a 17 amino acid fragment of SEQ ID NO:2. SEQ ID NO:15 is a 16 amino acid fragment of SEQ ID NO:2. SEQ ID NO:16 is a 15 amino acid fragment of SEQ ID NO:2. SEQ ID NO:17 is a 14 amino acid fragment of SEQ ID NO:2.

SEQ ID NO:18 is a 17 amino acid fragment of SEQ ID NO:3. SEQ ID NO:19 is a 16 amino acid fragment of SEQ ID NO:3. SEQ ID NO:20 is a 15 amino acid fragment of SEQ ID NO:3. SEQ ID NO:21 is a 14 amino acid fragment of SEQ ID NO:3. SEQ ID NO:22 is a 13 amino acid fragment of SEQ ID NO:3. SEQ ID NO:23 is a 17 amino acid fragment of SEQ ID NO:3. SEQ ID NO:24 is a 16 amino acid fragment of SEQ ID NO:3. SEQ ID NO:25 is a 15 amino acid fragment of SEQ ID NO:3. SEQ ID NO:26 is a 14 amino acid fragment of SEQ ID NO:3.

SEQ ID NO:27 is an 18 amino acid fragment of SEQ ID NO:5. SEQ ID NO:28 is a 17 amino acid fragment of SEQ ID NO:5. SEQ ID NO:29 is a 16 amino acid fragment of SEQ ID NO:5. SEQ ID NO:30 is a 15 amino acid fragment of SEQ ID NO:5. SEQ ID NO:31 is a 14 amino acid fragment of SEQ ID NO:5. SEQ ID NO:32 is a 13 amino acid fragment of SEQ ID NO:5. SEQ ID NO:33 is an 18 amino acid fragment of SEQ ID NO:5. SEQ ID NO:34 is a 17 amino acid fragment of SEQ ID NO:5. SEQ ID NO:35 is a 16 amino acid fragment of SEQ ID NO:5. SEQ ID NO:36 is a 15 amino acid fragment of SEQ ID NO:5. SEQ ID NO:37 is a 14 amino acid fragment of SEQ ID NO:5.

SEQ ID NO:27, SEQ ID NO:31, SEQ ID NO:36 AND SEQ ID NO:37 are disclosed in Yoshimura, S., et al. (1985) *FEBS Lett.* 181:138, which is incorporated herein by reference.

SEQ ID NO:38, SEQ ID NO:39 and SEQ ID NO:40, which are derivatives of SEQ ID NO:3, are disclosed in Waldman, S. A. and O'Hanley, P. (1989) *Infect. Immun.* 57:2420, which is incorporated herein by reference.

SEQ ID NO:41, SEQ ID NO:42, SEQ ID NO:43, SEQ ID NO:44 and SEQ ID NO:45, which are a derivatives of SEQ ID NO:3, are disclosed in Yoshimura, S., et al. (1985) *FEBS Lett.* 181:138, which is incorporated herein by reference.

SEQ ID NO:46 is a 25 amino acid peptide derived from *Y. enterocolitica* which binds to the ST receptor.

SEQ ID NO:47 is a 16 amino acid peptide derived from *V. cholerae* which binds to the ST receptor. SEQ ID NO:47 is reported in Shimonishi, Y., et al. *FEBS Lett.* 215:165, which is incorporated herein by reference.

SEQ ID NO:48 is an 18 amino acid peptide derived from *Y. enterocolitica* which binds to the ST receptor. SEQ ID NO:48 is reported in Okamoto, K., et al. *Infec. Immun.* 55:2121, which is incorporated herein by reference.

SEQ ID NO:49, is a derivative of SEQ ID NO:5.

SEQ ID NO:50, SEQ ID NO:51, SEQ ID NO:52 and SEQ ID NO:53 are derivatives.

SEQ ID NO:54 is the amino acid sequence of guanylin from human.

A 15 amino acid peptide called uroguanylin has been identified in mammalian intestine from opossum (Hamra, S. K. et al. (1993) *Proc. Natl. Acad Sci. USA* 90:10464–10468, which is incorporated herein by reference; see also Forte L. and M. Curry 1995 *FASEB* 9:643–650; which is incorporated herein by reference). SEQ ID NO:55 is the amino acid sequence of uroguanylin from opossum.

A 16 amino acid peptide called uroguanylin has been identified in mammalian intestine from human (Kita, T. et al. (1994) *Amer. J. Physiol.* 266:F342–348, which is incorporated herein by reference; see also Forte L. and M. Curry 1995 *FASEEB* 9:643–650; which is incorporated herein by reference). SEQ ID NO:56 is the amino acid sequence of uroguanylin from human.

In some preferred embodiments, conjugated compounds comprise ST receptor binding moieties that comprise amino acid sequences selected from the group consisting of SEQ ID NO:2, SEQ ID NO:3, SEQ ID NOS:5–56 and fragments and derivatives thereof.

Those having ordinary skill in the art can readily design and produce derivatives having substantially identical amino acid sequences of ST peptides with deletions and/or insertions and/or conservative substitutions of amino acids. For example, following what are referred to as Dayhof's rules for amino acid substitution (Dayhof, M. D. (1978) *Nat. Biomed. Res. Found.*, Washington, D.C. Vol. 5, supp. 3), amino acid. residues in a peptide sequence may be substituted with comparable amino acid residues. Such substitutions are well-known and are based the upon charge and structural characteristics of each amino acid. Derivatives include fragments of ST receptor binding peptides with deletions and/or insertions and/or conservative substitutions.

In some embodiments, ST receptor binding peptides comprise D amino acids. As used herein, the term "D amino acid peptides" is meant to refer to ST receptor binding peptides, fragments or derivatives which comprise at least one and preferably a plurality of D amino acids which are capable of binding to the ST receptor. The use of D amino acid peptides is desirable as they are less vulnerable to degradation and therefore have a longer half-life. D amino acid peptides comprising mostly all or consisting of D amino acids may comprise amino acid sequences in the reverse order of ST receptor binding peptides which are made up of L amino acids.

In some embodiments, ST receptor binding peptides, including D amino acid peptides, are conformationally restricted to present and maintain the proper structural conformation for binding to the ST receptor. The compositions may comprise additional amino acid residues required to achieve proper three dimensional conformation including residues which facilitate circularization or desired folding.

It is preferred that the ST receptor ligand used as the ST receptor binding moiety be as small as possible. Thus it is preferred that the ST receptor ligand be a non-peptide small molecule or small peptide, preferably less than 25 amino acids, more preferably less than 20 amino acids. In some embodiments, the ST receptor ligand which constitute the ST receptor binding moiety of a conjugated composition is less than 15 amino acids. ST receptor binding peptide comprising less than 10 amino acids and ST receptor binding peptide less than 5 amino acids may be used as ST binding moieties according to the present invention. It is within the scope of the present invention to include larger molecules which serve as ST receptor binding moieties including, but not limited to molecules such as antibodies, FAbs and F(Ab)2s which specifically bind to ST receptor.

An assay may be used to test both peptide and non-peptide compositions to determine whether or not they are ST receptor ligands or, to test conjugated compositions to determine if they possess ST receptor binding activity. Such compositions that specifically bind to ST receptors can be identified by a competitive binding assay. The competitive binding assay is a standard technique in pharmacology which can be readily performed by those having ordinary skill in the art using readily available starting materials. Competitive binding assays have been shown to be effective for identifying compositions that specifically bind to ST receptors. Briefly, the assay consists of incubating a preparation of ST receptors (e.g. intestinal membranes from rat intestine, human intestine, T84 cells) with a constant concentration ($1 \times 10^{-10}$M to $5 \times 10^{-10}$M) of $^{125}$I-ST (any ST receptor ligand such as native STs SEQ ID NO:2, SEQ ID NO:3 or SEQ ID NO:5 may be used) and a known concentration of a test compound. As a control, a duplicate preparation of ST receptors are incubated with a duplicate concentration of $^{125}$I-ST in the absence of test compound.

Assays are incubated to equilibrium (2 hours) and the amount of $^{125}$I-ST bound to receptors is quantified by standard techniques. The ability of the test compound to bind to receptors is measured as its ability to prevent (compete with) the $^{125}$I-ST from binding. Thus, in assays containing the test compound which bind to the receptor, there will be less radioactivity associated with the receptors. This assay, which is appropriate for determining the ability of any molecule to bind to ST receptors, is a standard competitive binding assay which can be readily employed by those having ordinary skill in the art using readily available starting materials.

ST may be isolated from natural sources using standard techniques. Additionally, ST receptor binding peptides and conjugated compositions or portions thereof which are peptides may be prepared routinely by any of the following known techniques.

ST receptor binding peptides and conjugated compositions or portions thereof which are peptides may be prepared using the solid-phase synthetic technique initially described by Merrifield, in *J. Am. Chem. Soc.*, 15:2149–2154 (1963). Other peptide synthesis techniques may be found, for example, in M. Bodanszky et al., (1976) *Peptide Synthesis*, John Wiley & Sons, 2d Ed.; Kent and Clark-Lewis in *Synthetic Peptides in Biology and Medicine*, p. 295–358, eds. Alitalo, K., et al. Science Publishers, (Amsterdam, 1985); as well as other reference works known to those skilled in the art. A summary of peptide synthesis techniques may be found in J. Stuart and J. D. Young, *Solid Phase Peptide Synthelia*, Pierce Chemical Company, Rockford, Ill. (1984), which is incorporated herein by reference. The synthesis of peptides by solution methods may also be used, as described in *The Proteins*, Vol. II, 3d Ed., p. 105–237, Neurath, H. et al., Eds., Academic Press, New York, N.Y. (1976). Appropriate protective groups for use in such syntheses will be found in the above texts, as well as in J. F. W. McOmie, *Protective Groups in Organic Chemistry*, Plenum Press, New York, N.Y. (1973), which is incorporated herein by reference. In general, these synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

ST receptor binding peptides and conjugated compositions or portions thereof which are peptides may also be prepared by recombinant DNA techniques. Provision of a suitable DNA sequence encoding the desired peptide permits the production of the peptide using recombinant techniques now known in the art. The coding sequence can be obtained from natural sources or synthesized or otherwise constructed using widely available starting materials by routine methods. When the coding DNA is prepared synthetically, advantage can be taken of known codon preferences of the intended host where the DNA is to be expressed.

To produce an ST receptor binding peptide which occurs in nature, one having ordinary skill in the art can, using well-known techniques, obtain a DNA molecule encoding the ST receptor binding peptides from the genome of the organism that produces the ST receptor binding peptide and insert that DNA molecule into a commercially available expression vector for use in well-known expression systems.

Likewise, one having ordinary skill in the art can, using well known techniques, combine a DNA molecule that encodes an ST receptor binding peptide, such as SEQ ID NO:1 and SEQ ID NO:4, which can be obtained from the genome of the organism that produces the ST, with DNA that encodes a toxin, another active agent that is a peptide or additionally, any other amino acid sequences desired to be adjacent to the ST receptor binding peptide amino acid sequence in a single peptide and insert that DNA molecule into a commercially available expression vector for use in well-known expression systems.

For example, the commercially available plasmid pSE420 (Invitrogen, San Diego, Calif.) may be used for recombinant production in *E. coli*. The commercially available plasmid pYES2 (Invitrogen, San Diego, Calif.) may be used for production in *S. cerevisiae* strains of yeast. The commercially available MaxBac™ (Invitrogen, San Diego, Calif.) complete baculovirus expression system may be used for production in insect cells. The commercially available plasmid pcDNA I (Invitrogen, San Diego, Calif.) may be used for production in mammalian cells such as Chinese Hamster Ovary cells.

One having ordinary skill in the art may use these or other commercially available expression vectors and systems or produce vectors using well-known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989). Thus, the desired proteins can be prepared in both prokaryotic and eukaryotic systems, resulting in a spectrum of processed forms of the protein.

The most commonly used prokaryotic system remains *E. coli*, although other systems such as *B. subtilis* and Pseudomonas are also useful. Suitable control sequences for prokaryotic systems include both constitutive and inducible promoters including the lac promoter, the trp promoter, hybrid promoters such as tac promoter, the lambda phage Pl promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but are not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionene promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well-known techniques, isolate the protein that is produced.

According to the present invention, the active moiety may be a therapeutic agent or an imaging agent. One having ordinary skill in the art can readily recognize the advantages of being able to specifically target metastasized colorectal cells with an ST receptor ligand and conjugate such a ligand with many different active agents.

Chemotherapeutics useful as active moieties which when conjugated to an ST receptor binding moiety are specifically delivered to metastasized colorectal cells are typically, small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication. Examples of chemotherapeutics include common cytotoxic or cytostatic drugs such as for example: methotrexate (amethopterin), doxorubicin (adrimycin), daunorubicin, cytosinarabinoside, etoposide, 5-4 fluorouracil, melphalan, chlorambucil, and other nitrogen mustards (e.g. cyclophosphamide), cis-platinum, vindesine (and other vinca alkaloids), mitomycin and bleomycin. Other chemotherapeutics include: purothionin (barley flour oligopeptide), macromomycin. 1,4-benzoquinone derivatives and trenimon.

Toxins are useful as active moieties. When a toxin is conjugated to an ST receptor binding moiety, the conjugated composition is specifically delivered to a metastasized colorectal cell by way of the ST receptor binding moiety and the toxin moiety kills the cell. Toxins are generally complex toxic products of various organisms including bacteria, plants, etc. Examples of toxins include but are not limited to: ricin, ricin A chain (ricin toxin), Pseudomonas exotoxin (PE), diphtheria toxin (DT), Clostridium perfringens phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin. As discussed above, when protein toxins are employed with ST receptor binding peptides, conjugated compositions may be produced using recombinant DNA techniques. Briefly, a recombinant DNA molecule can be constructed which encodes both the ST receptor ligand and the toxin on a chimeric gene. When the chimeric gene is expressed, a fusion protein is produced which includes an ST receptor binding moiety and an active moiety. Protein toxins are also useful to form conjugated compounds with ST receptor binding peptides through non-peptidyl bonds.

In addition, there are other approaches for utilizing active agents for the treatment of cancer. For example, conjugated compositions may be produced which include an ST binding moiety and an active moiety which is an active enzyme. The ST binding moiety specifically localizes the conjugated composition to the tumor cells. An inactive prodrug which can be converted by the enzyme into an active drug is administered to the patient. The prodrug is only converted to an active drug by the enzyme which is localized to the tumor. An example of an enzyme/prodrug pair includes alkaline phosphatase/etoposidephosphate. In such a case, the alkaline phosphatase is conjugated to an ST receptor binding ligand. The conjugated compound is administered and localizes at the metastasized cell. Upon contact with etoposidephosphate (the prodrug), the etoposidephosphate is converted to etoposide, a chemotherapeutic drug which is taken up by the cancer cell.

Radiosensitizing agents are substances that increase the sensitivity of cells to radiation. Examples of radiosensitizing agents include nitroimidazoles, metronidazole and misonidazole (see: DeVita, V. T. Jr. in *Harrison's Principles of Internal Medicine*, p.68, McGraw-Hill Book Co., N.Y. 1983, which is incorporated herein by reference). The conjugated compound that comprises a radiosensitizing agent as the active moiety is administered and localizes at the metastasized cell. Upon exposure of the individual to radiation, the radiosensitizing agent is "excited" and causes the death of the cell.

Radionuclides may be used in pharmaceutical compositions that are useful for radiotherapy or imaging procedures.

Examples of radionuclides useful as toxins in radiation therapy include: $^{47}Sc$, $^{67}Cu$, $^{90}Y$, $^{109}Pd$, $^{123}I$, $^{125}I$, $^{131}I$, $^{186}Re$, $^{188}Re$, $^{199}Au$, $^{211}At$, $^{212}Pb$ and $^{212}B$. Other radionuclides which have been used by those having ordinary skill in the art include: $^{32}P$ and $^{33}P$, $^{71}Ge$, $^{77}As$, $^{103}Pb$, $^{105}Rh$, $^{111}Ag$, $^{119}Sb$, $^{121}Sn$, $^{131}Cs$, $^{143}Pr$, $^{161}Tb$, $^{177}Lu$, $^{191}Os$, $^{193M}Pt$, $^{197}Hg$, all beta negative and/or auger emitters. Some preferred radionuclides include: $^{90}Y$, $^{131}I$ $^{211}At$ and $^{212}Pb/^{212}Bi$.

According to the present invention, the active moieties may be an imaging agent. Imaging agents are useful diagnostic procedures as well as the procedures used to identify the location of metastasized cells. Imaging can be performed by many procedures well-known to those having ordinary skill in the art and the appropriate imaging agent useful in such procedures may be conjugated to an ST receptor ligand by well-known means. Imaging can be performed, for example, by radioscintigraphy, nuclear magnetic resonance imaging (MRI) or computed tomography (CT scan). The most commonly employed radionuclide imaging agents include radioactive iodine and indium. Imaging by CT scan may employ a heavy metal such as iron chelates. MRI scanning may employ chelates of gadolinium or manganese. Additionally, positron emission tomography (PET) may be possible using positron emitters of oxygen, nitrogen, iron, carbon, or gallium. Example of radionuclides useful in imaging procedures include: $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113}$In, $^{123}$I, $^{125}$I, $^{127}$Cs, $^{129}$Cs, $^{131}$I, $^{132}$I, $^{197}$Hg, $^{203}$Pb and $^{206}$Bi.

It is preferred that the conjugated compositions be non-immunogenic or immunogenic at a very low level. Accordingly, it is preferred that the ST receptor binding moiety be a small, poorly immunogenic or non-immunogenic peptide or a non-peptide. Likewise, it is preferred that the active moiety be a small, poorly-immunogenic or non-immunogenic peptide or a non-peptide. Native ST, being a small peptide, has been shown to poorly immunogenic. (See: Klipstein, F. A. et al. (1982) *Infect. Immun.* 37:550–557; Giannella, R. A. et al. (1981) *Infect. Immun.* 33:186; Burgess, M. N. et al. (1978) *Infect. Immun.* 21:60; Evans, D. G. et al. (1973) *Infect. Immun.* 7:873; Gyles, C. L. (1979) *Ann. N.Y. Acad. Sci.* 16:314; and Sack, R. B. (1975) *Ann. Rev. Microbiol.* 29:333.) Similarly, fragments and amino acid substitute derivatives of native ST are poorly immunogenic. Accordingly, conjugated compositions which include all or part of the native ST as an ST receptor binding moiety are generally poorly immunogenic to the extent that the native ST is poorly immunogenic.

ST receptor ligands are conjugated to active agents by a variety of well-known techniques readily performed without undue experimentation by those having ordinary skill in the art. The technique used to conjugate the ST receptor ligand to the active agent is dependent upon the molecular nature of the ST receptor ligand and the active agent. After the ST receptor ligand and the active agent are conjugated to form a single molecule, assays may be performed to ensure that the conjugated molecule retains the activities of the moieties. The ST receptor binding assay described above may be performed using the conjugated compound to test whether it is capable of binding to the ST receptor. Similarly, the activity of the active moiety may be tested using various assays for each respective type of active agent. Radionuclides retain there activity, i.e. their radioactivity, irrespective of conjugation. With respect to active agents which are toxins, drugs and targeting agents, standard assays to demonstrate the activity of unconjugated forms of these compounds may be used to confirm that the activity has been retained.

Conjugation may be accomplished directly between the ST receptor ligand and the active agent or linking, intermediate molecular groups may be provided between the ST receptor ligand and the active agent. Crosslinkers are particularly useful to facilitate conjugation by providing attachment sites for each moiety. Crosslinkers may include additional molecular groups which serve as spacers to separate the moieties from each other to prevent either from interfering with the activity of the other.

In some preferred embodiments, the ST receptor ligand peptide is SEQ ID NO:2, SEQ ID NO:3, SEQ ID NOS:5–56 or fragments or derivatives thereof. It has been observed that conjugation to these molecules is preferably performed at the amino terminus of each respective peptide. In ST receptor ligand peptides comprising D amino acid sequences in the opposite order as SEQ ID NO:2, SEQ ID NO:3, SEQ ID NOS:5–56, conjugation preferably is performed at the carboxy terminus.

One having ordinary skill in the art may conjugate an ST receptor ligand peptide to a chemotherapeutic drug using well-known techniques. For example, Magerstadt, M. *Antibody Conjugates and Malignant Disease.* (1991) CRC Press, Boca Raton, USA, pp. 110–152) which is incorporated herein by reference, teaches the conjugation of various cytostatic drugs to amino acids of antibodies. Such reactions may be applied to conjugate chemotherapeutic drugs to ST receptor ligands, including ST receptor binding peptides, with an appropriate linker. ST receptor ligands which have a free amino group such as ST receptor binding peptides may be conjugated to active agents at that group. Most of the chemotherapeutic agents currently in use in treating cancer possess functional groups that are amenable to chemical crosslinking directly with proteins. For example, free amino groups are available or methotrexate, doxorubicin, daunorubicin, cytosinarabinoside, cis-platin, vindesine, mitomycin and bleomycin while free carboxylic acid groups are available on methotrexate, melphalan, and chlorambucil. These functional groups, that is free amino and carboxylic acids, are targets for a variety of homobifunctional and heterobifunctional chemical crosslinking agents which can crosslink these drugs directly to the single free amino group of ST. For example, one procedure for crosslinking ST receptor ligands which have a free amino group such as ST receptor binding peptides, as for example SEQ ID NO:2, SEQ ID NO:3, SEQ ID NO:5–56 to active agents which have a free amino group such as methotrexate, doxorubicin, daunorubicin, cytosinarabinoside, cis-platin, vindesine, mitomycin and bleomycin, or alkaline phosphatase, or protein-or peptide-based toxin employs homobifunctional succinimidyl esters, preferably with carbon chain spacers such as disuccinimidyl suberate (Pierce Co, Rockford, Ill.). In the event that a cleavable conjugated compound is required, the same protocol would be employed utilizing 3,3'-dithiobis (sulfosuccinimidylpropionate; Pierce Co.).

In order to conjugate an ST receptor ligand peptide to a peptide-based active agent such as a toxin, the ST receptor ligand and the toxin may be produced as a single, fusion protein either by standard peptide synthesis or recombinant DNA technology, both of which can be routinely performed by those having ordinary skill in the art. Alternatively, two peptides, the ST receptor ligand peptide and the peptide-based toxin may be produced and/or isolated as separate peptides and conjugated using crosslinkers. As with conjugated compositions that contain chemotherapeutic drugs, conjugation of ST receptor binding peptides and toxins can exploit the ability to modify the single free amino group of an ST receptor binding peptide while preserving the receptor-binding function of this molecule.

One having ordinary skill in the art may conjugate an ST receptor ligand peptide to a radionuclide using well-known techniques. For example, Magerstadt, M. (1991) *Antibody Conjugates And Malignant Disease*, CRC Press, Boca Raton, Fla., and Barchel, S. W. and Rhodes, B. H., (1983) *Radioimaging and Radiotherapy*, Elsevier, NY, N.Y., each of which is incorporated herein by reference, teach the conjugation of various therapeutic and diagnostic radionuclides to amino acids of antibodies. Such reactions may be applied to conjugate radionuclides to ST receptor ligand peptides or to ST receptor ligands including ST receptor ligand peptides with an appropriate linker.

The present invention provides pharmaceutical compositions that comprise the conjugated compounds of the invention and pharmaceutically acceptable carriers or diluents. The pharmaceutical composition of the present invention may be formulated by one having ordinary skill in the art. Suitable pharmaceutical carriers are described in *Remington's Pharmaceutical Sciences*, A. Osol, a standard reference text in this field, which is incorporated herein by reference. In carrying out methods of the present invention, conjugated compounds of the present invention can be used alone or in combination with other diagnostic, therapeutic or additional agents. Such additional agents include excipients such as coloring, stabilizing agents, osmotic agents and antibacterial agents.

The conjugated compositions of the invention can be, for example, formulated as a solution, suspension or emulsion in association with a pharmaceutically acceptable parenteral vehicle. Examples of such vehicles are water, saline, Ringer's solution, dextrose solution, and 5% human serum albumin. Liposomes may also be used. The vehicle may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as either a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions of the present invention may be administered by any means that enables the conjugated composition to reach the targeted cells. In some embodiments, routes of administration include those selected from the group consisting of intravenous, intraarterial, intraperitoneal, local administration into the blood supply of the organ in which the tumor resides or directly into the tumor itself. Intravenous administration is the preferred mode of administration. It may be accomplished with the aid of an infusion pump.

The dosage administered varies depending upon factors such as: the nature of the active moiety; the nature of the conjugated composition; pharmacodynamic characteristics; its mode and route of administration; age, health, and weight of the recipient; nature and extent of symptoms; kind of concurrent treatment; and frequency of treatment.

Because conjugated compounds are specifically targeted to cells with ST receptors, conjugated compounds which comprise chemotherapeutics or toxins are administered in doses less than those which are used when the chemotherapeutics or toxins are administered as unconjugated active agents, preferably in doses that contain up to 100 times less active agent. In some embodiments, conjugated compounds which comprise chemotherapeutics or toxins are administered in doses that contain 10–100 times less active agent as an active moiety than the dosage of chemotherapeutics or toxins administered as unconjugated active agents. To determine the appropriate dose, the amount of compound is preferably measured in moles instead of by weight. In that way, the variable weight of different ST binding moieties does not affect the calculation. Presuming a one to one ratio of ST binding moiety to active moiety in conjugated compositions of the invention, less moles of conjugated compounds may be administered as compared to the moles of unconjugated compounds administered, preferably up to 100 times less moles.

Typically, chemotherapeutic conjugates are administered intravenously in multiple divided doses.

Up to 20 gm IV/dose of methotrexate is typically administered in an unconjugated form. When methotrexate is administered as the active moiety in a conjugated compound of the invention, there is a 10- to 100-fold dose reduction. Thus, presuming each conjugated compound includes one molecule of methotrexate conjugated to one ST receptor binding moiety, of the total amount of conjugated compound administered, up to about 0.2–2.0 g of methotrexate is present and therefore administered. In some embodiments, of the total amount of conjugated compound administered, up to about 200 mg–2 g of methotrexate is present and therefore administered.

Methotrexate has a molecular weight of 455. One mole of the ST peptide-methotrexate conjugate weighs between about 1755–2955 depending on the ST peptide used. The effective dose range for ST peptide-methotrexate conjugate is between about 10 to 1000 mg. In some embodiments, dosages of 50 to 500 mg of ST peptide-methotrexate conjugate are administered. In some embodiments, dosages of 80 to 240 mg of ST peptide-methotrexate conjugate are administered.

Doxorubicin and daunorubicin each weigh about 535. Thus, ST peptide-doxorubicin conjugates and ST peptide-daunorubicin conjugates each have molecular weights of between about 1835–2553.5. Presuming each conjugated compound includes one molecule of doxorubicin or daunorubicin conjugated to one ST receptor binding moiety, the effective dose range for ST peptide-doxorubicin conjugate or ST peptide-daunorubicin conjugate is between about 40 to 4000 mg. In some embodiments, dosages of 100 to 1000 mg of ST peptide-doxorubicin conjugate or ST peptide-daunorubicin conjugate are administered. In some embodiments, dosages of 200 to 600 mg of ST peptide-doxorubicin conjugate or ST peptide-daunorubicin conjugate are administered.

Toxin-containing conjugated compounds are formulated for intravenous administration. Using this approach, up to 6 nanomoles/kg of body weight of toxin have been administered as a single dose with marked therapeutic effects in patients with melanoma (Spitler L. E., et al. (1987) *Cancer Res.* 47:1717). In some embodiments, up to about 11 micrograms of ST peptide-toxin conjugated compound/kg of body weight may be administered for therapy.

Presuming each conjugated compound includes one molecule of ricin toxin A chain conjugated to an ST receptor binding moiety, conjugated compositions comprising ricin toxin A chain are administered in doses in which the proportion by weight of ricin toxin A chain is 1–500 $\mu$g of the total weight of the conjugated compound administered. In some preferred embodiments, conjugated compositions comprising ricin toxin A chain are administered in doses in which the proportion by weight of ricin toxin A chain is 10–100 $\mu$g of the total weight of the conjugated compound administered. In some preferred embodiments, conjugated compositions comprising ricin toxin A chain are administered in doses in which the proportion by weight of ricin toxin A chain is 2–50 $\mu$g of the total weight of the conjugated compound administered. The molecular weight of ricin toxin A chain is 32,000. Thus, a conjugated compound that contains ricin A chain linked to an ST peptide has a molecular weight of about 33,300–34,500. The range of doses of such conjugated compounds to be administered are 1 to 500 μg. In some embodiments, 10 to 100 μg of such conjugated compounds are administered. In some embodiments, 20 to 50 μg of such conjugated compounds are administered.

Presuming each conjugated compound includes one molecule of diphtheria toxin A chain conjugated to an ST receptor binding moiety, conjugated compositions comprising diphtheria toxin A chain are administered in doses in which the proportion by weight of diphtheria toxin A chain is 1–500 μg of the total weight of the conjugated compound administered. In some preferred embodiments, conjugated compositions comprising diphtheria toxin A chain are administered in doses in which the proportion by weight of diphtheria toxin A chain is 10–100 μg of the total weight of the conjugated compound administered. In some preferred embodiments, conjugated compositions comprising diphtheria toxin A chain are administered in doses in which the proportion by weight of diphtheria toxin A chain is 40–80 μg of the total weight of the conjugated compound administered. The molecular weight of diphtheria toxin A chain is 66,600. Thus, a conjugated compound that contained diphtheria A chain linked to an ST peptide has a molecular weight of about 67,900–69,100. The range of doses of such conjugated compounds to be administered tested are 1 to 500 μg. In some embodiments, 10 to 100 μg of such conjugated compounds are administered. In some embodiments, 40 to 80 μg of such conjugated compounds are administered.

Presuming each conjugated compound includes one molecule of Pseudomonas exotoxin conjugated to an ST receptor binding moiety, conjugated compositions comprising Pseudomonas exotoxin are administered in doses in which the proportion by weight of Pseudomonas exotoxin is 0.01–100 μg of the total weight of the conjugated compound administered. In some preferred embodiments, conjugated compositions comprising Pseudomonas exotoxin are administered in doses in which the proportion by weight of Pseudomonas exotoxin is 0.1–10 μg of the total weight of the conjugated compound administered. In some preferred embodiments, conjugated compositions comprising Pseudomonas exotoxin are administered in doses in which the proportion by weight of Pseudomonas exotoxin is 0.3–2.2 μg of the total weight of the conjugated compound administered. The molecular weight of Pseudomonas exotoxin is 22,000. Thus, a conjugated compound that contains Pseudomonas exotoxin linked to an ST peptide has a molecular weight of about 23,300–24,500. The range of doses of such conjugated compounds to be administered tested are 0.01 to 100 μg. In some embodiments, 0.1 to 10 μg of such conjugated compounds are administered. In some embodiments, 0.3 to 2.2 μg of such conjugated compounds are administered.

To dose conjugated compositions comprising ST receptor binding moieties linked to active moieties that are radioisotopes in pharmaceutical compositions useful as imaging agents, it is presumed that each ST receptor binding moiety is linked to one radioactive active moiety. The amount of radioisotope to be administered is dependent upon the radioisotope. Those having ordinary skill in the art can readily formulate the amount of conjugated compound to be administered based upon the specific activity and energy of a given radionuclide used as an active moiety. Typically 0.1–100 millicuries per dose of imaging agent, preferably 1–10 millicuries, most often 2–5 millicuries are administered. Thus, pharmaceutical compositions according to the present invention useful as imaging agents which comprise conjugated compositions comprising an ST receptor binding moiety and a radioactive moiety comprise 0.1–100 millicuries, in some embodiments preferably 1–10 millicuries, in some embodiments preferably 2–5 millicuries, in some embodiments more preferably 1–5 millicuries. Examples of dosages include: $^{131}$I=between about 0.1–100 millicuries per dose, in some embodiments preferably 1–10 millicuries, in some embodiments 2–5 millicuries, and in some embodiments about 4 millicuries; $^{111}$In=between about 0.1–100 millicuries per dose, in some embodiments preferably 1–10 millicuries, in some embodiments 1–5 millicuries, and in some embodiments about 2 millicuries, $^{99m}$Tc=between about 0.1–100 millicuries per dose, in some embodiments preferably 5–75 millicuries, in some embodiments 10–50 millicuries, and in some embodiments about 27 millicuries. Depending upon the specific activity of the radioactive moiety and the weight of the ST receptor binding moiety the dosage defined by weight varies. ST peptides have molecular weights of between about 1300–2500. In the pharmaceutical composition comprising an ST peptide linked to a single $^{131}$I in which the specific activity of $^{131}$I-ST peptide is about 2000 Ci/mmol, administering the dose of 0.1–100 millicuries is the equivalent of 0.1–100 μg $^{131}$I-ST peptide, administering the dose of 1–10 millicuries is the equivalent of 1–10 μg of $^{131}$I-ST peptide, administering the dose of 2–5 millicuries is equivalent to giving 2–5 μg of $^{131}$I-ST peptide and administering the dose of 1–5 millicuries is equivalent to giving 1–5 μg of $^{131}$I-ST peptide. In the pharmaceutical composition comprising an ST peptide linked to a single $^{111}$In in which the specific activity of $^{111}$In-ST peptide is about 1 Ci/mmol, administering the dose of 0.1–100 millicuries is the equivalent of 0.2–200 mg $^{111}$In-ST peptide, administering the dose of 1–10 millicuries is the equivalent of 2–20 mg of $^{111}$In-ST peptide, administering the dose of 2–5 millicuries is equivalent to giving 4–10 mg of $^{111}$In-ST peptide and administering the dose of 1–5 millicuries is equivalent to giving 2–10 mg of $^{111}$In-ST peptide.

To dose conjugated compositions comprising ST receptor binding moieties linked to active moieties that are radioisotopes in pharmaceutical compositions useful as therapeutic agents, it is presumed that each ST receptor binding moiety is linked to one radioactive active moiety. The amount of radioisotope to be administered is dependent upon the radioisotope. Those having ordinary skill in the art can readily formulate the amount of conjugated compound to be administered based upon the specific activity and energy of a given radionuclide used as an active moiety. For therapeutics that comprise $^{131}$I, between 10–1000 nM, preferably 50–500, more preferably about 300 nanomoles of $^{131}$I at the tumor, per gram of tumor, is desirable. Thus, if there is about 1 gram of tumor, and about 0.1% of the administered dose binds to the tumor, 0.5–100 mg of $^{131}$I-ST peptide conjugated compound is administered. In some embodiments, 1 to 50 mg of $^{131}$I-ST peptide conjugated compound is administered. In some embodiments, 5 to 10 mg of $^{131}$I-ST peptide conjugated compound is administered. Wessels B. W. and R. D. Rogus (1984) *Med. Phys.* 11:638 and Kwok, C. S. et al. (1985) *Med. Phys.* 12:405, both of which are incorporated herein by reference, disclose detailed dose calculations for diagnostic and therapeutic conjugates which may be used in the preparation of pharmaceutical compositions of the present invention which include radioactive conjugated compounds.

One aspect of the present invention relates to a method of treating individuals suspected of suffering from metastasized colorectal cancer. Such individuals may be treated by administering to the individual a pharmaceutical composition that comprises a pharmaceutically acceptable carrier or diluent and a conjugated compound that comprises an ST receptor binding moiety and an active moiety wherein the active moiety is a radiostable therapeutic agent. In some embodiments of the present invention, the pharmaceutical composition comprises a pharmaceutically acceptable carrier or diluent and a conjugated compound that comprises an ST receptor binding moiety and an active moiety wherein the active moiety is a radiostable active agent and the ST receptor binding moiety is a peptide. In some embodiments of the present invention, the pharmaceutical composition comprises a pharmaceutically acceptable carrier or diluent and a conjugated compound that comprises an ST receptor binding moiety and an active moiety wherein the active moiety is a radiostable active agent and the ST receptor binding moiety is selected from the group consisting of: SEQ ID NO:2, SEQ ID NO:3, SEQ ID NOS:5–56 and fragments and derivatives thereof. In some embodiments of the present invention, the pharmaceutical composition comprises a pharmaceutically acceptable carrier or diluent and a conjugated compound that comprises an ST receptor binding moiety and an active moiety wherein the active moiety is a radiostable active agent and the ST receptor binding moiety is selected from the group consisting of: SEQ ID NO:2, SEQ ID NO:3, SEQ ID NO:5, SEQ ID NO:6 and SEQ ID NO:54. In some embodiments of the present invention, the pharmaceutical composition comprises a pharmaceutically acceptable carrier or diluent and a conjugated compound that comprises an ST receptor binding moiety and an active moiety wherein the active moiety is a radiostable therapeutic agent. In some embodiments of the present invention, the pharmaceutical composition comprises a pharmaceutically acceptable carrier or diluent and a conjugated compound that comprises an ST receptor binding moiety and an active moiety wherein the active moiety is a radiostable active agent selected from the group consisting of: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, Pseudomonas exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole. In some embodiments of the present invention, the pharmaceutical composition comprises a pharmaceutically acceptable carrier or diluent and a conjugated compound that comprises an ST receptor binding moiety and an active moiety wherein the ST receptor binding moiety is selected from the group consisting of: SEQ ID NO:2, SEQ ID NO:3, SEQ ID NOS:5–56, and fragments and derivatives thereof and the active moiety is a radiostable active agent selected from the group consisting of: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, Pseudomonas exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole. In some embodiments of the present invention, the pharmaceutical composition comprises a pharmaceutically acceptable carrier or diluent and a conjugated compound that comprises an ST receptor binding moiety and an active moiety wherein the active moiety is a radiostable active agent selected from the group consisting of: methotrexate, doxorubicin, daunorubicin, cytosinarabinoside, cis-platin, vindesine, mitomycin and bleomycin, alkaline phosphatase, ricin A chain, Pseudomonas exotoxin and diphtheria toxin. In some embodiments of the present invention, the pharmaceutical composition comprises a pharmaceutically acceptable carrier or diluent and a conjugated compound that comprises an ST receptor binding moiety and an active moiety wherein the ST receptor binding moiety is selected from the group consisting of: SEQ ID NO:2, SEQ ID NO:3, SEQ ID NO:5, SEQ ID NO:6 and SEQ ID NO:54 and the active moiety is a radiostable active agent selected from the group consisting of: methotrexate, doxorubicin, daunorubicin, cytosinarabinoside, cis-platin, vindesine, mitomycin and bleomycin, alkaline phosphatase, ricin A chain, Pseudomonas exotoxin and diphtheria toxin. In some embodiments of the present invention, the pharmaceutical composition comprises a pharmaceutically acceptable carrier or diluent and a radiostable conjugated compound described in Example 1. The individual being treated may be diagnosed as having metastasized colorectal cancer or may be diagnosed as having localized colorectal cancer and may undergo the treatment proactively in the event that there is some metastasis as yet undetected. The pharmaceutical composition contains a therapeutically effective amount of the conjugated composition. A therapeutically effective amount is an amount which is effective to cause a cytotoxic or cytostatic effect on metastasized colorectal cancer cells without causing lethal side effects on the individual.

One aspect of the present invention relates to a method of treating individuals suspected of suffering from metastasized colorectal cancer. Such individuals may be treated by administering to the individual a pharmaceutical composition that comprises a pharmaceutically acceptable carrier or diluent and a conjugated compound that comprises an ST receptor binding moiety and an active moiety wherein the active moiety is radioactive. In some embodiments of the present invention, the pharmaceutical composition comprises a pharmaceutically acceptable carrier or diluent and a conjugated compound that comprises an ST receptor binding moiety and an active moiety wherein the active moiety is a radioactive and the ST receptor binding moiety is a peptide. In some embodiments of the present invention, the pharmaceutical composition comprises a pharmaceutically acceptable carrier or diluent and a conjugated compound that comprises an ST receptor binding moiety and an active moiety wherein the active moiety is a radioactive and the ST receptor binding moiety is selected from the group consisting of: SEQ ID NO:2, SEQ ID NO:3, SEQ ID NOS:5–56 and fragments and derivatives thereof. In some embodiments of the present invention, the pharmaceutical composition comprises a pharmaceutically acceptable carrier or diluent and a conjugated compound that comprises an ST receptor binding moiety and an active moiety wherein the active moiety is a radioactive and the ST receptor binding moiety is selected from the group consisting of: SEQ ID NO:2, SEQ ID NO:3, SEQ ID NO:5, SEQ ID NO:6 and SEQ ID NO:54. In some embodiments of the present invention, the pharmaceutical composition comprises a pharmaceutically acceptable carrier or diluent and a conjugated compound that comprises an ST receptor binding moiety and an active moiety wherein the active moiety is a radioactive agent selected from the group consisting of: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At , $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs $^{143}$Pr, $^{161}$Tb, $^{177}$Lu, $^{191}$Os, $^{193M}$Pt and $^{197}$Hg. In some embodiments of the present invention, the pharmaceutical composition comprises a pharmaceutically acceptable carrier or diluent and a conjugated compound that comprises an ST receptor binding moiety and an active moiety wherein the ST receptor binding moiety is selected from the group consisting of: SEQ ID NO:2, SEQ ID NO:3, SEQ ID NOS:5–56 and fragments and derivatives thereof and the active moiety is a radioactive agent selected from the group consisting of: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, $^{197}$Hg, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, $^{197}$Hg, all beta negative and/or auger emitters. In some embodiments of the present invention, the pharmaceutical composition comprises a pharmaceutically acceptable carrier or diluent and a conjugated compound that comprises an ST receptor binding moiety and an active moiety wherein the active moiety is a radioactive agent selected from the group consisting of: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr $^{161}$Tb, $^{177}$Lu, $^{191}$Os, $^{193M}$Pt and $^{197}$Hg. In some embodiments of the present invention, the pharmaceutical composition comprises a pharmaceutically acceptable carrier or diluent and a conjugated compound that comprises an ST receptor binding moiety and an active moiety wherein the ST receptor binding moiety is selected from the group consisting of: SEQ ID NO:2, SEQ ID NO:3, SEQ ID NO:5, SEQ ID NO:6 and SEQ ID NO:54 and the active moiety is a radioactive agent selected from the group consisting of: $^{47}$Sc, $^{67}$Cu, $^{90}$Y, $^{109}$Pd, $^{123}$Y, $^{125}$I, $^{131}$I, $^{186}$Re, $^{188}$Re, $^{199}$Au, $^{211}$At , $^{212}$Pb, $^{212}$B , $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt and $^{197}$Hg. In some embodiments of the present invention, the pharmaceutical composition comprises a pharmaceutically acceptable carrier or diluent and a radioactive conjugated compound described in Example 1. The individual being treated may be diagnosed as having metastasized colorectal cancer or may be diagnosed as having localized colorectal cancer and may undergo the treatment proactively in the event that there is some metastasis as yet undetected. The pharmaceutical composition contains a therapeutically effective amount of the conjugated composition. A therapeutically effective amount is an amount which is effective to cause a cytotoxic or cytostatic effect on metastasized colorectal cancer cells without causing lethal side effects on the individual.

One aspect of the present invention relates to a method of detecting metastasized colorectal cancer cells in an individual suspected of suffering from metastasized colorectal cancer by radioimaging. Such individuals may be diagnosed as suffering from metastasized colorectal cancer and the metastasized colorectal cancer cells may be detected by administering to the individual, preferably by intravenous administration, a pharmaceutical composition that comprises a pharmaceutically acceptable carrier or diluent and a conjugated compound that comprises an ST receptor binding moiety and an active moiety wherein the active moiety is a radioactive and detecting the presence of a localized accumulation or aggregation of radioactivity, indicating the presence of cells with ST receptors. In some embodiments of the present invention, the pharmaceutical composition comprises a pharmaceutically acceptable carrier or diluent and a conjugated compound that comprises an ST receptor binding moiety and an active moiety wherein the active moiety is a radioactive and the ST receptor binding moiety is a peptide. In some embodiments of the present invention, the pharmaceutical composition comprises a pharmaceutically acceptable carrier or diluent and a conjugated compound that comprises an ST receptor binding moiety and an active moiety wherein the active moiety is a radioactive and the ST receptor binding moiety is selected from the group consisting of: SEQ ID NO:2, SEQ ID NO:3, SEQ ID NOS:5–56 and fragments and derivatives thereof. In some embodiments of the present invention, the pharmaceutical composition comprises a pharmaceutically acceptable carrier or diluent and a conjugated compound that comprises an ST receptor binding moiety and an active moiety wherein the active moiety is a radioactive and the ST receptor binding moiety is selected from the group consisting of: SEQ ID NO:2, SEQ ID NO:3, SEQ ID NO:5, SEQ ID NO:6 and SEQ ID NO:54. In some embodiments of the present invention, the pharmaceutical composition comprises a pharmaceutically acceptable carrier or diluent and a conjugated compound that comprises an ST receptor binding moiety and an active moiety wherein the active moiety is a radioactive agent selected from the group consisting of: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi. In some embodiments of the present invention, the pharmaceutical composition comprises a pharmaceutically acceptable carrier or diluent and a conjugated compound that comprises an ST receptor binding moiety and an active moiety wherein the ST receptor binding moiety is selected from the group consisting of: SEQ ID NO:2, SEQ ID NO:3, SEQ ID NOS:5–56 and fragments and derivatives thereof and the active moiety is a radioactive agent selected from the group consisting of: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi. In some embodiments of the present invention, the pharmaceutical composition comprises a pharmaceutically acceptable carrier or diluent and a conjugated compound that comprises an ST receptor binding moiety and an active moiety wherein the active moiety is a radioactive agent selected from the group consisting of: $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi. In some embodiments of the present invention, the pharmaceutical composition comprises a pharmaceutically acceptable carrier or diluent and a conjugated compound that comprises an ST receptor binding moiety and an active moiety wherein the ST receptor binding moiety is selected from the group consisting of: SEQ ID NO:2, SEQ ID NO:3, SEQ ID NO:5, SEQ ID NO:6 and SEQ ID NO:54 and the active moiety is a radioactive agent selected from the group consisting of: $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi. In some embodiments of the present invention, the pharmaceutical composition comprises a pharmaceutically acceptable carrier or diluent and a radioactive conjugated compound described in Example 1. The individual being treated may be diagnosed as having metastasized colorectal cancer or may be diagnosed as having localized colorectal cancer and may undergo the treatment proactively in the event that there is some metastasis as yet undetected. The pharmaceutical composition contains a diagnostically effective amount of the conjugated composition. A diagnostically effective amount is an amount which can be detected at a site in the body where cells with ST receptors are located without causing lethal side effects on the individual.

Another aspect of the invention relates to unconjugated compositions which comprise an ST receptor binding ligand and an active agent. For example, liposomes are small vesicles composed of lipids. Drugs can be introduced into the center of these vesicles. The outer shell of these vesicles comprise an ST receptor binding ligand. *Liposomes* Volumes 1, 2 and 3 CRC Press Inc. Boca Raton Fla., which is incorporated herein by reference, disclose preparation of liposome-encapsulated active agents which include targeting agents that correspond to ST receptor ligand in the outer shell. Unconjugated compositions which comprise an ST receptor ligand in the matrix of a liposome with an active agent inside include such compostions in which the ST receptor ligand is selected from the group consisting of: SEQ ID NO:2, SEQ ID NO:3, SEQ ID NOS:5–56 and fragments and derivatives thereof and the active agent is selected from the group consisting of: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, Pseudomonas exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole.

Another aspect of the invention relates to unconjugated and conjugated compositions which comprise an ST receptor ligand used to deliver therapeutic nucleic acid molecules to cells that comprise an ST receptor such as normal cells of the intestinal tract as well as metastasized colorectal cancer cells. In some embodiments, the genetic material is delivered to metastasized tumor cells to produce an antigen that can be targeted by the immune system or to produce a protein which kills the cell or inhibits its proliferation. In some embodiments, the ST receptor ligand is used to deliver nucleic acids that encode nucleic acid molecules which replace defective endogenous genes or which encode therapeutic proteins. In some embodiments, the ST receptor ligand is thus used to deliver the active agent specifically to the cells lining the intestinal tract to treat diseases specific to this organ. According to this aspect of the invention, compositions comprise nucleic acid molecules which can replace defective genes. In some embodiments, the compositions are used in gene therapy protocols to deliver to individuals, genetic material needed and/or desired to make up for a genetic deficiency.

In some embodiments, the ST receptor ligand is combined with or incorporated into a delivery vehicle thereby converting the delivery vehicle into a specifically targeted delivery vehicle. For example, an ST receptor binding peptide may be integrated into the outer portion of a viral particle making such a virus an ST receptor-bearing cell specific virus. Similarly, the coat protein of a virus may be engineered such that it is produced as a fusion protein which includes an active ST receptor binding peptide that is exposed or otherwise accessible on the outside of the viral particle making such a virus an ST receptor-bearing cell-specific virus. In some embodiments, an ST receptor ligand may be integrated or otherwise incorporated into the liposomes wherein the ST receptor ligand is exposed or otherwise accessible on the outside of the liposome making such liposomes specifically targeted to ST receptor-bearing cells.

The active agent in the conjugated or unconjugated compositions according to this aspect of the invention is a nucleic acid molecule. The nucleic acid may be RNA or preferably DNA. In some embodiments, the nucleic acid molecule is an antisense molecule or encodes an antisense sequence whose presence in the cell inhibits production of an undesirable protein. In some embodiments, the nucleic acid molecule encodes a ribozyme whose presence in the cell inhibits production of an undesirable protein. In some embodiments, the nucleic acid molecule encodes a protein or peptide that is desirably produced in the cell. In some embodiments, the nucleic acid molecule encodes a functional copy of a gene that is defective in the targeted cell. The nucleic acid molecule is preferably operably linked to regulatory elements needed to express the coding sequence in the cell.

Liposomes are small vesicles composed of lipids. Genetic constructs which encode proteins that are desired to be expressed in ST receptor-bearing cells are introduced into the center of these vesicles. The outer shell of these vesicles comprise an ST receptor ligand, in some embodiments preferably an ST peptide. *Liposomes* Volumes 1, 2 and 3 CRC Press Inc. Boca Raton Fla., which is incorporated herein by reference, disclose preparation of liposome-encapsulated active agents which include antibodies in the outer shell. In the present invention, an ST receptor ligand such as for example an ST peptide corresponds to the antibodies in the outer shell. Unconjugated compositions which comprise an ST receptor ligand in the matrix of a liposome with an active agent inside include such compositions in which the ST receptor ligand is selected from the group consisting of: SEQ ID NO:2, SEQ ID NO:3, SEQ ID NOS:5–56 and fragments and derivatives thereof.

In one embodiment for example, cystic fibrosis, a genetic disease in which there is a mutation of a specific gene encoding a chloride transport protein which ultimately produces abnormalities of function in many systems, most notably in the respiratory and intestinal tract, is treated by gene therapy techniques using ST receptor ligands to deliver the corrective gene to cells. Current therapy has been directed at replacing the mutant gene in the respiratory system with the normal gene by targeting these genes directly to the cells lining the respiratory tract using viruses which bind only to those cells. Similarly, the normal gene is packaged in liposomes targeted on their surface with ST receptor ligands and delivered to the intestinal tract. ST receptor ligands specifically target and direct the liposomes containing the normal gene to correct the lesion for cystic fibrosis to the specific cells lining the intestinal tract, from the duodenum to the rectum. Uptake of that genetic material by those cells should result in a cure of cystic fibrosis in the intestinal tract.

In another embodiment, the delivery of normal copies of the p53 tumor suppressor gene to the intestinal tract is accomplished using ST receptor ligand to target the gene therapeutic. Mutations of the p53 tumor suppressor gene appears to play a prominent role in the development of colorectal cancer in the intestinal tract. One approach to combatting this disease is the delivery of normal copies of this gene to the intestinal tract to cells expressing mutant forms of this gene. Genetic constructs that comprise normal p53 tumor suppressor genes are incorporated into liposomes that comprise an ST receptor ligand. The composition is delivered to the intestinal tract. ST receptor binding ligands

27 specifically target and direct the liposomes containing the normal gene to correct the lesion created by mutation of p53 suppressor gene in intestinal cells.

Preparation of genetic constructs is with the skill of those having ordinary skill in the art. The present invention allows such construct to be specifically targeted by using the ST receptor ligands of the present invention. The compositions of the invention include an ST receptor ligand such as an ST peptide associated with a delivery vehicle and a gene construct which comprises a coding sequence for a protein whose production is desired in the cells of the intestinal tract linked to necessary regulatory sequences for expression in the cells. For uptake by cells of the intestinal tract, the compositions are administered orally or by enema whereby they enter the intestinal tract and contact cells which comprise ST receptors. The delivery vehicles associate with the ST receptor by virtue of the ST receptor ligand and the vehicle is internalized into the cell or the active agent/genetic construct is otherwise taken up by the cell. Once internalized, the construct can provide a therapeutic effect on the individual. One having ordinary skill in the art can readily formulate such compositions for oral or enema administration and determine the effective amount of such composition to be administered to treat the disease or disorder.

The following examples are illustrative but are not meant to be limiting of the present invention.

EXAMPLES

Example 1

The following are representative compounds according to the present invention. Whenever stated below, reference to a series of compounds is provided for efficiency and is meant to name each compound in the series including all the compounds in numerical order, such as for example "3-D1 to 3-D16" is meant to refer to compounds 3-D1, 3-D2, 3-D3, 3-D4, 3-D5, 3-D6, 3-D7, 3-D8, 3-D9, 3-D10, 3-D11, 3-D12, 3-D13, 3-D14, 3-D15 and 3-D16. Likewise, whenever stated below, reference to a series of SEQ ID NO:'s is provided for efficiency and is meant to name each SEQ ID NO: in the series including the all SEQ ID NO:'s in numerical order, such as for example SEQ ID NO:5 through SEQ ID NO:56 is meant to refer to SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55 and SEQ ID NO:56. Similarly, whenever stated below, reference to a series of compounds is provided for efficiency and is meant to name each compound in the series including the all compounds in numerical order, such as for example "5-AP to 56-AP" is meant to refer to compounds 5-AP, 6-AP, 7-AP, 8-AP, 9-AP, 10-AP, 11-AP, 12-AP, 13-AP, 14-AP, 15-AP, 16-AP, 17-AP, 18-AP, 19-AP, 20-AP, 21-AP, 22-AP, 23-AP, 24-AP, 25-AP, 26-AP, 27-AP, 28-AP, 29-AP, 30-AP, 31-AP, 32-AP, 33-AP, 34-AP, 35-AP, 36-AP, 37-AP, 38-AP, 39-AP, 40-AP, 41-AP, 42-AP, 43-AP, 44-AP, 45-AP, 46-AP, 47-AP, 48-AP, 49-AP, 50-AP, 51-AP, 52-AP, 53-AP, 54-AP, 55-AP and 56-AP.

Compound 2-D1 comprises methotrexate (amethopterin) conjugated to SEQ ID NO:2.

Compound 2-D2 comprises doxorubicin (adrimycin) conjugated to SEQ ID NO:2.

Compound 2-D3 comprises daunorubicin conjugated to SEQ ID NO:2.

Compound 2-D4 comprises cytosinarabinoside conjugated to SEQ ID NO:2.

Compound 2-D5 comprises etoposide conjugated to SEQ ID NO:2.

Compound 2-D6 comprises 5-4 fluorouracil conjugated to SEQ ID NO:2.

Compound 2-D7 comprises melphalan conjugated to SEQ ID NO:2.

Compound 2-D8 comprises chlorambucil conjugated to SEQ ID NO:2.

Compound 2-D9 comprises cyclophosphamide conjugated to SEQ ID NO:2.

Compound 2-D10 comprises cis-platinum conjugated to SEQ ID NO:2.

Compound 2-D11 comprises vindesine conjugated to SEQ ID NO:2.

Compound 2-D12 comprises mitomycin conjugated to SEQ ID NO:2.

Compound 2-D13 comprises bleomycin conjugated to SEQ ID NO:2.

Compound 2-D14 comprises purothionin conjugated to SEQ ID NO:2.

Compound 2-D15 comprises macromomycin conjugated to SEQ ID NO:2.

Compound 2-D16 comprises trenimon conjugated to SEQ ID NO:2.

Compounds 3-D1 to 3-D16 are the same as compounds 2-D1 to 2-D16, respectively, except instead of comprising SEQ ID NO:2 as the ST receptor binding moiety, compounds 3-D1 to 3-D16 each comprise SEQ ID NO:3 as the ST receptor binding moiety.

Compounds 5-D1 to 5-D16 are the same as compounds 2-D1 to 2-D16, respectively, except instead of comprising SEQ ID NO:2 as the ST receptor binding moiety, compounds 5-D1 to 5-D16 each comprise SEQ ID NO:5 as the ST receptor binding moiety.

Compounds 6-D1 to 6-D16 are the same as compounds 2-D1 to 2-D16, respectively, except instead of comprising SEQ ID NO:2 as the ST receptor binding moiety, compounds 6-D1 to 6-D16 each comprise SEQ ID NO:6 as the ST receptor binding moiety.

Compounds 7-D1 to 7-D16 are the same as compounds 2-D1 to 2-D16, respectively, except instead of comprising SEQ ID NO:2 as the ST receptor binding moiety, compounds 7-D1 to 7-D16 each comprise SEQ ID NO:7 as the ST receptor binding moiety.

Compounds 8-D1 to 8-D16 are the same as compounds 2-D1 to 2-D16, respectively, except instead of comprising SEQ ID NO:2 as the ST receptor binding moiety, compounds 8-D1 to 8-D16 each comprise SEQ ID NO:8 as the ST receptor binding moiety.

Compounds 9-D1 to 9-D16 are the same as compounds 2-D1 to 2-D16, respectively, except instead of comprising SEQ ID NO:2 as the ST receptor binding moiety, compounds 9-D1 to 9-D16 each comprise SEQ ID NO:9 as the ST receptor binding moiety.

Compounds 10-D1 to 10-D16 are the same as compounds 2-D1 to 2-D16, respectively, except instead of comprising SEQ ID NO:2 as the ST receptor binding moiety, compounds 10-D1 to 10-D16 each comprise SEQ ID NO:2 as the ST receptor binding moiety.

Compounds 12-D1 to 12-D16 are the same as compounds 2-D1 to 2-D16, respectively, except instead of comprising SEQ ID NO:2 as the ST receptor binding moiety, compounds 12-D1 to 12-D16 each comprise SEQ ID NO:11 as the ST receptor binding moiety.

Compounds 12-D1 to 12-D16 are the same as compounds 2-D1 to 2-D16, respectively, except instead of comprising SEQ ID NO:2 as the ST receptor binding moiety, compounds 12-D1 to 12-D16 each comprise SEQ ID NO:12 as the ST receptor binding moiety.

Compounds 13-D1 to 13-D16 are the same as compounds 2-D1 to 2-D16, respectively, except instead of comprising SEQ ID NO:2 as the ST receptor binding moiety, compounds 13-D1 to 13-D16 each comprise SEQ ID NO:13 as the ST receptor binding moiety.

Compounds 14-D1 to 14-D16 are the same as compounds 2-D1 to 2-D16, respectively, except instead of comprising SEQ ID NO:2 as the ST receptor binding moiety, compounds 14-D1 to 14-D16 each comprise SEQ ID NO:14 as the ST receptor binding moiety.

Compounds 15-D1 to 15-D16 are the same as compounds 2-D1 to 2-D16, respectively, except instead of comprising SEQ ID NO:2 as the ST receptor binding moiety, compounds 15-D1 to 15-D16 each comprise SEQ ID NO:15 as the ST receptor binding moiety.

Compounds 16-D1 to 16-D16 are the same as compounds 2-D1 to 2-D16, respectively, except instead of comprising SEQ ID NO:2 as the ST receptor binding moiety, compounds 16-D1 to 16-D16 each comprise SEQ ID NO:16 as the ST receptor binding moiety.

Compounds 17-D1 to 17-D16 are the same as compounds 2-D1 to 2-D16, respectively, except instead of comprising SEQ ID NO:2 as the ST receptor binding moiety, compounds 17-D1 to 17-D16 each comprise SEQ ID NO:17 as the ST receptor binding moiety.

Compounds 18-D1 to 18-D16 are the same as compounds 2-D1 to 2-D16, respectively, except instead of comprising SEQ ID NO:2 as the ST receptor binding moiety, compounds 18-D1 to 18-D16 each comprise SEQ ID NO:18 as the ST receptor binding moiety.

Compounds 19-D1 to 19-D16 are the same as compounds 2-D1 to 2-D16, respectively, except instead of comprising SEQ ID NO:2 as the ST receptor binding moiety, compounds 19-D1 to 19-D16 each comprise SEQ ID NO:19 as the ST receptor binding moiety.

Compounds 20-D1 to 20-D16 are the same as compounds 2-D1 to 2-D16, respectively, except instead of comprising SEQ ID NO:2 as the ST receptor binding moiety, compounds 20-D1 to 20-D16 each comprise SEQ ID NO:20 as the ST receptor binding moiety.

Compounds 22-D1 to 22-D16 are the same as compounds 2-D1 to 2-D16, respectively, except instead of comprising SEQ ID NO:2 as the ST receptor binding moiety, compounds 22-D1 to 22-D16 each comprise SEQ ID NO:21 as the ST receptor binding moiety.

Compounds 22-D1 to 22-D16 are the same as compounds 2-D1 to 2-D16, respectively, except instead of comprising SEQ ID NO:2 as the ST receptor binding moiety, compounds 22-D1 to 22-D16 each comprise SEQ ID NO:22 as the ST receptor binding moiety.

Compounds 23-D1 to 23-D16 are the same as compounds 2-D1 to 2-D16, respectively, except instead of comprising SEQ ID NO:2 as the ST receptor binding moiety, compounds 23-D1 to 23-D16 each comprise SEQ ID NO:23 as the ST receptor binding moiety.

Compounds 24-D1 to 24-D16 are the same as compounds 2-D1 to 2-D16, respectively, except instead of comprising SEQ ID NO:2 as the ST receptor binding moiety, compounds 24-D1 to 24-D16 each comprise SEQ ID NO:24 as the ST receptor binding moiety.

Compounds 25-D1 to 25-D16 are the same as compounds 2-D1 to 2-D16, respectively, except instead of comprising SEQ ID NO:2 as the ST receptor binding moiety, compounds 25-D1 to 25-D16 each comprise SEQ ID NO:25 as the ST receptor binding moiety.

Compounds 26-D1 to 26-D16 are the same as compounds 2-D1 to 2-D16, respectively, except instead of comprising SEQ ID NO:2 as the ST receptor binding moiety, compounds 26-D1 to 26-D16 each comprise SEQ ID NO:26 as the ST receptor binding moiety.

Compounds 27-D1 to 27-D16 are the same as compounds 2-D1 to 2-D16, respectively, except instead of comprising SEQ ID NO:2 as the ST receptor binding moiety, compounds 27-D1 to 27-D16 each comprise SEQ ID NO:27 as the ST receptor binding moiety.

Compounds 28-D1 to 28-D16 are the same as compounds 2-D1 to 2-D16, respectively, except instead of comprising SEQ ID NO:2 as the ST receptor binding moiety, compounds 28-D1 to 28-D16 each comprise SEQ ID NO:28 as the ST receptor binding moiety.

Compounds 29-D1 to 29-D16 are the same as compounds 2-D1 to 2-D16, respectively, except instead of comprising SEQ ID NO:2 as the ST receptor binding moiety, compounds 29-D1 to 29-D16 each comprise SEQ ID NO:29 as the ST receptor binding moiety.

Compounds 30-D1 to 30-D16 are the same as compounds 2-D1 to 2-D16, respectively, except instead of comprising SEQ ID NO:2 as the ST receptor binding moiety, compounds 30-D1 to 30-D16 each comprise SEQ ID NO:30 as the ST receptor binding moiety.

Compounds 32-D1 to 32-D16 are the same as compounds 2-D1 to 2-D16, respectively, except instead of comprising SEQ ID NO:2 as the ST receptor binding moiety, compounds 32-D1 to 32-D16 each comprise SEQ ID NO:31 as the ST receptor binding moiety.

Compounds 32-D1 to 32-D16 are the same as compounds 2-D1 to 2-D16, respectively, except instead of comprising SEQ ID NO:2 as the ST receptor binding moiety, compounds 32-D1 to 32-D16 each comprise SEQ ID NO:32 as the ST receptor binding moiety.

Compounds 33-D1 to 33-D16 are the same as compounds 2-D1 to 2-D16, respectively, except instead of comprising SEQ ID NO:2 as the ST receptor binding moiety, compounds 33-D1 to 33-D16 each comprise SEQ ID NO:33 as the ST receptor binding moiety.

Compounds 34-D1 to 34-D16 are the same as compounds 2-D1 to 2-D16, respectively, except instead of comprising SEQ ID NO:2 as the ST receptor binding moiety, compounds 34-D1 to 34-D16 each comprise SEQ ID NO:34 as the ST receptor binding moiety.

Compounds 35-D1 to 35-D16 are the same as compounds 2-D1 to 2-D16, respectively, except instead of comprising SEQ ID NO:2 as the ST receptor binding moiety, compounds 35-D1 to 35-D16 each comprise SEQ ID NO:35 as the ST receptor binding moiety.

Compounds 36-D1 to 36-D16 are the same as compounds 2-D1 to 2-D16, respectively, except instead of comprising SEQ ID NO:2 as the ST receptor binding moiety, compounds 36-D1 to 36-D16 each comprise SEQ ID NO:36 as the ST receptor binding moiety.

Compounds 37-D1 to 37-D16 are the same as compounds 2-D1 to 2-D16, respectively, except instead of comprising SEQ ID NO:2 as the ST receptor binding moiety, compounds 37-D1 to 37-D16 each comprise SEQ ID NO:37 as the ST receptor binding moiety.

Compounds 38-D1 to 38-D1 are the same as compounds 2-D1 to 2-D16, respectively, except instead of comprising SEQ ID NO:2 as the ST receptor binding moiety, compounds 38-D1 to 38-D16 each comprise SEQ ID NO:38 as the ST receptor binding moiety.

Compounds 39-D1 to 39-D16 are the same as compounds 2-D1 to 2-D16, respectively, except instead of comprising SEQ ID NO:2 as the ST receptor binding moiety, compounds 39-D1 to 39-D16 each comprise SEQ ID NO:39 as the ST receptor binding moiety.

Compounds 40-D1 to 40-D16 are the same as compounds 2-D1 to 2-D16, respectively, except instead of comprising SEQ ID NO:2 as the ST receptor binding moiety, compounds 40-D1 to 40-D16 each comprise SEQ ID NO:40 as the ST receptor binding moiety.

Compounds 42-D1 to 42-D16 are the same as compounds 2-D1 to 2-D16, respectively, except instead of comprising SEQ ID NO:2 as the ST receptor binding moiety, compounds 42-D1 to 42-D16 each comprise SEQ ID NO:41 as the ST receptor binding moiety.

Compounds 42-D1 to 42-D16 are the same as compounds 2-D1 to 2-D16, respectively, except instead of comprising SEQ ID NO:2 as the ST receptor binding moiety, compounds 42-D1 to 42-D16 each comprise SEQ ID NO:42 as the ST receptor binding moiety.

Compounds 43-D1 to 43-D16 are the same as compounds 2-D1 to 2-D16, respectively, except instead of comprising SEQ ID NO:2 as the ST receptor binding moiety, compounds 43-D1 to 43-D16 each comprise SEQ ID NO:43 as the ST receptor binding moiety.

Compounds 44-D1 to 44-D16 are the same as compounds 2-D1 to 2-D16, respectively, except instead of comprising SEQ ID NO:2 as the ST receptor binding moiety, compounds 44-D1 to 44-D16 each comprise SEQ ID NO:44 as the ST receptor binding moiety.

Compounds 45-D1 to 45-D16 are the same as compounds 2-D1 to 2-D16, respectively, except instead of comprising SEQ ID NO:2 as the ST receptor binding moiety, compounds 45-D1 to 45-D16 each comprise SEQ ID NO:45 as the ST receptor binding moiety.

Compounds 46-D1 to 46-D16 are the same as compounds 2-D1 to 2-D16, respectively, except instead of comprising SEQ ID NO:2 as the ST receptor binding moiety, compounds 46-D1 to 46-D16 each comprise SEQ ID NO:46 as the ST receptor binding moiety.

Compounds 47-D1 to 47-D16 are the same as compounds 2-D1 to 2-D16, respectively, except instead of comprising SEQ ID NO:2 as the ST receptor binding moiety, compounds 47-D1 to 47-D16 each comprise SEQ ID NO:47 as the ST receptor binding moiety.

Compounds 48-D1 to 48-D16 are the same as compounds 2-D1 to 2-D16, respectively, except instead of comprising SEQ ID NO:2 as the ST receptor binding moiety, compounds 48-D1 to 48-D16 each comprise SEQ ID NO:48 as the ST receptor binding moiety.

Compounds 49-D1 to 49-D16 are the same as compounds 2-D1 to 2-D16, respectively, except instead of comprising SEQ ID NO:2 as the ST receptor binding moiety, compounds 49-D1 to 49-D16 each comprise SEQ ID NO:49 as the ST receptor binding moiety.

Compounds 50-D1 to 50-D16 are the same as compounds 2-D1 to 2-D16, respectively, except instead of comprising SEQ ID NO:2 as the ST receptor binding moiety, compounds 50-D1 to 50-D16 each comprise SEQ ID NO:50 as the ST receptor binding moiety.

Compounds 51-D1 to 51-D16 are the same as compounds 2-D1 to 2-D16, respectively, except instead of comprising SEQ ID NO:2 as the ST receptor binding moiety, compounds 51-D1 to 51-D16 each comprise SEQ ID NO:51 as the ST receptor binding moiety.

Compounds 52-D1 to 52-D16 are the same as compounds 2-D1 to 2-D16, respectively, except instead of comprising SEQ ID NO:2 as the ST receptor binding moiety, compounds 52-D1 to 52-D16 each comprise SEQ ID NO:52 as the ST receptor binding moiety.

Compounds 53-D1 to 53-D16 are the same as compounds 2-D1 to 2-D16, respectively, except instead of comprising SEQ ID NO:2 as the ST receptor binding moiety, compounds 53-D1 to 53-D16 each comprise SEQ ID NO:53 as the ST receptor binding moiety.

Compounds 54-D1 to 54-D16 are the same as compounds 2-D1 to 2-D16, respectively, except instead of comprising SEQ ID NO:2 as the ST receptor binding moiety, compounds 54-D1 to 54-D16 each comprise SEQ ID NO:54 as the ST receptor binding moiety.

Compounds 55-D1 to 55-D16 are the same as compounds 2-D1 to 2-D16, respectively, except instead of comprising SEQ ID NO:2 as the ST receptor binding moiety, compounds 55-D1 to 55-D16 each comprise SEQ ID NO:55 as the ST receptor binding moiety.

Compounds 56-D1 to 56-D16 are the same as compounds 2-D1 to 2-D16, respectively, except instead of comprising SEQ ID NO:2 as the ST receptor binding moiety, compounds 56-D1 to 56-D16 each comprise SEQ ID NO:56 as the ST receptor binding moiety.

Compound 2-T1 comprises ricin conjugated to SEQ ID NO:2.

Compound 2-T2 comprises ricin A chain (ricin toxin) conjugated to SEQ ID NO:2.

Compound 2-T3 comprises Pseudomonas exotoxin (PE) conjugated to SEQ ID NO:2.

Compound 2-T4 comprises diphtheria toxin (DT), conjugated to SEQ ID NO:2.

Compound 2-T5 comprises *Clostridium perfringens* phospholipase C (PLC) conjugated to SEQ ID NO:2.

Compound 2-T6 comprises bovine pancreatic ribonuclease (BPR) conjugated to SEQ ID NO:2.

Compound 2-T7 comprises pokeweed antiviral protein (PAP) conjugated to SEQ ID NO:2.

Compound 2-T8 comprises abrin conjugated to SEQ ID NO:2.

Compound 2-T9 comprises abrin A chain (abrin toxin) conjugated to SEQ ID NO:2.

Compound 2-T10 comprises cobra venom factor (CVF) conjugated to SEQ ID NO:2.

Compound 2-T11 comprises gelonin (GEL) conjugated to SEQ ID NO:2.

Compound 2-T12 comprises saporin (SAP) conjugated to SEQ ID NO:2.

Compound 2-T13 comprises modeccin conjugated to SEQ ID NO:2.

Compound 2-T14 comprises viscumin conjugated to SEQ ID NO:2.

Compound 2-T15 comprises volkensin conjugated to SEQ ID NO:2.

Compounds 3-T1 to 3-T15 are the same as compounds 2-T1 to 2-T15, respectively, except instead of comprising SEQ ID NO:2 as the ST receptor binding moiety, compounds 3-T1 to 3-T15 each comprise SEQ ID NO:3 as the ST receptor binding moiety.

Compounds 5-T1 to 5-T15 are the same as compounds 2-T1 to 2-T15, respectively, except instead of comprising SEQ ID NO:2 as the ST receptor binding moiety, compounds 5-T1 to 5-T15 each comprise SEQ ID NO:5 as the ST receptor binding moiety.

Compounds 6-T1 to 6-T15 are the same as compounds 2-T1 to 2-T15, respectively, except instead of comprising SEQ ID NO:2 as the ST receptor binding moiety, compounds 6-T1 to 6-T15 each comprise SEQ ID NO:6 as the ST receptor binding moiety.

Compounds 7-T1 to 7-T15 are the same as compounds 2-T1 to 2-T15, respectively, except instead of comprising SEQ ID NO:2 as the ST receptor binding moiety, compounds 7-T1 to 7-T15 each comprise SEQ ID NO:7 as the ST receptor binding moiety.

Compounds 8-T1 to 8-T15 are the same as compounds 2-T1 to 2-T15, respectively, except instead of comprising SEQ ID NO:2 as the ST receptor binding moiety, compounds 8-T1 to 8-T15 each comprise SEQ ID NO:8 as the ST receptor binding moiety.

Compounds 9-T1 to 9-T15 are the same as compounds 2-T1 to 2-T15, respectively, except instead of comprising SEQ ID NO:2 as the ST receptor binding moiety, compounds 9-T1 to 9-T15 each comprise SEQ ID NO:9 as the ST receptor binding moiety.

Compounds 10-T1 to 10-T15 are the same as compounds 2-T1 to 2-T15, respectively, except instead of comprising SEQ ID NO:2 as the ST receptor binding moiety, compounds 10-T1 to 10-T15 each comprise SEQ ID NO:2 as the ST receptor binding moiety.

Compounds 11-T1 to 11-T15 are the same as compounds 2-T1 to 2-T15, respectively, except instead of comprising SEQ ID NO:2 as the ST receptor binding moiety, compounds 11-T1 to 11-T15 each comprise SEQ ID NO:11 as the ST receptor binding moiety.

Compounds 12-T1 to 12-T15 are the same as compounds 2-T1 to 2-T15, respectively, except instead of comprising SEQ ID NO:2 as the ST receptor binding moiety, compounds 12-T1 to 12-T15 each comprise SEQ ID NO:12 as the ST receptor binding moiety.

Compounds 13-T1 to 13-T15 are the same as compounds 2-T1 to 2-T15, respectively, except instead of comprising SEQ ID NO:2 as the ST receptor binding moiety, compounds 13-T1 to 13-T15 each comprise SEQ ID NO:13 as the ST receptor binding moiety.

Compounds 14-T1 to 14-T15 are the same as compounds 2-T1 to 2-T15, respectively, except instead of comprising SEQ ID NO:2 as the ST receptor binding moiety, compounds 14-T1 to 14-T15 each comprise SEQ ID NO:14 as the ST receptor binding moiety.

Compounds 15-T1 to 15-T15 are the same as compounds 2-T1 to 2-T15, respectively, except instead of comprising SEQ ID NO:2 as the ST receptor binding moiety, compounds 15-T1 to 15-T15 each comprise SEQ ID NO:15 as the ST receptor binding moiety.

Compounds 15-T1 to 15-T15 are the same as compounds 2-T1 to 2-T15, respectively, except instead of comprising SEQ ID NO:2 as the ST receptor binding moiety, compounds 15-T1 to 15-T15 each comprise SEQ ID NO:15 as the ST receptor binding moiety.

Compounds 17-T1 to 17-T15 are the same as compounds 2-T1 to 2-T15, respectively, except instead of comprising SEQ ID NO:2 as the ST receptor binding moiety, compounds 17-T1 to 17-T15 each comprise SEQ ID NO:17 as the ST receptor binding moiety.

Compounds 18-T1 to 18-T15 are the same as compounds 2-T1 to 2-T15, respectively, except instead of comprising SEQ ID NO:2 as the ST receptor binding moiety, compounds 18-T1 to 18-T15 each comprise SEQ ID NO:18 as the ST receptor binding moiety.

Compounds 19-T1 to 19-T15 are the same as compounds 2-T1 to 2-T15, respectively, except instead of comprising SEQ ID NO:2 as the ST receptor binding moiety, compounds 19-T1 to 19-T15 each comprise SEQ ID NO:19 as the ST receptor binding moiety.

Compounds 20-T1 to 20-T15 are the same as compounds 2-T1 to 2-T15, respectively, except instead of comprising SEQ ID NO:2 as the ST receptor binding moiety, compounds 20-T1 to 20-T15 each comprise SEQ ID NO:20 as the ST receptor binding moiety.

Compounds 21-T1 to 21-T15 are the same as compounds 2-T1 to 2-T15, respectively, except instead of comprising SEQ ID NO:2 as the ST receptor binding moiety, compounds 21-T1 to 21-T15 each comprise SEQ ID NO:21 as the ST receptor binding moiety.

Compounds 22-T1 to 22-T15 are the same as compounds 2-T1 to 2-T15, respectively, except instead of comprising SEQ ID NO:2 as the ST receptor binding moiety, compounds 22-T1 to 22-T15 each comprise SEQ ID NO:22 as the ST receptor binding moiety.

Compounds 23-T1 to 23-T15 are the same as compounds 2-T1 to 2-T15, respectively, except instead of comprising SEQ ID NO:2 as the ST receptor binding moiety, compounds 23-T1 to 23-T15 each comprise SEQ ID NO:23 as the ST receptor binding moiety.

Compounds 24-T1 to 24-T15 are the same as compounds 2-T1 to 2-T15, respectively, except instead of comprising SEQ ID NO:2 as the ST receptor binding moiety, compounds 24-T1 to 24-T15 each comprise SEQ ID NO:24 as the ST receptor binding moiety.

Compounds 25-T1 to 25-T15 are the same as compounds 2-T1 to 2-T15, respectively, except instead of comprising SEQ ID NO:2 as the ST receptor binding moiety, compounds 25-T1 to 25-T15 each comprise SEQ ID NO:25 as the ST receptor binding moiety.

Compounds 26-T1 to 26-T15 are the same as compounds 2-T1 to 2-T15, respectively, except instead of comprising SEQ ID NO:2 as the ST receptor binding moiety, compounds 26-T1 to 26-T15 each comprise SEQ ID NO:26 as the ST receptor binding moiety.

Compounds 27-T1 to 27-T15 are the same as compounds 2-T1 to 2-T15, respectively, except instead of comprising SEQ ID NO:2 as the ST receptor binding moiety, compounds 27-T1 to 27-T15 each comprise SEQ ID NO:27 as the ST receptor binding moiety.

Compounds 28-T1 to 28-T15 are the same as compounds 2-T1 to 2-T15, respectively, except instead of comprising SEQ ID NO:2 as the ST receptor binding moiety, compounds 28-T1 to 28-T15 each comprise SEQ ID NO:28 as the ST receptor binding moiety.

Compounds 29-T1 to 29-T15 are the same as compounds 2-T1 to 2-T15, respectively, except instead of comprising SEQ ID NO:2 as the ST receptor binding moiety, compounds 29-T1 to 29-T15 each comprise SEQ ID NO:29 as the ST receptor binding moiety.

Compounds 30-T1 to 30-T15 are the same as compounds 2-T1 to 2-T15, respectively, except instead of comprising SEQ ID NO:2 as the ST receptor binding moiety, compounds 30-T1 to 30-T15 each comprise SEQ ID NO:30 as the ST receptor binding moiety.

Compounds 31-T1 to 31-T15 are the same as compounds 2-T1 to 2-T15, respectively, except instead of comprising SEQ ID NO:2 as the ST receptor binding moiety, compounds 31-T1 to 31-T15 each comprise SEQ ID NO:31 as the ST receptor binding moiety.

Compounds 32-T1 to 32-T15 are the same as compounds 2-T1 to 2-T15, respectively, except instead of comprising SEQ ID NO:2 as the ST receptor binding moiety, compounds 32-T1 to 32-T15 each comprise SEQ ID NO:32 as the ST receptor binding moiety.

Compounds 33-T1 to 33-T15 are the same as compounds 2-T1 to 2-T15, respectively, except instead of comprising SEQ ID NO:2 as the ST receptor binding moiety, compounds 33-T1 to 33-T15 each comprise SEQ ID NO:33 as the ST receptor binding moiety.

Compounds 34-T1 to 34-T15 are the same as compounds 2-T1 to 2-T15, respectively, except instead of comprising SEQ ID NO:2 as the ST receptor binding moiety, compounds 34-T1 to 34-T15 each comprise SEQ ID NO:34 as the ST receptor binding moiety.

Compounds 35-T1 to 35-T15 are the same as compounds 2-T1 to 2-T15, respectively, except instead of comprising SEQ ID NO:2 as the ST receptor binding moiety, compounds 35-T1 to 35-T15 each comprise SEQ ID NO:35 as the ST receptor binding moiety.

Compounds 36-T1 to 36-T15 are the same as compounds 2-T1 to 2-T15, respectively, except instead of comprising SEQ ID NO:2 as the ST receptor binding moiety, compounds 36-T1 to 36-T15 each comprise SEQ ID NO:36 as the ST receptor binding moiety.

Compounds 37-T1 to 37-T15 are the same as compounds 2-T1 to 2-T15, respectively, except instead of comprising SEQ ID NO:2 as the ST receptor binding moiety, compounds 37-T1 to 37-T15 each comprise SEQ ID NO:37 as the ST receptor binding moiety.

Compounds 38-T1 to 38-T15 are the same as compounds 2-T1 to 2-T15, respectively, except instead of comprising SEQ ID NO:2 as the ST receptor binding moiety, compounds 38-T1 to 38-T15 each comprise SEQ ID NO:38 as the ST receptor binding moiety.

Compounds 39-T1 to 39-T15 are the same as compounds 2-T1 to 2-T15, respectively, except instead of comprising SEQ ID NO:2 as the ST receptor binding moiety, compounds 39-T1 to 39-T15 each comprise SEQ ID NO:39 as the ST receptor binding moiety.

Compounds 40-T1 to 40-T15 are the same as compounds 2-T1 to 2-T15, respectively, except instead of comprising SEQ ID NO:2 as the ST receptor binding moiety, compounds 40-T1 to 40-T15 each comprise SEQ ID NO:40 as the ST receptor binding moiety.

Compounds 41-T1 to 41-T15 are the same as compounds 2-T1 to 2-T15, respectively, except instead of comprising SEQ ID NO:2 as the ST receptor binding moiety, compounds 41-T1 to 41-T15 each comprise SEQ ID NO:41 as the ST receptor binding moiety.

Compounds 42-T1 to 42-T15 are the same as compounds 2-T1 to 2-T15, respectively, except instead of comprising SEQ ID NO:2 as the ST receptor binding moiety, compounds 42-T1 to 42-T15 each comprise SEQ ID NO:42 as the ST receptor binding moiety.

Compounds 43-T1 to 43-T15 are the same as compounds 2-T1 to 2-T15, respectively, except instead of comprising SEQ ID NO:2 as the ST receptor binding moiety, compounds 43-T1 to 43-T15 each comprise SEQ ID NO:43 as the ST receptor binding moiety.

Compounds 44-T1 to 44-T15 are the same as compounds 2-T1 to 2-T15, respectively, except instead of comprising SEQ ID NO:2 as the ST receptor binding moiety, compounds 44-T1 to 44-T15 each comprise SEQ ID NO:44 as the ST receptor binding moiety.

Compounds 45-T1 to 45-T15 are the same as compounds 2-T1 to 2-T15, respectively, except instead of comprising SEQ ID NO:2 as the ST receptor binding moiety, compounds 45-T1 to 45-T15 each comprise SEQ ID NO:45 as the ST receptor binding moiety.

Compounds 46-T1 to 46-T15 are the same as compounds 2-T1 to 2-T15, respectively, except instead of comprising SEQ ID NO:2 as the ST receptor binding moiety, compounds 46-T1 to 46-T15 each comprise SEQ ID NO:46 as the ST receptor binding moiety.

Compounds 47-T1 to 47-T15 are the same as compounds 2-T1 to 2-T15, respectively, except instead of comprising SEQ ID NO:2 as the ST receptor binding moiety, compounds 47-T1 to 47-T15 each comprise SEQ ID NO:47 as the ST receptor binding moiety.

Compounds 48-T1 to 48-T15 are the same as compounds 2-T1 to 2-T15, respectively, except instead of comprising SEQ ID NO:2 as the ST receptor binding moiety, compounds 48-T1 to 48-T15 each comprise SEQ ID NO:48 as the ST receptor binding moiety.

Compounds 49-T1 to 49-T15 are the same as compounds 2-T1 to 2-T15, respectively, except instead of comprising SEQ ID NO:2 as the ST receptor binding moiety, compounds 49-T1 to 49-T15 each comprise SEQ ID NO:49 as the ST receptor binding moiety.

Compounds 50-T1 to 50-T15 are the same as compounds 2-T1 to 2-T15, respectively, except instead of comprising SEQ ID NO:2 as the ST receptor binding moiety, compounds 50-T1 to 50-T15 each comprise SEQ ID NO:50 as the ST receptor binding moiety.

Compounds 51-T1 to 51-T15 are the same as compounds 2-T1 to 2-T15, respectively, except instead of comprising SEQ ID NO:2 as the ST receptor binding moiety, compounds 51-T1 to 51-T15 each comprise SEQ ID NO:51 as the ST receptor binding moiety.

Compounds 52-T1 to 52-T15 are the same as compounds 2-T1 to 2-T15, respectively, except instead of comprising SEQ ID NO:2 as the ST receptor binding moiety, compounds 52-T1 to 52-T15 each comprise SEQ ID NO:52 as the ST receptor binding moiety.

Compounds 53-T1 to 53-T15 are the same as compounds 2-T1 to 2-T15, respectively, except instead of comprising SEQ ID NO:2 as the ST receptor binding moiety, compounds 53-T1 to 53-T15 each comprise SEQ ID NO:53 as the ST receptor binding moiety.

Compounds 54-T1 to 54-T15 are the same as compounds 2-T1 to 2-T15, respectively, except instead of comprising SEQ ID NO:2 as the ST receptor binding moiety, compounds 54-T1 to 54-T15 each comprise SEQ ID NO:54 as the ST receptor binding moiety.

Compounds 55-T1 to 55-T15 are the same as compounds 2-T1 to 2-T15, respectively, except instead of comprising SEQ ID NO:2 as the ST receptor binding moiety, compounds 55-T1 to 55-T15 each comprise SEQ ID NO:55 as the ST receptor binding moiety.

Compounds 56-T1 to 56-T15 are the same as compounds 2-T1 to 2-T15, respectively, except instead of comprising SEQ ID NO:2 as the ST receptor binding moiety, compounds 56-T1 to 56-T15 each comprise SEQ ID NO:56 as the ST receptor binding moiety.

Compounds 2-AP, 3-AP and 5-AP to 56-AP refer to the 53 conjugated compounds that comprise alkaline phosphatase conjugated to SEQ ID NO:2, SEQ ID NO:3 and SEQ ID NO:5 through SEQ ID NO:56, respectively.

Compounds 2-NIZ, 3-NIZ and 5-NIZ to 56-NIZ refer to the 53 conjugated compounds that comprise nitroimidazole conjugated to SEQ ID NO:2, SEQ ID NO:3 and SEQ ID NO:5 through SEQ ID NO:56, respectively.

Compounds 2-MEZ, 3-MEZ and 5-MEZ to 56-MEZ refer to the 53 conjugated compounds that comprise metronidazole conjugated to SEQ ID NO:2, SEQ ID NO:3 and SEQ ID NO:5 through SEQ ID NO:56, respectively.

Compounds 2-MIS, 3-MIS and 5-MIS to 56-MIS refer to the 53 conjugated compounds that comprise misonidazole conjugated to SEQ ID NO:2, SEQ ID NO:3 and SEQ ID NO:5 through SEQ ID NO:56, respectively.

Compounds 2-47Sc, 3-47Sc and 5-47Sc to 56-47Sc refer to the 53 conjugated compounds that comprise $^{47}$Sc conjugated to SEQ ID NO:2, SEQ ID NO:3 AND SEQ ID NO:5 through SEQ ID NO:56, respectively.

Compounds 2-67Cu, 3-67Cu and 5-67Cu to 56-67Cu refer to the 53 conjugated compounds that comprise $^{67}$Cu conjugated to SEQ ID NO:2, SEQ ID NO:3 AND SEQ ID NO:5 through SEQ ID NO:56, respectively.

Compounds 2-90Y, 3-90Y and 5-90Y to 56-90Y refer to the 53 conjugated compounds that comprise $^{90}$Y conjugated to SEQ ID NO:2, SEQ ID NO:3 AND SEQ ID NO:5 through SEQ ID NO:56, respectively.

Compounds 2-109Pd, 3-109Pd and 5-109Pd to 56-109Pd refer to the 53 conjugated compounds that comprise $^{109}$Pd conjugated to SEQ ID NO:2, SEQ ID NO:3 AND SEQ ID NO:5 through SEQ ID NO:56, respectively.

Compounds 2-123I, 3-123I and 5-123I to 56-123I refer to the 51 conjugated compounds that comprise $^{123}$I conjugated to SEQ ID NO:2, SEQ ID NO:3 AND SEQ ID NO:5 through SEQ ID NO:56, respectively.

Compounds 2-125I, 3-125I and 5-125I to 56-125I refer to the 53 conjugated compounds that comprise $^{125}$I conjugated to SEQ ID NO:2, SEQ ID NO:3 AND SEQ ID NO:5 through SEQ ID NO:56, respectively.

Compounds 2-131I, 3-131I and 5-131I to 56-131I refer to the 53 conjugated compounds that comprise $^{131}$I conjugated to SEQ ID NO:2, SEQ ID NO:3 AND SEQ ID NO:5 through SEQ ID NO:56, respectively.

Compounds 2-132I, 3-132I and 5-132I to 56-132I refer to the 53 conjugated compounds that comprise $^{132}$I conjugated to SEQ ID NO:2, SEQ ID NO:3 AND SEQ ID NO:5 through SEQ ID NO:56, respectively.

Compounds 2-186Re, 3-186Re and 5-186Re to 56-186Re refer to the 53 conjugated compounds that comprise $^{186}$Re, conjugated to SEQ ID NO:2, SEQ ID NO:3 AND SEQ ID NO:5 through SEQ ID NO:56, respectively.

Compounds 2-188Re, 3-188Re and 5-188Re to 56-188Re refer to the 53 conjugated compounds that comprise $^{188}$Re, conjugated to SEQ ID NO:2, SEQ ID NO:3 AND SEQ ID NO:5 through SEQ ID NO:56, respectively.

Compounds 2-199Au, 3-199Au and 5-199Au to 56-199Au refer to the 53 conjugated compounds that comprise $^{199}$Au, conjugated to SEQ ID NO:2, SEQ ID NO:3 AND SEQ ID NO:5 through SEQ ID NO:56, respectively.

Compounds 2-211At, 3-211At and 5-211At to 56-211At refer to the 53 conjugated compounds that comprise $^{211}$At, conjugated to SEQ ID NO:2, SEQ ID NO:3 AND SEQ ID NO:5 through SEQ ID NO:56, respectively.

Compounds 2-212Pb, 3-212Pb and 5-212Pb to 56-212Pb refer to the 53 conjugated compounds that comprise $^{212}$Pb conjugated to SEQ ID NO:2, SEQ ID NO:3 AND SEQ ID NO:5 through SEQ ID NO:56, respectively.

Compounds 2-212Bi, 3-212Bi and 5-212Bi to 56-212Bi refer to the 53 conjugated compounds that comprise $^{212}$Bi conjugated to SEQ ID NO:2, SEQ ID NO:3 AND SEQ ID NO:5 through SEQ ID NO:56, respectively.

Compounds 2-203Pb, 3-203Pb and 5-203Pb to 56-203Pb refer to the 53 conjugated compounds that comprise $^{203}$Pb conjugated to SEQ ID NO:2, SEQ ID NO:3 AND SEQ ID NO:5 through SEQ ID NO:56, respectively.

Compounds 2-206Bi, 3-206Bi and 5-206Bi to 56-206Bi refer to the 53 conjugated compounds that comprise $^{206}$Bi conjugated to SEQ ID NO:2, SEQ ID NO:3 AND SEQ ID NO:5 through SEQ ID NO:56, respectively.

Compounds 2-32P, 3-32P and 5-32P to 56-32P refer to the 53 conjugated compounds that comprise $^{32}$P conjugated to SEQ ID NO:2, SEQ ID NO:3 AND SEQ ID NO:5 through SEQ ID NO:56, respectively.

Compounds 2-33P, 3-33P and 5-33P to 56-33P refer to the 53 conjugated compounds that comprise $^{33}$P conjugated to SEQ ID NO:2, SEQ ID NO:3 AND SEQ ID NO:5 through SEQ ID NO:56, respectively.

Compounds 2-71Ge, 3-71Ge and 5-71Ge to 56-71Ge refer to the 53 conjugated compounds that comprise $^{71}$Ge conjugated to SEQ ID NO:2, SEQ ID NO:3 AND SEQ ID NO:5 through SEQ ID NO:56, respectively.

Compounds 2-77As, 3-77As and 5-77As to 56-77As refer to the 53 conjugated compounds that comprise $^{77}$As conjugated to SEQ ID NO:2, SEQ ID NO:3 AND SEQ ID NO:5 through SEQ ID NO:56, respectively.

Compounds 2-103Pd, 3-103Pd and 5-103Pd to 56-103Pd refer to the 53 conjugated compounds that comprise $^{103}$Pd conjugated to SEQ ID NO:2, SEQ ID NO:3 AND SEQ ID NO:5 through SEQ ID NO:56, respectively.

Compounds 2-105Rh, 3-105Rh and 5-105Rh to 56-105Rh refer to the 53 conjugated compounds that comprise $^{105}$Rh conjugated to SEQ ID NO:2, SEQ ID NO:3 AND SEQ ID NO:5 through SEQ ID NO:56, respectively.

Compounds 2-111Ag, 3-111Ag and 5-111Ag to 56-4111Ag refer to the 53 conjugated compounds that comprise $^{111}$Ag conjugated to SEQ ID NO:2, SEQ ID NO:3 AND SEQ ID NO:5 through SEQ ID NO:56, respectively.

Compounds 2-119Sb, 3-119Sb and 5-119Sb to 56-119Sb refer to the 53 conjugated compounds that comprise $^{119}$Sb conjugated to SEQ ID NO:2, SEQ ID NO:3 AND SEQ ID NO:5 through SEQ ID NO:56, respectively.

Compounds 2-121Sn, 3-121-Sn and 5-121Sn to 56-121Sn refer to the 53 conjugated compounds that comprise $^{121}$Sn conjugated to SEQ ID NO:2, SEQ ID NO:3 AND SEQ ID NO:5 through SEQ ID NO:56, respectively.

Compounds 2-131Cs, 3-131Cs and 5-131Cs to 56-131Cs refer to the 53 conjugated compounds that comprise $^{131}$Cs conjugated to SEQ ID NO:2, SEQ ID NO:3 AND SEQ ID NO:5 through SEQ ID NO:56, respectively.

Compounds 2-127Cs, 3-131Cs and 5-131Cs to 56-127Cs refer to the 53 conjugated compounds that comprise $^{127}$Cs conjugated to SEQ ID NO:2, SEQ ID NO:3 AND SEQ ID NO:5 through SEQ ID NO:56, respectively.

Compounds 2-129Cs, 3-129Cs and 5-129Cs to 56-129Cs refer to the 53 conjugated compounds that comprise $^{129}$Cs conjugated to SEQ ID NO:2, SEQ ID NO:3 AND SEQ ID NO:5 through SEQ ID NO:56, respectively.

Compounds 2-143Pr, 3-143Pr and 5-143Pr to 56-143Pr refer to the 53 conjugated compounds that comprise $^{143}$Pr conjugated to SEQ ID NO:2, SEQ ID NO:3 AND SEQ ID NO:5 through SEQ ID NO:56, respectively.

Compounds 2-161Tb, 3-161Tb and 5-161Tb to 56-161Tb refer to the 53 conjugated compounds that comprise $^{161}$Tb conjugated to SEQ ID NO:2, SEQ ID NO:3 AND SEQ ID NO:5 through SEQ ID NO:56, respectively.

Compounds 2-177Lu, 3-177Lu and 5-177Lu to 56-177Lu refer to the 53 conjugated compounds that comprise $^{177}$Lu conjugated to SEQ ID NO:2, SEQ ID NO:3 AND SEQ ID NO:5 through SEQ ID NO:56, respectively.

Compounds 2-191Os, 3-191Os and 5-191Os to 56-191Os refer to the 53 conjugated compounds that comprise $^{191}$Os conjugated to SEQ ID NO:2, SEQ ID NO:3 AND SEQ ID NO:5 through SEQ ID NO:56, respectively.

Compounds 2-193mPt, 3-193mPt and 5-193mPt to 56-193mPt refer to the 53 conjugated compounds that comprise $^{193M}$Pt conjugated to SEQ ID NO:2, SEQ ID NO:3 AND SEQ ID NO:5 through SEQ ID NO:56, respectively.

Compounds 2-197Hg, 3-197Hg and 5-197Hg to 56-197Hg refer to the 53 conjugated compounds that comprise $^{197}$Hg conjugated to SEQ ID NO:2, SEQ ID NO:3 AND SEQ ID NO:5 through SEQ ID NO:56, respectively.

Compounds 2-43K, 3-43K and 5-43K to 56-43K refer to the 53 conjugated compounds that comprise $^{43}$K conjugated to SEQ ID NO:2, SEQ ID NO:3 AND SEQ ID NO:5 through SEQ ID NO:56, respectively.

Compounds 2-52Fe, 3-52Fe and 5-52Fe to 56-52Fe refer to the 53 conjugated compounds that comprise $^{52}$Fe conjugated to SEQ ID NO:2, SEQ ID NO:3 AND SEQ ID NO:5 through SEQ ID NO:56, respectively.

Compounds 2-57Co, 3-57Co and 5-57Co to 56-57Co refer to the 53 conjugated compounds that comprise $^{57}$Co conjugated to SEQ ID NO:2, SEQ ID NO:3 AND SEQ ID NO:5 through SEQ ID NO:56, respectively.

Compounds 2-67Ga, 3-67Ga and 5-67Ga to 56-67Ga refer to the 53 conjugated compounds that comprise $^{67}$Ga conjugated to SEQ ID NO:2, SEQ ID NO:3 AND SEQ ID NO:5 through SEQ ID NO:56, respectively.

Compounds 2-68Ga, 3-68Ga and 5-68Ga to 56-68Ga refer to the 53 conjugated compounds that comprise $^{68}$Ga conjugated to SEQ ID NO:2, SEQ ID NO:3 AND SEQ ID NO:5 through SEQ ID NO:56, respectively.

Compounds 2-77Br, 3-77Br and 5-77Br to 56-77Br refer to the 53 conjugated compounds that comprise $^{77}$Br conjugated to SEQ ID NO:2, SEQ ID NO:3 AND SEQ ID NO:5 through SEQ ID NO:56, respectively.

Compounds 2-81Rb, 3-81Rb and 5-81Rb to 56-81Rb refer to the 53 conjugated compounds that comprise $^{81}$Rb conjugated to SEQ ID NO:2, SEQ ID NO:3 AND SEQ ID NO:5 through SEQ ID NO:56, respectively.

Compounds 2-81mKr, 3-81mKr and 5-81mKr to 56-81mKr refer to the 53 conjugated compounds that comprise $^{81M}$Kr conjugated to SEQ ID NO:2, SEQ ID NO:3 AND SEQ ID NO:5 through SEQ ID NO:56, respectively.

Compounds 2-87mSr, 3-87mSr and 5-87mSr to 56-87mSr refer to the 53 conjugated compounds that comprise $^{87M}$Sr conjugated to SEQ ID NO:2, SEQ ID NO:3 AND SEQ ID NO:5 through SEQ ID NO:56, respectively.

Compounds 2-99mTc, 3-99mTc and 5-99mTc to 56-99mTc refer to the 53 conjugated compounds that comprise $^{99M}$Tc conjugated to SEQ ID NO:2, SEQ ID NO:3 AND SEQ ID NO:5 through SEQ ID NO:56, respectively.

Compounds 2-111In, 3-111In and 5-111In to 56-111In refer to the 53 conjugated compounds that comprise $^{111}$In conjugated to SEQ ID NO:2, SEQ ID NO:3 AND SEQ ID NO:5 through SEQ ID NO:56, respectively.

Compounds 2-113mIn, 3-113mIn and 5-113mIn to 56-113mIn refer to the 53 conjugated compounds that comprise $^{113M}$In conjugated to SEQ ID NO:2, SEQ ID NO:3 AND SEQ ID NO:5 through SEQ ID NO:56, respectively.

The compounds described in this example are combined with a pharmaceutically acceptable carrier or diluent to produce pharmaceutical compositions according to the present invention. Radiostable compounds described herein are useful in pharmaceutical compositions as therapeutics in the treatment of individuals suspected of suffering from metastasized colorectal cancer including treatment of individuals diagnosed with localized colorectal cancer as a prophylactic/therapeutic before metastasis can be readily detected. When present in therapeutically effective amounts, radioactive compounds described herein are useful in pharmaceutical compositions as therapeutic agents in the treatment of individuals suspected of suffering from metastasized colorectal cancer including treatment of individuals diagnosed with localized colorectal cancer as a prophylactic/therapeutic before metastasis can be readily detected. When present in diagnostically effective amounts, radioactive compounds described herein are useful in pharmaceutical compositions as imaging agents in the diagnosis and identification of metastasized colorectal cancer in individuals.

Example 2

One procedure for crosslinking ST receptor ligands which have a free amino group such as ST receptor binding peptides, as for example SEQ ID NO:2, SEQ ID NO:3, and SEQ ID NOS:5–56 to active agents which have a free amino group such as methotrexate, doxorubicin, daunorubicin, cytosinarabinoside, cis-platin, vindesine, mitomycin and bleomycin, or alkaline phosphatase, or protein- or peptide-based toxin employs homobifunctional succinimidyl esters, preferably with chain carbon spacers such as disuccinimidyl suberate (Pierce Co, Rockford, Ill.). This approach of amino group derivatization has been employed successfully to crosslink native ST to biotin and, ultimately, to large agarose beads of micron-scale size, preserving the function of native ST (Hughes, M., et al. (1991) *Biochem.* 30:10738; Hakki, S., et al. (1993) *Int. J. Biochem.* 25:557; Almenoff, J. S., et al. (1992) *Mol. Micro.* 8:865; each of which is incorporated herein by reference).

An ST binding ligand with the free amino group such as an ST receptor binding peptide is incubated in the presence of the chemical crosslinking agent and an active agent which have a free amino group in equimolar quantities at room temperature for 15–30 min. Incubation is terminated by separating the reactants by gel permeation chromatography by HPLC. This technique separates the conjugated compounds from free active agents and free ST binding ligands, active agent-active agent conjugates and ST binding ligand- ST binding ligand conjugates. Homogeneous preparations of conjugated through their free amino groups and with a preferred molar ratio of 1:1 are obtained. As indicated above, complexing the free amino group of an ST peptide preserves receptor binding function.

Example 3

In the event that a cleavable conjugated compound is required, the same protocol as described above may be employed utilizing 3,3'-dithiobis, (sulfosuccinimidylpropionate (SPDP); Pierce, Ill.). SPDP forms a sulfhydral group from a free amino group which may be used to conjugate a compound to another free amino group. For example, ST peptides such as SEQ ID NO:2, SEQ ID NO:3, SEQ ID NOS:5–56 are derivatized using established procedures employing N-succinimidyl-3 (2-pyridildithio)-propionate (SPDP, Pharmacia-LKB, New Jersey). The ST peptide is incubated with a 5-fold molar excess of SPDP for 30 minutes at room temperature. The ST-pyridylthiopropionate conjugate is separated from unreacted reagents by gel permeation chromatography by HPLC. An active agent with a free amino group, such as a protein-based toxin, is prepared for conjugation by reduction with dithiothreitol for 4 hours at room temperature. Reduced active agent is incubated with a 2-fold molar excess of ST receptor ligand-PDP conjugate at pH 8.0 for 36 hours at 4° C. Conjugate compound is purified from unreacted agents by gel permeation chromatography by HPLC.

This protocol for conjugation is particularly useful to conjugate ST peptides to diphtheria toxin A chains and Pseudomonas exotoxin as well as ricin toxin A chains (Magerstadt, M. *Antibody Conjugates and Malignant Disease*. (1991) CRC Press, Boca Raton, USA, pp. 110–152; Cawley, D. B. et al. (1980) *Cell* 22:563; Cumber, A. J., et al. (1985) *Meth. Enz.* 112:207; Gros, O. (1985) *J. Immunol. Meth*. 81:283; Worrell, N. R., et al. (1986) *Anti-Cancer Drug Design* 1:179; Thorpe, P. E. et al. (1987) *Cancer Res.* 47:5924, each of which is incorporated herein by reference).

Example 4

Active agents with a free amino group may be derivatized with SPDP as described above and conjugated with an ST ligand that has a free amino group and that has been modified with the succinimidyl ester of iodoacetic acid (Pierce Co., Rockford, Ill.) (Magerstadt, M. (1991) *Antibody Conjugates And Malignant Disease*, CRC Press Boca Raton; Cumber, A. J. et al. (1985) *Meth. Enz.* 112:20, which are incorporated herein by reference). Conjugation relies on the selective reaction of iodoacetyl groups introduced into the amino terminal of the ST ligand with the thiol groups introduced into the active agent. As with the above protocol, this procedure avoids homopolymer formation. However, the product is conjugated through a central thioether linkage which cannot be reduced.

Example 5

An ST receptor ligand with a free amino group and active agents with free amino groups may be conjugated through a disulfide bond using iminothiolane (Pierce, Rockford, Ill.) (Fitzgerald, D. J. P. et al. (1983) *Cell* 32:607; Magerstadt, M. (1991) *Antibody Conjugates And Malignant Disease*, CRC Press, Boca Raton; Bjorn, M. J., et al. (1985) *Cancer Res.* 45:1214; Bjorn, M. J., et al. (1986) *Cancer Res.* 46:3262, which are incorporated herein by reference). The ST receptor ligand with a free amino group is derivatized at the amino terminal with iminothiolane and the active agent is derivatized with SPDP as described above. Reacting iminothiolane-derivatized ST receptor ligand with SPDP-derivatized active agent results in conjugation by a reducible disulfide bond. In addition, iminothiolane provides the versatility to conjugate these proteins through bonds other than disulfides. Thus, derivatization of active agents with the heterobifunctional agent sulfosuccinimidyl 4-(N-maleimidomethyl) cyclohexane (Pierce, Rockford, Ill.) and reaction with iminothiolane-derivatized ST receptor ligand will conjugate these peptides without formation of disulfides.

Example 6

Conjugated compounds according to the invention which comprise an active moiety that is a therapeutic agent specifically inhibit T84 cells in vitro. The following protocols may be used to demonstrate that the conjugated compounds according to the invention which comprise an active moiety that is chemotherapeutic or toxin specifically inhibit T84 cells in vitro. Inhibition of T84 cells is assessed by determining the effects of conjugated compounds on the ability of T84 cells to incorporate $^{35}S$ -leucine into protein, $^{3}H$-thymidine into DNA, and to form colonies. The assessment of protein and DNA synthesis are classical techniques to determine the cytotoxicity of conjugated compounds in vitro. Inhibition of protein synthesis is measured because the toxins used as active moieties are specific inhibitors of this process. Therefore, these assays are the most sensitive measure of whether conjugated compounds are binding to and internalized into T84 cells. Inhibition of DNA synthesis is measured because some chemotherapeutics inhibit DNA synthesis and further, it is a cytotoxicity assay which correlates closely with the reproductive survivability of cells in culture. Cytotoxicity, or the disruption of normal cellular metabolic processes, may not always directly correlate with cell survivability. Therefore, assessment of colony formation will directly measure the ability of the experimental agents to decrease the survivability of tumor cells, which closely correlates with the impact of therapeutic agents on tumor viability in vivo. Controls include performing the same assay using the unconjugated form of the active agent and the unconjugated form of the ST receptor ligand of which the conjugated compound is comprised in place of the conjugated compound. The results obtained in the test assays and control assays are compared.

Conjugated compounds are assessed for their ability to inhibit protein and DNA synthesis in vitro and to inhibit survival and proliferation by measuring colony formation in monolayer culture by established protocols (Wilson, A. P. (1987) "Cytotoxicity and viability assays", Animal Cell Culture: A Practical Approach. Freshney, R. I., ed. pp. 183–216, IRL Press, Oxford. which is incorporated herein by reference).

To assess the ability of a conjugated compound to inhibit protein synthesis in vitro, cells are plated in 200 $\mu$l of medium at a sub-confluent density of $1–2\times10^5$ and allowed to attach to form a dividing cell monolayer over 12 hours at 37° C. Subsequently, the media is replaced with 200 $\mu$l of fresh media containing the appropriate concentration of conjugated compounds and cells incubated at 37° C. for various amounts of time. At the end of the indicated incubation period, cells is washed twice with medium and incubated at 37° C. in 0.5 ml of methionine-free medium supplemented with 0.5 $\mu$Ci of $L^{35}S$-methionine (800 Ci/mmol). After incubation for another 2 hours at 37° C., the medium is aspirated, cells washed twice with medium containing 1 mg/ml of methionine, and then precipitated in 12% ice-cold TCA. Radioactivity recovered in TCA precipitates by centrifugation is quantified by liquid scintillation spectroscopy. In these studies, cells are maintained in log growth and assays are performed using triplicate wells. Data is expressed as a percentage of protein synthesis observed in the presence of experimental agents compared to untreated cells.

To assess the ability of a conjugated compound to inhibit DNA synthesis in vitro cells are plated as a subconfluent monolayer and incubated with experimental agents as described above. At the end of the incubation period, cells are washed twice and incubated at 37° C. in medium containing 2.5 µCi of $^3$H-thymidine (5 Ci/mmol). After incubation for another hour, cells are processed with TCA, precipitates recovered, and radioactivity quantified as described above. As above, cells are maintained in log growth and assays is performed in triplicate. Data is expressed as a percentage of DNA synthesis observed in the presence of experimental agents compared to untreated cells.

To assess the ability of a conjugated compound to inhibit survival and proliferation by measuring colony formation in monolayer culture, cells are plated as a subconfluent monolayer on 25 cm$^2$ flasks and allowed to attach as described above. The medium is replaced with that containing various concentrations of experimental agents and incubated with cells for various amounts of time. At the end of the incubation, cells are recovered as a single cell suspension by trypsinization and replated to a density which will yield 100–200 colonies per 6 cm plate. Cells are permitted to grow for 7 days, then fixed in methanol, stained with 1% crystal violet, and the number of colonies quantified. Assays are performed in duplicate and data is expressed as a percentage of colony formation observed in the presence of experimental agents compared to untreated cells. Results in our laboratory have demonstrated that T84 cells can be placed into single cell suspensions utilizing trypsin (10 µg/ml) with a plating efficiency of 40% and a doubling time of 18 hours.

Example 7

Radioactive iodine such as $^{123}$I, $^{125}$I, $^{131}$I and $^{132}$I, can be added to an ST receptor binding peptide such as an ST peptide using a standard protocol well-known to those having ordinary skill in the art (Thompson, M. et al. (1985) *Analytical Biochemistry* 148:26, which is incorporated herein by reference). Radioactive iodine is conjugated directly to an ST peptide such as SEQ ID NO:2, SEQ ID NO:3 or SEQ ID NO:5 at tyrosine-5, tyrosine-4 or tyrosine-5, respectively.

Briefly, the ST peptide is produced in bacteria. For example, *E. coli* strain 431 is grown in culture and secretes ST into this culture. The culture media is then purified using routine techniques. ST can also be made by solid-phase synthesis as has been done previously, using standard techniques. (Dreyfus, L., et al. (1983) *Infec. Immun.* 42:539, which is incorporated herein by reference.

Ten micrograms of ST peptide are reacted with 2 milliCuries of radioactive INa (Amersham Corporation, Massachusetts) in the presence of Iodobeads (Bio Rad Laboratories, California) and beta-D-glucose. These are reacted for 30 min after which the products are subjected to chromatography on a Sepak reversed-phase cartridge (Millipore Corp., Massachusetts) followed by separation on a $C_{18}$reversed-phase column by HPLC using a 20–25% acetonitrile gradient. Conjugated compositions which comprise SEQ ID NO:2, SEQ ID NO:3 or SEQ ID NO:5 with the radioiodine attached to tyrosine-4 elutes at 45 min. These molecules retain full biochemical and pharmacological activity.

Example 8

$^{125}$I is conjugated directly to an ST peptide such as SEQ ID NO:13 at tyrosine-4.

SEQ ID NO:13 is produced by solid-phase synthesis as described above. Ten micrograms of SEQ ID NO:13 are reacted with 2 milliCuries of $^{125}$INa (Amersham Corporation, Massachusetts) in the presence of Iodobeads (Bio Rad Laboratories, California) and beta-D-glucose. These are reacted for 30 min after which the products are subjected to chromatography on a Sepak reversed-phase cartridge (Millipore Corp., Massachusetts) followed by separation on a $C_{18}$reversed-phase column by HPLC using a 20–25% acetonitrile gradient. $^{125}$I-SEQ ID NO:13 conjugate with the radioiodine attached to tyrosine-4 elutes at 45 min. This molecule retains full biochemical and pharmacological activity.

Dosing of radioiodine for diagnostic imaging typically requires about 4 milliCuries/patient (Steinstraber, A., et al. (1988) *J. Nucl. Med.* 29:875; Wessels, B. W. and Rogus, R. D. (1984) *Med. Phys.* 11:638; Kwok, C. S., et al. (1985) *Med. Phys.* 12:405). For proteins labeled with a specific activity of 2,000 Curies/mmol, such as ST peptide, this would require about 10 micrograms of labeled peptide injected intravenously per patient for diagnostic imaging.

Example 9

$^{131}$I is conjugated directly to an ST peptide such as SEQ ID NO:13 at tyrosine-4.

SEQ ID NO:13 is produced by solid-phase synthesis as described above. Ten micrograms of SEQ ID NO:13 are reacted with 10 milliCuries of $^{131}$INa (Amersham Corporation, Massachusetts) in the presence of Iodobeads (Bio Rad Laboratories, California) and beta-D-glucose. These are reacted for 30 min after which the products are subjected to chromatography on a Sepak reversed-phase cartridge (Millipore Corp., Massachusetts) followed by separation on a $C_{18}$reversed-phase column by HPLC using a 20–25% acetonitrile gradient. $^{131}$I-SEQ ID NO:13 conjugate with the radioiodine attached to tyrosine-4 elutes at 45 min. This molecule retains full biochemical and pharmacological activity.

Typically, for radioiodinated antibodies (MW=160,000 Da), about 150 nanomoles of protein (24 milligrams) labeled with a specific activity of 10,000 Curies/mmol are required per gram of tumor per patient (Humm, J. L. (1986) *J. Nucl. Med.* 27:1490). Thus, for proteins labeled with a specific activity of 2,000 Curies/mmol, with a molecular weight of 2,000 Da, such as ST peptide, about 3 milligrams would be required per gram of tumor per patient for intravenous infusion.

Example 10

In some embodiments, coupling of ST receptor ligands which have a free amino group, particularly ST receptor binding peptides such as ST peptides, and active agents with a free amino group such as protein-based toxins is performed by introducing a disulfide bridge between the 2 molecules. This strategy is particularly useful to conjugate ST peptides since the free amino terminal has been shown to be useful as a point of conjugation without affecting ST binding activity. This strategy is particularly useful to conjugate protein-based toxins since the free amino terminal is available on such molecules and for some conjugated compounds, most notably RTA conjugates, a disulfide bride which can be reduced to yield separate proteins has been demonstrated to be important in the construction of functional chimeras targeted by monoclonal antibodies (Magerstadt, M. (1991) *Antibody Conjugates And Malignant Disease*, CRC Press, Boca Raton; Bjorn, M. J., et al. (1985) *Cancer Res*. 45:1214; Bjorn, M. J., et al. (1986) *Cancer Res*. 46:3262; Masuho, Y., et al. (1982) *J. Biochem*. 91:1583, which are each incorporated herein by reference). While some toxins may be coupled to ST peptides using crosslinking agents which do not result in a reducible disulfide bridge between the individual components but retain functional cytotoxicity, ricin A chain toxin requires a reducible disulfide for cytotoxicity while Pseudomonas exotoxin, for example, does not.

Disulfide coupling is achieved using established procedures employing the heterobifunctional agent N-succinimidyl-3 (2-pyridyldithio)-proportionate (SPDP, Pharmacia-LKB, Piscataway, N.J.) (Magerstadt, M. (1991) *Antibody Conjugates And Malignant Disease*, CRC Press, Boca Raton; Cawley, D. B. et al. (1980) *Cell* 22:563; Cumber, A. J., et al. (1985) *Meth. Enz*. 112:20; Gros, O., et al. (1985) *J. Immunol. Meth*. 81:283; Worrell, N. R., (1986) *Anti-Cancer Drug Design* 1:19; Thorpe, P. E., et al. (1987) *Cancer Res*. 4:5924, which are incorporated herein by reference).

In some embodiments, toxins including the A chains of deglycosylated ricin toxin (RTA; Sigma Chemical Co., St. Louis, Mo.), diphtheria toxin A (DTA; Calbiochem, La Jolla, Calif.) and Pseudomonas exotoxin (PEA) are conjugated to ST peptides to produce conjugated compositions according to the present invention using this procedure. Deglycosylated RTA is employed since the glycosylated form of this toxin exhibits non-specific binding to liver cells. DTA is prepared from diphtheria toxin by an established procedure (Michel, A. and Drykx, J. (1975) *Biochem. Biophys. Acta* 365:15; Cumber, A. J., et al. (1985) *Meth. Enz*. 112:207, both of which are incorporated herein by reference). PEA In some embodiments, ST peptides are conjugated to toxins by this procedure. For example, the ST peptide SEQ ID NO:3 which is produced as described above (see Dreyfus, L., et al. (1983) *Infec. Immun*. 42:539, which is incorporated herein by reference).

Toxins are prepared for coupling by reduction with 0.1M dithiothreitol (DTT) for 4 hours at room temperature in 0.4M Tris-HCl, pH 8.0 and 1 mM EDTA. Reduced toxins are desalted on a Sephadex G-25 column equilibrated in TES buffer and mixed with a 2-fold molar excess of ST-PDP. Reactions are adjusted to pH 8.0 with TES and incubated at 4° C. for 36 hours. ST peptide-toxin conjugates are purified from unreacted products and homopolymers of ST peptides and toxins by gel filtration on Sephadex G-75 in 20 mM TES, pH 8.0 containing 0.1M NaCl. Chromatographic fractions are monitored by SDS-PAGE on 10% polyacrylamide gels under non-reducing conditions for the presence of 1:1 conjugates of ST peptides and toxins. Also, these conjugates are analyzed by 10% SDS-PAGE under reducing conditions, to insure that ST and cytotoxins are coupled by a reducible disulfide bond. Molar concentrations of the conjugate are calculated by quantifying radioactivity in these samples.

ST trace labeled with $^{125}I$ on tyrosine 4 (10 Ci/mmol) is used in order to follow the conjugate through various separation and chromatographic steps and to enable us to calculate the molar ratio of ST to cytotoxin in the final purified conjugate. ST trace labeled with $^{125}I$ is derivatized by incubating 1 mg/ml with a 5-fold molar excess of SPDP for 30 min at room temperature in Na phosphate buffer, pH 7.4. The ST-pyridylthiopropionate (ST-PDP) conjugate is purified from unreacted crosslinking agent by chromatography on Sephadex G-25 equilibrated with 20 mM N-Tris (hydroxymethyl)-methyl-2-aminoethane sulfonic acid (TES) buffer, pH 7.4. Preservation of receptor binding of conjugated ST peptides in human intestinal membranes is determined in competition assays of increasing concentrations of ST-PDP and $^{125}I$-ST ($5\times10^{10}$M), to insure that this process does not destroy the function of the ST receptor ligand.

The above coupling protocol has several advantages for conjugating the various toxins. First, it introduces a reducible disulfide bridge into the conjugated composition, important for RTA cytotoxicity. Also, this technique avoids the exposure of ST peptide to quantitative reduction with DTT which could interrupt its 3 intrachain disulfide bonds important for receptor binding activity. In addition, there is a single group available at the amino terminal of ST peptide for derivatization with SPDP and previous experiments have demonstrated that derivatization of that group preserves the binding properties of the ligand. Therefore, other configurations for conjugation which could result in inactivation of ST are not possible. Furthermore, PEA requires preactivation with DTT to achieve optimum cytotoxicity which will be accomplished utilizing the above protocol.

To produce a functional conjugated compound that comprises a toxin, it is essential that the receptor binding and enzyme activities of the moieties are preserved throughout the process of conjugation. Therefore, once such conjugate compounds are obtained, they are tested for the preservation of those functions. ST receptor binding activity of conjugated compounds is examined in competitive binding assays, as described above. In these studies, increasing concentrations of the conjugated compounds are incubated with a constant concentration ($5\times10^{10}$M) of $^{125}I$-ST and intestinal membranes (50–100 μg of protein) to achieve equilibrium. Parallel incubations contain excess ($5\times10^{7}$M) unlabeled ST to assess non-specific binding. The concentration-dependent competitive displacement of radiolabeled ST by conjugated compounds is compared to the competitive displacement achieved by native ST. Displacement curves are employed to estimate the affinity of each conjugated compound ($K_D$) and compare that to the affinity of native ST measured by this technique. Control studies include evaluating the ability of unconjugated toxins to compete with native ST for receptor binding. These studies establish that the binding function of ST in the conjugated construct is preserved.

Preservation of toxin activity in conjugated compounds is also assessed. PEA and DTA induce toxicity by catalyzing the NAD-dependent ADP-ribosylation of elongation factor 2 (EF2), inhibiting protein synthesis. ADP-ribosyl transferase activity is assessed using an established assay (Chung, D. W. and Collier, R. J. *Infect. Immun*. 16:832; Fitzgerald, D. J. P. (1987) *Meth. Enz*. 151:139, which are both incorporated herein by reference). Reactions are conducted in 30 Mm Tris-HCl, pH 8.2 containing 40 mM DTT, 50 mCi $^{14}C$-NAD, and 20 μl of rabbit reticulocyte lysate containing elongation factor 2 (EF-2; Promega, Madison, Wis.) in a total volume of 500 μl. Reactions are initiated by the addition of lysate, incubated for 30 minutes at 37° C., and terminated by the addition of ice-cold 12% TCA. Radioactivity in protein precipitates collected by centrifugation is quantified by liquid scintillation spectroscopy. The ability of the conjugated compounds that comprise DTA or PEA to catalyze the transfer of labeled ADP-ribose to EF-2 is compared to that catalyzed by similar quantities of unconjugated toxins. Control experiments include examining the ability of unconjugated toxins or ST to catalyze ADP-ribose transfer and the effects of ST on the enzymatic activity of unconjugated cytotoxins.

RTA inhibits protein synthesis by catalytically inactivating the 60S ribosomal subunit. The catalytic activity of conjugated compounds that comprise RTA is assessed by its ability to inhibit protein synthesis in cell-free assays using established procedures (Leonard, J. E. et al. (1985) *Cancer Res.* 45:5263 which is incorporated herein by reference). Assays contain 35 μl of nuclease-treated rabbit reticulocyte lysates, 1 μl of 1 mM mixed amino acids deficient in methionine, 2 μl of Brome mosaic RNA (Promega, Madison, Wis.) at 0.5 μg/μl, 7 μl of sterile water or conjugate solution, and 5 μCi of $^{35}$S-methionine in a total volume of 50 μl. Reactions will be initiated by the addition of lysate, incubated at 30° C. for 30 minutes, and terminated by the use of addition of 12% TCA. Radioactivity in protein precipitates collected by centrifugation is quantified by liquid scintillation spectroscopy. Control experiments include examining the ability of unconjugated RTA or ST peptide to inhibit cell-free protein synthesis and the effects of ST peptide on the inhibitory activity of the unconjugated cytotoxin.

Example 11

Methotrexate is linked to SEQ ID NO:12 by the homobifunctional crosslinker succinimidyl esters with long chain carbon spacers such as disuccinimidyl suberate (Pierce, Ill.). SEQ ID NO:12 is incubated in the presence of the chemical crosslinking agent and methotrexate in equimolar quantities at room temperature for 15–30 min. Incubation is terminated by separating the reactants by gel permeation chromatography by HPLC. This technique separates the methotrexate/SEQ ID NO:12 conjugates from free drug, free ST peptide, drug-drug conjugates and ST peptide-ST peptide conjugates. Homogeneous preparations of SEQ ID NO:12-methotrexate conjugates coupled through their free amino groups and with a preferred molar ratio of 1:1 are obtained. Complexing the free amino group of ST preserves receptor binding function.

Example 12

$^{111}$In is coupled to SEQ ID NO:37 with functional amino groups using a chelator. The ST peptide has a free amino function at the amino terminal which may be modified without altering the ST receptor binding activity of the ST peptide. $^{111}$In is rapidly and potently chelated by either EDTA (ethylenediaminetetraacetic acid) or DTPA (diethylenetriaminepetaacetic acid). DTPA is preferred over EDTA because the latter may be more unstable in vivo. The $^{111}$In-DTPA is converted to a mixed N-hydroxysuccinimide ester which is reactive with free amino groups, mixed with ST, and the reaction products, including $^{111}$In-SEQ ID NO:37 separated by HPLC (Bremer, K. H. and Schwarz, A. (1987) in *Safety And Efficacy Of Radiopharmaceuticals*. Kristensen, K. and Norbygaard, E., Eds. Martinius Nijhoff, Dordrecht, The Netherlands, P. 43; Krejcarek, G. E., and Tucker, K. L. (1977) *Biochem. Biophys. Res. Commun.* 77:581; Paxton, R. J., et al. (1985) *Cancer Res.* 45:5694; Richardson, A. P., et al. (1986) *Nucl. Med. Biol.* 14:569, which are each incorporated herein by reference).

Example 13

$^{99m}$Tc can be conjugated to SEQ ID NO:46 using an approach which is similar to that for indium. Thus, technetium can be chelated by DTPA which is converted to an anhydride, such as N-hydroxysuccinimide anhydride, and reacted with SEQ ID NO:46. The ST-technetium conjugate can then be separated using HPLC (Magerstadt, M. (1991) *Antibody Conjugates And Malignant Disease* CRC Press, Boca Raton; Eckelman, W. C. and Paik, C. H. (1986) *Nucl. Med. Biol.* 14:569)

Example 14

Diphtheria toxin A chain (DTA) is prepared from native diphtheria toxin by standard techniques. SEQ ID NO:22 is coupled to N-succinimidyl-3(2-pyridyldithio)-propionate (SPDP, Pharmacia-LKB, Piscataway, N.J.) and the SEQ ID NO:22-PDP conjugate is purified by HPLC by established procedures. DTA is reduced with dithiothreitol and incubated with SEQ ID NO:22 PDP. DTA-SEQ ID NO:22 is purified after conjugation using HPLC.

Example 15

Pseudomonas Exotoxin is prepared from native sources by standard techniques. SEQ ID NO:54 is coupled to N-succinimidyl-3(2-pyridyldithio)-propionate (SPDP, Pharmacia-LKB, Piscataway, N.J.) and the SEQ ID NO:54-PDP conjugate is purified by HPLC by established procedures. Pseudomonas Exotoxin is reduced with dithiothreitol and incubated with SEQ ID NO:54-PDP. Pseudomonas Exotoxin-SEQ ID NO:54 is purified after conjugation using HPLC.

Example 16

Doxorubicin is linked to SEQ ID NO:54 by the homobifunctional crosslinker succinimidyl esters with long chain carbon spacers such as disuccinimidyl suberate (Pierce, Ill.). SEQ ID NO:54 is incubated in the presence of the chemical crosslinking agent and doxorubicin in equimolar quantities at room temperature for 15–30 min. Incubation is terminated by separating the reactants by gel permeation chromatography by HPLC. This technique separates the doxorubicin/SEQ ID NO:54 conjugates from free doxorubicin, free ST peptide, drug-drug conjugates and ST peptide-ST peptide conjugates. Homogeneous preparations of SEQ ID NO:54-doxorubicin conjugates coupled through their free amino groups and with a preferred molar ratio of 1:1 are obtained. Complexing the free amino group of ST preserves receptor binding function.

Example 17

Daunorubicin is linked to SEQ ID NO:32 by the homobifunctional crosslinker succinimidyl esters with long chain carbon spacers such as disuccinimidyl suberate (Pierce, Ill.). SEQ ID NO:32 is incubated in the presence of the chemical crosslinking agent and daunorubicin in equimolar quantities at room temperature for 15–30 min. Incubation is terminated by separating the reactants by gel permeation chromatography by HPLC. This technique separates the daunorubicin/SEQ ID NO:54 conjugates from free daunorubicin, free ST peptide, drug-drug conjugates and ST peptide-ST peptide conjugates. Homogeneous preparations of SEQ ID NO:54-daunorubicin conjugates coupled through their free amino groups and with a preferred molar ratio of 1:1 are obtained. Complexing the free amino group of ST preserves receptor binding function.

Example 18

As stated above, an ST receptor binding moiety is an ST receptor ligand that may be a peptide or a non-peptide. In addition to the peptides described above, other peptides may be identified by those having ordinary skill in the art using well known technology. Similarly, non-peptide ST receptor ligands may be identified using well known technology.

Over the past 10 years, it has become recognized that the specific high-affinity interaction of a receptor and its ligand, for example ST receptor and ST, has its basis in the 3-dimensional conformational space of the ligand and the complimentary 3-dimensional configuration of the region of the receptor molecule involved in ligand binding (the receptor boding pocket). In addition, it has become recognized that various arrays of naturally-occurring amino acids, non-natural amino acids, and organic molecules can be organized in configurations that are unrelated to the natural ligands in their linear structure, but resemble the 3-dimensional structure of the natural ligands in conformational space and, thus, are recognized by receptors with high affinity and specificity. Furthermore, techniques have been described in the literature that permit one of ordinary skill in the art to generate large libraries of these arrays of natural amino acids, non-natural amino acids and organic compounds to prospectively identify individual compounds that interact with receptors with high affinity and specificity which are unrelated to the native ligand of that receptor. Thus, it is a relatively straightforward task for one of ordinary skill in the art to identify arrays of naturally occurring amino acids, non-natural amino acids, or organic compounds which can bind specifically and tightly to the ST receptor, which bear no structural relationship to ST, guanylin or uroguanylin.

To identify ST receptor ligands that are peptides, those having ordinary skill in the art, can use any of the well known methodologies for screening random peptide libraries in order to identify peptides which bind to the ST receptor. In the most basic of methodologies, the peptides which bind to the target are isolated and sequenced. In some methodologies, each random peptide is linked to a nucleic acid molecule which includes the coding sequence for that particular random peptide. The random peptides, each with an attached coding sequence, are contacted with the ST receptor and the peptides which are unbound to the ST receptor are removed. The nucleic acid molecule which includes the coding sequence of the peptide that binds to the ST receptor can then be used to determine the amino acid sequence of the peptide as well as produce large quantities of the peptide. It is also possible to produce peptide libraries on solid supports where the spatial location on the support corresponds to a specific synthesis and therefore specific peptide. Such methods often use photolithography-like steps to create diverse peptide libraries on solid supports in which the spatial address on the support allows for the determination of the sequence.

The production of organic compound libraries on solid supports may also be used to produce combinatorial libraries of non-peptide compounds such as oligonucleotides and sugars, for example. As in the case of peptide libraries on solid supports, the spatial location on the support corresponds to a specific synthesis and therefore specific compound. Such methods often use photolithography-like steps to create diverse compound libraries on solid supports in which the spatial address on the support allows for the determination of the synthesis scheme which produced the compound. Once the synthesis scheme is identified, the structure of the compound can become known.

Gallop et al. 1994 J. Medicinal Chemistry 37:1233, which is incorporated herein by reference, provides a review of several of the various methodologies of screening random peptide libraries and identifying peptides from such libraries which bind to target proteins. Following these teachings, ST receptor ligands that are peptides and that are useful as ST receptor binding moieties may be identified by those having ordinary skill in the art.

Peptides and proteins displayed on phage particles are described in Gallop et al. Supra. Random arrays of nucleic acids can be inserted into genes encoding surface proteins of bacteriophage which are employed to infect bacteria, yielding phage expressing the peptides encoded by the random array of nucleotides on their surface. These phage displaying the peptide can be employed to determine whether those peptides can bind to specific proteins, receptors, antibodies, etc. The identity of the peptide can be determined by sequencing the recombinant DNA from the phage expressing the peptide. This approach has the potential to yield vast arrays of peptides in a library (up to $10^9$ unique peptides). This technique has been employed to identify novel binding peptides to the fibrinogen receptor on platelets, which bear no sequence homology to the natural occurring ligands of this receptor (Smith et al., 1993 Gene 128:37, which is incorporated herein by reference). Similarly, this technique has been applied to identify peptides which bind to the MHC class II receptor (Hammer et al., 1993 Cell 74:197, which is incorporated herein by reference) and the chaperonin receptor (Blond-Elguindi et al., 1993 Cell 75:717, which is incorporated herein by reference).

Peptides displayed on plasmids are described in Gallop et al. Supra. In this approach, the random oligonucleotides which encode the library of peptides can be expressed on a specific plasmid whose expression is under the control of a specific promoter, such as the lac operon. The peptides are expressed as fusion proteins coupled to the Lac I protein, under the control of the lac operon. The fusion protein specifically binds to the lac operator on the plasmid and so the random peptide is associated with the specific DNA element that encodes it. In this way, the sequence of the peptide can be deduced, by PCR of the DNA associated with the fusion protein. These proteins can be screened in solution phase to determine whether they bind to specific receptors. Employing this approach, novel substrates have been identified for specific enzymes (Schatz 1993).

A variation of the above technique, also described in Gallop et al. Supra, can be employed in which random oligonucleotides encoding peptide libraries on plasmids can be expressed in cell-free systems. In this approach, a molecular DNA library can be constructed containing the random array of oligonucleotides, which are then expressed in a bacterial in vitro transcription/translation system. The identity of the ligand is determined by purifying the complex of nascent chain peptide/polysome containing the mRNA of interest on affinity resins composed of the receptor and then sequencing following amplification with RT-PCR. Employing this technique permits generation of large libraries (up to $10^{11}$ recombinants). Peptides which recognize antibodies specifically directed to dynorphin have been identified employing this technique (Cull et al., 1992 Proc. Natl. Acad. Sci. USA 89:1865, which is incorporated herein by reference).

Libraries of peptides can be generated for screening against a receptor by chemical synthesis. For example, simultaneous preparation of large numbers of diverse peptides have been generated employing the approach of multiple peptide synthesis as described in Gallop et al. Supra. In one application, random peptides are generated by standard solid-phase Merrifield synthesis on polyacrylamide microtiter plates (multipin synthesis) which are subsequently screened for their ability to compete with receptor binding in a standard competitive binding assay (Wang et al., 1993 *Bioorg. Med. Chem. Lett.* 3:447, which is incorporated herein by reference). Indeed, this approach has been employed to identify novel binding peptides to the substance P receptor (Wang et al. Supra). Similarly, peptide libraries can be constructed by multiple peptide synthesis employing the "tea bag" method in which bags of solid support resin are sequentially incubated with various amino acids to generate arrays of different peptides (Gallop et al. Supra). Employing this approach, peptides which bind to the integrin receptor (Ruggeri et al., 1986 *Proc. Natl. Acad. Sci. USA* 83:5708, which is incorporated herein by reference) and the neuropeptide Y receptor (Beck-Sickinger et al., 1990 *Int. J. Peptide Protein Res.* 36:522, which is incorporated herein by reference) have been identified.

In general, the generation and utility of combinatorial libraries depend on (1) a method to generate diverse arrays of building blocks, (2) a method for identifying members of the array that yield the desired function, and (3) a method for deconvoluting the structure of that member. Several approaches to these constraints have been defined.

The following is a description of methods of library generation which can be used in procedures for identifying ST receptor ligands according to the invention.

Modifications of the above approaches can be employed to generate libraries of vast molecular diversity by connecting together members of a set of chemical building blocks, such as amino acids, in all possible combinations (Gallop et al. Supra) In one approach, mixtures of activated monomers are coupled to a growing chain of amino acids on a solid support at each cycle. This is a multivalent synthetic system.

Also, split synthesis involves incubating the growing chain in individual reactions containing only a single building block (Gallop et al. Supra). Following attachment, resin from all the reactions are mixed and apportioned into individual reactions for the next step of coupling. These approaches yield a stochastic collection of $n^x$ different peptides for screening, where n is the number of building blocks and x is the number of cycles of reaction.

Alternatively, arrays of molecules can be generated in which one or more positions contain known amino acids, while the remainder are random (Gallop et al. Supra). These yield a limited library which is screened for members with the desired activity. These members are identified, their structure determined, and the structure regenerated with another position containing defined amino acids and screened. This iterative approach ultimately yields peptides which are optimal for recognizing the conformational binding pocket of a receptor.

In addition, arrays are not limited to amino acids forming peptides, but can be extended to linear and nonlinear arrays of organic molecules (Gordon et al., 1994 *J. Medicinal Chemistry* 37:1385, which is incorporated herein by reference). Indeed, employing this approach of generating libraries of randomly arrayed inorganic building blocks, ligands which bound to 7-transmembrane receptors were identified (Zuckermann et al., 1994 *J. Med. Chem.* 37:2678, which is incorporated herein by reference).

Libraries are currently being constructed which can be modified after synthesis to alter the chemical side groups and bonds, to give "designer" arrays to test for their interaction with receptors (Osteresh et al., 1994 *Proc. Natl. Acad. Sci. USA* 91:11138, which is incorporated herein by reference). This technique, generating "libraries from libraries", was applied to the permethylation of a peptide library which yielded compounds with selective antimicrobial activity against gram positive bacteria.

Libraries are also being constructed to express arrays of pharmacological motifs, rather than specific structural arrays of amino acids (Sepetov et al., 1995 *Proc. Natl. Acad. Sci. USA* 92:5426, which is incorporated herein by reference). This technique seeks to identify structural motifs that have specific affinities for receptors, which can be modified in further refinements employing libraries to define structure-activity relationships. Employing this approach of searching motif libraries, generating "libraries of libraries", reduces the number of component members required for screening in the early phase of library examination.

The following is a description of methods of identifying ST receptor ligands according to the invention from libraries of randomly generated molecules.

Components in the library which interact with receptors may be identified by their binding to receptors immobilized on solid support (Gordon et al. Supra).

They may also be identified by their ability to compete with native ligand for binding to cognate receptors in solution phase (Gordon et al. Supra).

Components may be identified by their binding to soluble receptors when those components are immobilized on solid supports (Gordon et al. Supra).

Once a member of a library which binds receptors has been identified, the structure of that member must be deconvoluted (deduced) in order to identify the structure and generate large quantities to work with, or develop further analogs to study structure-activity relationships. The following is a description of methods of deconvolution for deducing the structure of molecules identified as potential ST receptor ligands according to the invention.

Peptide libraries may be expressed on the surface of bacteriophage particles (Gallop et al. Supra). Once the peptide interacting with the receptor has been identified, its structure can be deduced by isolating the DNA from the phage and determining its sequence by PCR.

Libraries expressed on plasmids, under the control of the Lac operon can be deconvoluted since these peptides are fused with the lac I protein which specifically interacts with the lac operon on the plasmid encoding the peptide (Gallop et al. Supra) The structure can be deduced by isolating that plasmid attached to the lac I protein and deducing the nucleotide and peptide sequence by PCR.

Libraries expressed on plasmids can also be expressed in cell-free systems employing transcription/translation systems (Gallop et al. Supra). In this paradigm, the protein interacting with receptors is isolated with its attached ribosome and mRNA. The sequence of the peptide is deduced by RT-PCR of the associated mRNA.

Library construction can be coupled with photolithography, so that the structure of any member of the library can be deduced by determining its position within the substrate array (Gallop et al. Supra). This technique is termed positional addressability, since the structural information can be deduced by the precise position of the member.

Members of a library can also be identified by tagging the library with identifiable arrays of other molecules (Ohlmeyer et al., 1993 *Proc. Natl. Acad. Sci. USA* 90:10922, which is incorporated herein by reference, and Gallop et al. Supra). This technique is a modification of associating the peptide with the plasmid of phage encoding the sequence, described above. Some methods employ arrays of nucleotides to encode the sequential synthetic history of the peptide. Thus, nucleotides are attached to the growing peptide sequentially, and can be decoded by PCR to yield the structure of the associated peptide. Alternatively, arrays of small organic molecules can be employed as sequencable tags which encode the sequential synthetic history of the peptide. Thus, nucleotides are attached to the growing peptide sequentially, and can be decoded by PCR to yield the structure of the associatec peptide. Alternatively, arrays of small organic molecules can be employed as sequencable tags which encode the sequential synthetic history of the library member.

Finally, the structure of a member of the library can be directly determined by amino acid sequence analysis.

The following patents, which are each incorporated herein by reference, describe methods of making random peptide or non-peptide libraries and screening such libraries to identify compounds that bind to target proteins. As used in the present invention, ST receptors can be the targets used to identify the peptide and non-peptide ligands generated and screened as disclosed in the patents.

U.S. Pat. No. 5,270,170 issued to Schatz et al. on Dec. 14, 1993, and U.S. Pat. No. 5,338,665 issued to Schatz et al. on Aug. 16, 1994, which are both incorporated herein by reference, refer to peptide libraries and screening methods which can be used to identify ST receptor ligands according to the invention.

U.S. Pat. No. 5,395,750 issued to Dillon et al. on Mar. 7, 1995, which is incorporated herein by reference, refers to methods of producing proteins which bind to predetermined antigens. Such methods can be used to produce ST receptor ligands according to the invention.

U.S. Pat. No. 5,223,409 issued to Ladner et al. on Jun. 29, 1993, which is incorporated herein by reference, refers to the directed evolution to novel binding proteins. Such proteins may be produced and screened as disclosed therein to identify ST receptor ligands according to the invention.

U.S. Pat. No. 5,366,862 issued to Venton et al. on Nov. 22, 1994, which is incorporated herein by reference, refers to methods for generating and screening useful peptides. The methods herein described can be used to identify ST receptor ligands according to the invention.

U.S. Pat. No. 5,340,474 issued to Kauvar on Aug. 23, 1994 as well as U.S. Pat. No. 5,133,866, U.S. Pat. No. 4,963,263 and U.S. Pat. No. 5,217,869, which are each incorporated herein by reference, can be used to identify ST receptor ligands according to the invention.

U.S. Pat. No. 5,405,783 issued to Pirrung et al. on Apr. 11, 1995, which is incorporated herein by reference, refers to large scale photolithographic solid phase synthesis of an array of polymers. The teachings therein can be used to identify ST receptor ligands according to the invention.

U.S. Pat. No. 5,143,854 issued to Pirrung et al. on Sep. 1, 1992, which is incorporated herein by reference, refers to a large scale photolithographic solid phase synthesis of polypeptides and receptor binding screening thereof.

U.S. Pat. No. 5,384,261 issued to Winkler et al. on Jan. 24, 1995, which is incorporated herein by reference, refers to very large scale immobilized polymer synthesis using mechanically directed flow patterns. Such methods are useful to identify ST receptor ligands according to the invention.

U.S. Pat. No. 5,221,736 issued to Coolidge et al. on Jun. 22, 1993, which is incorporated herein by reference, refers to sequential peptide and oligonucleotide synthesis using immunoaffinity techniques. Such techniques may be used to identify ST receptor ligands according to the invention.

U.S. Pat. No. 5,412,087 issued to McGall et al. on May 2, 1995, which is incorporated herein by reference, refers to spatially addressable immobilization of oligonucleotides and other biological polymers on surfaces. Such methods may be used to identify ST receptor ligands according to the invention.

U.S. Pat. No. 5,324,483 issued to Cody et al. on Jun. 28, 1994, which is incorporated herein by reference, refers to apparatus for multiple simultaneous synthesis. The apparatus and method disclosed therein may be used to produce multiple compounds which can be screened to identify ST receptor ligands according to the invention.

U.S. Pat. No. 5,252,743 issued to Barrett et al. on Oct. 12, 1993, which is incorporated herein by reference, refers to spatially addressable immobilization of anti-ligands on surfaces. The methods and compositions described therein may be used to identify ST receptor ligands according to the invention.

U.S. Pat. No. 5,424,186 issued to Foder et al. on Jun. 13, 1995, which is incorporated herein by reference, refers to a very large scale immobilized polymer synthesis. The method of synthesizing oligonucleotides described therein may be used to identify ST receptor ligands according to the invention.

U.S. Pat. No. 5,420,328 issued to Campbell on May 30, 1995, which is incorporated herein by reference, refers to methods of synthesis of phosphonate esters. The phosphonate esters so produced may be screened to identify compounds which are ST receptor ligands.

U.S. Pat. No. 5,288,514 issued to Ellman on Feb. 22, 1994, which is incorporated herein by reference, refers to solid phase and combinatorial synthesis of benzodiazepine compounds on a solid support. Such methods and compounds may be used to identify ST receptor ligands according to the invention.

As noted above, ST receptor ligands may also be antibodies and fragments thereof. Indeed, antibodies raised to unique determinants of these receptors will recognize that protein, and only that protein and, consequently, can serve as a specific targeting molecule which can be used to direct novel diagnostics and therapeutics to this unique marker. In addition, these antibodies can be used to identify the presence of ST receptors or fragments of those receptors in biological samples, to diagnose the presence of colorectal cancer cells in vitro. Indeed, antibodies which specifically recognize this protein have been generated previously (Vaandrager et al., 1993 *J. Biolog. Chem.* 268:2174, which is incorporated herein by reference, 1993).

I claim:

1. A method of treating an individual suspected of suffering from metastasized colorectal cancer comprising the step of administering parenterally to said individual a pharmaceutical composition comprising a therapeutically effective amount of a conjugated compound comprising:
   a) a ST receptor binding moiety; and,
   b) an active moiety;
wherein said active moiety is a radiostable active agent that is a radiostable therapeutic agent.

2. The method of claim 1 wherein said ST receptor binding moiety is a peptide.

3. The method of claim 1 wherein said ST receptor binding moiety is selected from the group consisting of: SEQ ID NO:2, SEQ ID NO:3, SEQ ID NOS:5–56 and fragments and derivatives thereof having ST receptor binding activity.

4. The method of claim 1 wherein said ST receptor binding moiety is selected from the group consisting of: SEQ ID NO:2, SEQ ID NO:3, SEQ ID NO:5, SEQ ID NO:6 and SEQ ID NO:54.

5. The method of claim 1 wherein said an active moiety is selected from the group consisting of: methotrexate, doxorubicin, daunorubicin, cytosinarabinoside, etoposide, 5-4 fluorouracil, melphalan, chlorambucil, cis-platin, vindesine, mitomycin, bleomycin, purothionin, macromomycin, 1,4-benzoquinone derivatives, trenimon, ricin, ricin A chain, Pseudomonas exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, nitroimidazole, metronidazole and misonidazole.

6. The method of claim 1 wherein:

a) said ST receptor binding moiety is selected from the group consisting of: SEQ ID NO:2, SEQ ID NO:3, SEQ ID NOS:5–56 and fragments and derivatives thereof having ST receptor binding activity;

b) said an active moiety is selected from the group consisting of: methotrexate, doxorubicin, daunorubicin, cytosinarabinoside, etoposide, 5-4 fluorouracil, melphalan, chlorambucil, cis-platin, vindesine, mitomycin, bleomycin, purothionin, macromomycin, 1,4-benzoquinone derivatives, trenimon, ricin, ricin A chain, Pseudomonas exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, nitroimidazole, metronidazole and misonidazole.

7. The method of claim 1 wherein said an active moiety is selected from the group consisting of: methotrexate, doxorubicin, daunorubicin, cytosinarabinoside, cis-platin, vindesine, mitomycin and bleomycin, ricin A chain, Pseudomonas exotoxin and diphtheria toxin.

8. The method of claim 1 wherein:

a) said ST receptor binding moiety is selected from the group consisting of: SEQ ID NO:2, SEQ ID NO:3, SEQ ID NO:5, SEQ ID NO:6 and SEQ ID NO:54; and b) said an active moiety is selected from the group consisting of: methotrexate, doxorubicin, daunorubicin, cytosinarabinoside, cis-platin, vindesine, mitomycin and bleomycin, ricin A chain, Pseudomonas exotoxin and diphtheria toxin.

9. The method of claim 1 wherein said an active moiety is selected from the group consisting of chemotherapeutics, toxins and radiosensitizing agents.

10. The method of claim 1 wherein said pharmaceutical composition is administered intravenously.

11. The method of claim 1 wherein said ST receptor binding moiety is an ST receptor binding peptide having less than 25 amino acids.

12. The method of claim 11 wherein said active moiety is selected from the group consisting of chemotherapeutics, toxins and radiosensitizing agents.

13. The method of claim 11 wherein said ST receptor binding moiety is an ST receptor binding peptide having 13–25 amino acids.

14. The method of claim 11 wherein said active moiety is selected from the group consisting of: methotrexate, doxorubicin, daunorubicin, cytosinarabinoside, etoposide, 5-4 fluorouracil, melphalan, chlorambucil, cis-platin, vindesine, mitomycin, bleomycin, purothionin, macromomycin, 1,4-benzoquinone derivatives, trenimon, ricin, ricin A chain, Pseudomonas exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, nitroimidazole, metronidazole and misonidazole.

15. A method of treating an individual suspected of suffering from metastasized colorectal cancer comprising the steps of administering parenterally to said individual a pharmaceutical composition comprising a therapeutically effective amount of a conjugated compound comprising:

a) a ST receptor binding moiety; and, b) an active moiety;
wherein said active moiety is a radioactive agent.

16. The method of claim 15 wherein said active moiety is selected from the group consisting of: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt and $^{197}$Hg.

17. The method of claim 15 wherein said active moiety is selected from the group consisting of: $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi.

18. The method of claim 15 wherein said ST receptor binding moiety is a peptide.

19. The method of claim 15 wherein said ST receptor binding moiety is selected from the group consisting of: SEQ ID NO:2, SEQ ID NO:3, SEQ ID NOS:5–56 and fragments and derivatives thereof having ST receptor binding activity.

20. The method of claim 15 wherein said ST receptor binding moiety is selected from the group consisting of: SEQ ID NO:2, SEQ ID NO:3, SEQ ID NO:5, SEQ ID NO:6 and SEQ ID NO:54.

21. The method of claim 15 wherein
said ST receptor binding moiety is selected from the group consisting of SEQ ID NO:2, SEQ ID NO:3, SEQ ID NO:5, SEQ ID NO:6 and SEQ ID NO:54; and
said active moiety is selected from the group consisting of $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt and $^{197}$Hg.

22. The method of claim 15 wherein
said ST receptor binding moiety is selected from the group consisting of SEQ ID NO:2, SEQ ID NO:3, SEQ ID NO:5, SEQ ID NO:6 and SEQ ID NO:54; and
said active moiety is selected from the group consisting of $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi.

23. The method of claim 15 wherein said pharmaceutical composition is administered intravenously.

24. The method of claim 15 wherein said ST receptor binding moiety is an ST receptor binding peptide having less than 25 amino acids.

25. The method of claim 24 wherein said active moiety is selected from the group consisting of: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt and $^{197}$Hg.

26. The method of claim 24 wherein said active moiety is selected from the group consisting of: $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi.

27. The method of claim 24 wherein said ST receptor binding moiety is an ST receptor binding peptide having 13–25 amino acids.

28. The method of claim 1 wherein said pharmaceutical composition is administered into said individual's circulatory system.

29. The method of claim 1 wherein said pharmaceutical composition is administered intravenously.

30. The method of claim 1 wherein said ST receptor binding moiety is an antibody, FAb or F(Ab)$_2$.

31. The method of claim 1 wherein said ST receptor binding moiety is an antibody.

32. The method of claim 1 wherein said active moiety is a radiostable active agent selected from the group consisting of: compounds that cause cell death, compounds that inhibit cell division, and compounds that induce cell differentiation.

33. The method of claim 32 wherein said pharmaceutical composition is administered into said individual's circulatory system.

34. The method of claim 32 wherein said pharmaceutical composition is administered intravenously.

35. The method of claim 32 wherein said ST receptor binding moiety is a peptide.

36. The method of claim 32 wherein said ST receptor binding moiety is selected from the group consisting of: SEQ ID NO:2, SEQ ID NO:3, SEQ ID NOS:5–56 and fragments and derivatives thereof having ST receptor binding activity.

37. The method of claim 32 wherein said ST receptor binding moiety is selected from the group consisting of: SEQ ID NO:2, SEQ ID NO:3, SEQ ID NO:5, SEQ ID NO:6 and SEQ ID NO:54.

38. The method of claim 32 wherein said ST receptor binding moiety is an antibody, FAb or F(Ab)$_2$.

39. The method of claim 32 wherein said ST receptor binding moiety is an antibody.

40. The method of claim 1 wherein said active moiety is a radiostable active agent selected from the group consisting of: cytotoxic drugs, cytostatic drugs and protein toxins.

41. The method of claim 40 wherein said pharmaceutical composition is administered into said individual's circulatory system.

42. The method of claim 40 wherein said pharmaceutical composition is administered intravenously.

43. The method of claim 40 wherein said ST receptor binding moiety is a peptide.

44. The method of claim 40 wherein said ST receptor binding moiety is selected from the group consisting of: SEQ ID NO:2, SEQ ID NO:3, SEQ ID NOS:5–56 and fragments and derivatives thereof having ST receptor binding activity.

45. The method of claim 40 wherein said ST receptor binding moiety is selected from the group consisting of: SEQ ID NO:2, SEQ ID NO:3, SEQ ID NO:5, SEQ ID NO:6 and SEQ ID NO:54.

46. The method of claim 40 wherein said ST receptor binding moiety is an antibody, FAb or F(Ab)$_2$.

47. The method of claim 40 wherein said ST receptor binding moiety is an antibody.

48. The method of claim 15 wherein said ST receptor binding moiety is an antibody, FAb or F(Ab)$_2$.

49. The method of claim 15 wherein said ST receptor binding moiety is an antibody.

50. A method of treating an individual suspected of suffering from metastasized colorectal cancer comprising the steps of administering parenterally to said individual a pharmaceutical composition comprising a therapeutically effective amount of a conjugated compound comprising:

a) a ST receptor binding moiety; and, b) an active moiety;
wherein said active moiety is a radioactive agent and said ST receptor binding moiety is a peptide.

51. The method of claim 50 wherein said ST receptor binding moiety is selected from the group consisting of: SEQ ID NO:2, SEQ ID NO:3, SEQ ID NOS:5–56 and fragments and derivatives thereof having ST receptor binding activity.

52. The method of claim 50 wherein said ST receptor binding moiety is selected from the group consisting of: SEQ ID NO:2, SEQ ID NO:3, SEQ ID NO:5, SEQ ID NO:6 and SEQ ID NO:54.

53. The method of claim 50 wherein said pharmaceutical composition is administered into the circulatory system of said individual.

54. The method of claim 50 wherein said pharmaceutical composition is administered intravenously.

55. A method of treating an individual suspected of suffering from metastasized colorectal cancer comprising the steps of administering parenterally to said individual a pharmaceutical composition comprising a therapeutically effective amount of a conjugated compound comprising:

a) a ST receptor binding moiety; and, b) an active moiety;

wherein said active moiety is a radioactive agent and said ST receptor binding moiety is an antibody, FAb or F(Ab)$_2$.

56. The method of claim 55 wherein said ST receptor binding moiety is an antibody.

57. The method of claim 55 wherein said pharmaceutical composition is administered into the circulatory system of said individual.

58. The method of claim 55 wherein said pharmaceutical composition is administered intravenously.

* * * * *

UNITED STATES PATENT AND TRADEMARK OFFICE
CERTIFICATE OF CORRECTION

PATENT NO. : 5,879,656
DATED : March 9, 1999
INVENTOR(S) : Scott A. Waldman

It is certified that error appears in the above-indentified patent and that said Letters Patent is hereby corrected as shown below:

Col. 53, line 7, "associatec" should be --associated--.

Col. 77, line 41, "an" should be deleted.

Signed and Sealed this

Twenty-fourth Day of August, 1999

Attest:

Q. TODD DICKINSON

*Attesting Officer*      *Acting Commissioner of Patents and Trademarks*